(12) United States Patent
Niwa et al.

(10) Patent No.: US 7,691,568 B2
(45) Date of Patent: Apr. 6, 2010

(54) ANTIBODY COMPOSITION-CONTAINING MEDICAMENT

(75) Inventors: Rinpei Niwa, Machida (JP); Kenya Shitara, Machida (JP)

(73) Assignee: Kyowa Hakko Kirin Co., Ltd, Tokyo (JP)

( * ) Notice: Subject to any disclaimer, the term of this patent is extended or adjusted under 35 U.S.C. 154(b) by 342 days.

(21) Appl. No.: 10/409,598

(22) Filed: Apr. 9, 2003

(65) Prior Publication Data

US 2004/0109865 A1  Jun. 10, 2004

(30) Foreign Application Priority Data

Apr. 9, 2002 (JP) ............... 2002-106949

(51) Int. Cl.
*A61K 39/395* (2006.01)
(52) U.S. Cl. .............. 435/6; 424/133.1; 424/172.1; 424/174.1
(58) Field of Classification Search ............ 435/6; 424/133.1, 172.1, 174.1
See application file for complete search history.

(56) References Cited

U.S. PATENT DOCUMENTS

| | | | |
|---|---|---|---|
| 4,350,683 A | 9/1982 | Galfre et al. | |
| 4,721,777 A | 1/1988 | Uemura et al. | |
| 4,757,018 A | 7/1988 | Brown | |
| 4,816,567 A | 3/1989 | Cabilly | |
| 4,849,509 A | 7/1989 | Thurin et al. | |
| 5,272,070 A | 12/1993 | Lehrman et al. | |
| 5,453,363 A | 9/1995 | Rudolph | |
| 5,464,764 A | 11/1995 | Capecchi et al. | |
| 5,614,385 A | 3/1997 | Oppermann et al. | |
| 5,658,789 A | 8/1997 | Quaranta et al. | |
| 5,665,569 A | 9/1997 | Ohno | |
| 5,672,502 A | 9/1997 | Birch et al. | |
| 5,728,568 A | 3/1998 | Sullivan | |
| 5,830,470 A | 11/1998 | Nakamura et al. | |
| 5,858,983 A | 1/1999 | Seed et al. | |
| 5,880,268 A | 3/1999 | Gallatin et al. | |
| 5,891,996 A | 4/1999 | Mateo de Acosta del Rio et al. | |
| 5,922,845 A | 7/1999 | Deo et al. | |
| 5,932,703 A | 8/1999 | Godiska et al. | |
| 5,935,821 A | 8/1999 | Chatterjee et al. | |
| 5,977,316 A | 11/1999 | Chatterjee et al. | |
| 6,018,032 A | 1/2000 | Koike et al. | |
| 6,054,304 A | 4/2000 | Taniguchi et al. | |
| 6,129,913 A | 10/2000 | Takasawa et al. | |
| 6,150,132 A | 11/2000 | Wells et al. | |
| 6,169,070 B1 | 1/2001 | Chen et al. | |
| 6,238,894 B1 | 5/2001 | Taylor et al. | |
| 6,245,332 B1 | 6/2001 | Butcher et al. | |
| 6,291,219 B1 | 9/2001 | Taniguchi et al. | |
| 6,350,868 B1 | 2/2002 | Weston et al. | |
| 6,437,098 B1 | 8/2002 | Shitara et al. | |
| 6,455,043 B1 | 9/2002 | Grillo-Lopez | |
| 6,488,930 B1 | 12/2002 | Wu et al. | |
| 6,498,015 B1 | 12/2002 | Godiska et al. | |
| 6,602,684 B1 | 8/2003 | Umana et al. | |
| 6,737,056 B1 | 5/2004 | Presta | |
| 6,946,292 B2 * | 9/2005 | Kanda et al. ............. 435/326 |
| 6,986,890 B1 | 1/2006 | Shitara et al. | |
| 6,989,145 B2 | 1/2006 | Shitara et al. | |
| 7,033,589 B1 | 4/2006 | Reff et al. | |
| 7,138,117 B1 | 11/2006 | Wu et al. | |
| 7,214,775 B2 | 5/2007 | Hanai et al. | |
| 7,297,775 B2 | 11/2007 | Idusogie et al. | |
| 2002/0019341 A1 | 2/2002 | Butcher et al. | |
| 2002/0098527 A1 | 7/2002 | Shitara et al. | |
| 2002/0160015 A1 | 10/2002 | Wells et al. | |
| 2002/0187930 A1 | 12/2002 | Wells et al. | |
| 2003/0115614 A1 | 6/2003 | Kanda et al. | |
| 2003/0157108 A1* | 8/2003 | Presta ................. 424/145.1 |
| 2003/0158389 A1 | 8/2003 | Idusogie et al. | |
| 2003/0170813 A1 | 9/2003 | Suga et al. | |
| 2003/0175273 A1 | 9/2003 | Shitara et al. | |
| 2003/0190316 A1 | 10/2003 | Kakuta et al. | |
| 2004/0002077 A1 | 1/2004 | Taira et al. | |

(Continued)

FOREIGN PATENT DOCUMENTS

CA  2424602  4/2002

(Continued)

OTHER PUBLICATIONS

Freshney (Culture of Animal Cells, A Manual of Basic Technique, Alan R. Liss, Inc., 1983, New York, p. 4).*
Dermer (Bio/Technology, 1994, 12:320).*
Davis et al. (J. Clinical Oncology 2000; 18: 3135-3143).*
Kanda et al. (Biotechnology and Bioengineering 2006; 94: 680-688).*
Haidar et al. (Eur. J. Haematol. 2003; 70: 330-332).*
Ripka et al, Two Chinese Hamster Ovary Glycosylation Mutants Affected in the Conversion of GDP-Mannose to GDP-Fucose, Archives of Biochemistry and Biophysics, vol. 249, No. 2, 1986, pp. 533-545.
Shitara et al, A new vector for the high level expression of chimeric antibodies in myeloma cells, Journal of Immunological Methods, vol. 167, 1994, pp. 271-278.

(Continued)

*Primary Examiner*—Brandon J Fetterolf
(74) *Attorney, Agent, or Firm*—Sughrue Mion, PLLC

(57) ABSTRACT

A medicament for treating a patient who cannot be cured with a medicament comprising as an active ingredient an antibody composition produced by a cell unresistant to a lectin which recognizes a sugar chain in which 1-position of fucose is bound to 6-position of N-acetylglucosamine in the reducing end through α-bond in a complex N-glycoside-linked sugar chain, which comprises as an active ingredient an antibody composition produced by a cell resistant to a lectin which recognizes a sugar chain in which 1-position of fucose is bound to 6-position of N-acetylglucosamine in the reducing end through α-bond in a complex N-glycoside-linked sugar chain, and a method for screening the patient by using the medicament.

5 Claims, 16 Drawing Sheets

U.S. PATENT DOCUMENTS

| | | |
|---|---|---|
| 2004/0072290 A1 | 4/2004 | Umana et al. |
| 2004/0093621 A1 | 5/2004 | Shitara et al. |
| 2004/0110282 A1 | 6/2004 | Kanda et al. |
| 2004/0110704 A1 | 6/2004 | Yamane et al. |
| 2004/0132140 A1 | 7/2004 | Satoh et al. |
| 2005/0048647 A1 | 3/2005 | Taira et al. |
| 2005/0074843 A1 | 4/2005 | Umana et al. |
| 2005/0079605 A1 | 4/2005 | Umana et al. |
| 2005/0160485 A1 | 7/2005 | Taniguchi |
| 2005/0187380 A1 | 8/2005 | Shitara et al. |
| 2005/0216958 A1 | 9/2005 | Yamane et al. |
| 2005/0226867 A1 | 10/2005 | Iida et al. |
| 2005/0262593 A1 | 11/2005 | Kanda et al. |
| 2005/0272916 A1 | 12/2005 | Hanai et al. |
| 2005/0276805 A1 | 12/2005 | Hanai et al. |
| 2005/0287138 A1 | 12/2005 | Iida et al. |
| 2006/0024800 A1 | 2/2006 | Hanai et al. |
| 2006/0063254 A1 | 3/2006 | Kanda et al. |
| 2006/0064781 A1 | 3/2006 | Kanda et al. |
| 2006/0078990 A1 | 4/2006 | Kanda et al. |
| 2006/0078991 A1 | 4/2006 | Kanda et al. |
| 2006/0223147 A1 | 10/2006 | Nishiya et al. |
| 2007/0111281 A1 | 5/2007 | Sondermann et al. |
| 2007/0166300 A1 | 7/2007 | Hanai et al. |
| 2007/0166301 A1 | 7/2007 | Hanai et al. |
| 2007/0166302 A1 | 7/2007 | Hanai et al. |
| 2007/0166303 A1 | 7/2007 | Hanai et al. |
| 2007/0166304 A1 | 7/2007 | Hanai et al. |
| 2007/0166305 A1 | 7/2007 | Hanai et al. |
| 2008/0261301 A1 | 10/2008 | Kanda et al. |

FOREIGN PATENT DOCUMENTS

| | | |
|---|---|---|
| EP | 0481791 | 4/1992 |
| EP | 623352 | 11/1994 |
| EP | 0625574 | 11/1994 |
| EP | 0811691 | 12/1997 |
| EP | 0816503 | 1/1998 |
| EP | 882794 | 9/1998 |
| EP | 0292965 | 11/1998 |
| EP | 1092037 | 4/2001 |
| EP | 1109570 | 6/2001 |
| EP | 1174148 | 1/2002 |
| EP | 1176195 | 1/2002 |
| EP | 1254666 | 11/2002 |
| EP | 1266663 | 12/2002 |
| EP | 1314437 | 5/2003 |
| EP | 1331266 | 7/2003 |
| EP | 1443961 | 8/2004 |
| EP | 1498485 A1 | 1/2005 |
| EP | 1498490 A1 | 1/2005 |
| EP | 1498491 A1 | 1/2005 |
| EP | 1500698 A1 | 1/2005 |
| EP | 1676910 | 7/2006 |
| EP | 1705251 | 9/2006 |
| FR | 2708467 | 2/1995 |
| JP | 62194459 | 8/1987 |
| JP | 62244441 | 10/1987 |
| JP | 6189781 | 7/1994 |
| JP | 7502497 | 3/1995 |
| JP | 9500894 | 1/1997 |
| JP | 9049836 | 2/1997 |
| JP | 10257893 | 9/1998 |
| JP | 2002539079 | 11/2002 |
| JP | 2002544173 | 12/2002 |
| JP | 2003350165 | 10/2003 |
| JP | 2005058111 | 3/2005 |
| JP | 11127890 | 5/2005 |
| WO | 86005807 | 10/1986 |
| WO | WO 91/19501 | 12/1991 |
| WO | 93008837 | 5/1993 |
| WO | 93022335 | 11/1993 |
| WO | 94000136 | 1/1994 |
| WO | 94002616 | 2/1994 |
| WO | WO 94/16094 | 7/1994 |
| WO | 94022478 | 10/1994 |
| WO | 95003826 | 2/1995 |
| WO | 95024494 | 9/1995 |
| WO | 96007429 | 3/1996 |
| WO | 96023068 | 8/1996 |
| WO | 96026268 | 8/1996 |
| WO | 86005817 | 10/1996 |
| WO | 97010354 | 3/1997 |
| WO | WO 97/27303 | 7/1997 |
| WO | 97/30087 | 8/1997 |
| WO | 97033978 | 9/1997 |
| WO | 97037683 | 9/1997 |
| WO | 97/37683 | 10/1997 |
| WO | 98054964 | 12/1998 |
| WO | 99015666 | 4/1999 |
| WO | 99025380 | 5/1999 |
| WO | 99037329 | 7/1999 |
| WO | 99/54342 | 10/1999 |
| WO | 99/64618 | 12/1999 |
| WO | 00000219 | 1/2000 |
| WO | 00012113 | 3/2000 |
| WO | 00034490 | 6/2000 |
| WO | 00041724 | 7/2000 |
| WO | 00042074 | 7/2000 |
| WO | 00049153 | 8/2000 |
| WO | 00059547 | 10/2000 |
| WO | 00062790 | 10/2000 |
| WO | WO 00/61739 | 10/2000 |
| WO | 0064262 | 11/2000 |
| WO | 00066160 | 11/2000 |
| WO | 00067791 | 11/2000 |
| WO | 00067795 | 11/2000 |
| WO | 00073481 | 12/2000 |
| WO | 01060405 | 8/2001 |
| WO | 01064754 | 9/2001 |
| WO | 01077181 | 10/2001 |
| WO | 02002793 | 1/2002 |
| WO | 02010743 | 2/2002 |
| WO | 02012347 | 2/2002 |
| WO | WO 02/31140 A1 | 4/2002 |
| WO | 02046186 | 6/2002 |
| WO | 03018635 | 3/2003 |
| WO | WO 03/035835 | 5/2003 |
| WO | 03046186 | 6/2003 |
| WO | 03055993 | 7/2003 |
| WO | 03063767 | 8/2003 |
| WO | 03085089 | 10/2003 |
| WO | 03085107 | 10/2003 |
| WO | 03085118 | 10/2003 |
| WO | 06020114 | 2/2006 |

OTHER PUBLICATIONS

Davies et al, Expression of GnTIII in a recombinant Anti-CD20 CHO Production cell Line: Expression of Antibodies with Altered Glycoforms Leads to an Increase in ADCC Through Higher Affinity for Fc gamma RIII, Biotechnology and Bioengineering vol. 74, No. 4, 2001, pp. 288-294.

Hackett et al, Recombinant Mouse-Human Chimeric Antibodies as Calibrators in Immunoassays That Measure Antibodies to *Toxoplasma gondii*, Journal of Clinical Microbiology, vol. 36, No. 5, 1998, pp. 1277-1284.

Elbashir et al, Duplexes of 21-nucleotide RNAs mediate RNA interference in cultured mammalian cells, Nature, 2001, vol. 411, pp. 494-498.

Shields et al, High Resolution Mapping of the Binding Site on Human IgG1 for Fc gamma RI, Fc gamma RII, Fc gamma RIII, and FcRn and Design of IgG1 Variants with Improved Binding to the Fc gamma R, The Journal of Biological Chemistry, vol. 276, No. 9, 2001, pp. 6591-6604.
Shields et al, Lack of Fucose on Human IgG1 N-Linked Oligosaccharide Improves Binding to Human Fc gamma RIII and Antibody-dependent Cellular Toxicity, The Journal of Biological Chemistry, vol. 277, No. 30, 2002, pp. 26733-26740.
Shinkawa et al, The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity, The Journal of Biological Chemistry, vol. 278, No. 5, 2003, pp. 3466-3473.
U.S. Appl. No. 11/279,748, filed Apr. 2006, Kanda et al.
U.S. Appl. No. 09/958,307, filed Oct. 2001, Kanda et al.
Furukawa et al Protein, Nucleic Acid and Enzyme, 43, 2309-2317 (1998).
Maly et al, Cell, vol. 86, 643-653, Aug. 23, 1996.
Wright et al. Tibtech, 15, 26-32 (1997).
Breton et al, Glycobiology, 8, No. 1, 87-94 (1998).
Asano et al, The EMBO Journal, vol. 16, No. 8, pp. 1850-1857 (1997).
Oriol et al. Glycobiology, 9, No. 4, 323-334 (1999).
Raju, et al. (2000) Glycobiology, 10(5): 477-86.
Stryer (1988) Biochemistry, 3rd Ed., Freeman and Co., New York, NY, pp. 35-37.
Jones, et al. (2001) Pharmacogenomics J., 1(2): 126-34.
Lifely, et al. (1995) Glycobiology, 5(8): 813-22.
U.S. Appl. No. 60/337,642, filed Oct. 2001, Presta.
U.S. Appl. No. 60/347,694, filed Jan. 2002, Presta.
U.S. Appl. No. 60/082,581, filed Apr. 1998, Umana et al.
Wilson et al, "Structural analysis of N-glycans from allergenic grass, ragweed and tree pollens: Core 1, 3-linked fucose and xylose present in all pollens examined", Glycoconjugate Journal 15(11):1055-1070 (1998).
Boyd et al, Molecular Immunology, 1995, vol. 32, No. 17/18, pp. 1311-1318.
Clark, Chem. Immunol. 1997, vol. 65, pp. 88-110.
Ohyama et al, The Journal of Biological Chemistry, 1998, vol. 273, No. 23, pp. 14582-14587.
Sullivan et al, The Journal of Biological Chemistry, 1998, vol. 273, No. 14, pp. 8193-8202.
Ripka et al, Somatic Cell and Molecular Genetics, 1986, vol. 12, No. 1 pp. 51-62.
Jefferies et al (BioChem J. 268 :529-537 (1990).
Routier et al (Glycoconjugate Journal 14 :201-207 (1997)).
Supplementary European Search Report dated Sep. 11, 2006.
Eckart Grabenhorst, et al., "Genetic engineering of recombinant glycoproteins", Glycoconjugate Journal, 1999, 16(2):81-97.
U.S. Appl. No. 60/572,899, filed May 2004.
Abbas et al., Cellular and Molecular Immunology, 2nd Ed., by WB Saunders Co., Philidelphia, PA, p. 219 (1994).
Alabyev et al., Developmental & Comparative Immunology, 24:765-770 (2000).
Anders et al., Exp. Nephrol., 8:181-193 (2000).
Andrew et al., J. Immunol., 166(1):103-111 (2001).
Atkinson et al., Canadian J. of Biochem. and Cell Biology, 62(12):1343-1350 (1984).
Awwad et al., Cancer Immunological Immunother., 38:23-30 (1994).
Bartunkova et al., APMIS, 108(6):409-416 (2000).
Becker et al., Biochemica et Biophysica Acta., 1455:193-204 (1999).
Bei et al., J. of Immunological Methods, 182(2):245-255 (1995).
Bendig, Methods: A Companion to Methods in Enzymology, 8:83-93 (1995).
Berg et al., Biotechniques, 14(6):972-978 (1993).
Bibila et al., Biotechnol. Prog., 10(1):87-96 (1994).
Bishop, Reprod. Nutr. Dev., 36:607-618 (1998).
Biswas et al., Cancer Research, 66(13):6816-6825 (2006).
Blumenthal et al., American J. of Pathology, 156(5):1581-1588 (2000).
Blumenthal et al., "Unique Molecular Markers in Human Endometriosis: Implications for Diagnosis and Therapy", Expert Reviews in Molecular Medicine, pp. 1-12 (Nov. 2001).
Bonecchi et al., J. Exp. Med., 87(1):129-134 (1998).
Bonin et al., PNAS, 94:2085-2090 (1997).
Brady et al., Curr. Top. Microbiol. Immunol., 2005:1-18 (1996).
Brams et al., Int. Immunopharmacol., 1:277-294 (2001).
Brekke et al., Mol. Immunol., 30:1419-1425 (1993).
Brinkman-Van Der Linden et al., J. of Biological Chemistry, 271(24):14492-14495 (1996).
Broad et al., Cytotechnology, 5:47-55 (1991).
Brown et al., Proc. Natl. Acad. Sci., USA, 88(7):2663-2667 (1991).
Burgess et al., J. of Cell Bio., 111:2129-2138 (1990).
Byrd et al., J. of Biological Chemistry, 257(24):14657-14666 (1982).
Cambi et al., Cellular Microbiology, 7(4):481-488 (2005).
Cameron, Mol. Biotech, 7:253-265 (1997).
Canadian Office Action dated Jul. 31, 2007 (CA 2,424,602).
Capecchi et al., Scientific American, 270:34-41 (1994).
Cartoon et al., Blood, 99(3):754-758 (2002).
Caspi et al., J. of Biological Chemistry, 278(40):38740-38748 (2003).
Castro et al., Research School of Biosciences, United Kingdom., 19:27-36 (1995).
Chantry et al., Current Drug Targets- Inflammation & Allergy, 1:109-116 (2002).
Chen et al., Journal of Pharmaceutical Sciences, 83(12):1657-1661 (1994).
Christensen et al., Glycobiology, 10(9):931-939 (2000).
Chuntharapai et al., Meth. Enzymol., 288:15-27 (1997).
Clarke et al., Glycobiology, 9(2):191-202 (1999).
Clemetson et al., Blood, 96(13):4046-4054 (2000).
Co et al., Proc. Natl. Acad. Sci., 88(7):2869-2873 (1991).
Co et al., Cancer Res., 56:1118-1125 (1996).
Cooper et al., Eur. J. Immunol. 33:666-675 (2003).
Cragg et al., Blood, 103:2738-2743 (2004).
Czuczman et al., Journal of Clinical Oncology, 17(1): 268-276 (1999).
D'Ambrosio et al., J. of Immunology, Cutting Edge, 0022-1767/98/ 502.00, pp. 5111-5115 (1998).
da Silva et al., the Journal of Immunology, 168:4462-4471 (2002).
Denning et al., Nat. Biotech, 19:559-562 (2001).
Dharmacon siRNA design for AB025198, accessed http://www.dharmacon.com/DesinCenter/DesiqnCenterPage.aspx on Apr. 15, 2008.
Dharmacon siRNA design for AF042377, accessed http://www.dharmacon.com/DesinCenter/DesiqnCenterPage.aspx on Apr. 15, 2008.
Domagala et al., Med. Sci., Monit., 7(2):325-331 (2001).
Domino et al., Molecular and Cellular Biology, 21(24):8336-8345 (2001).
Duncan et al.; *Molecular Immunology*, 44:3641-3652 (2007).
Edmunds et al., Blood, 91(12):4561-4571 (1998).
Environmental Conditions for Cell Growth, Part 2C.
EP 00969908 - Supplementary European Search Report dated Apr. 18, 2005.
EP 00969908.3 - Office Action issued Jul. 30, 2007.
EP 01974718.7-Supplementary European Search Report dated May 19, 2005.
EP 01974718.7 Supplementary European Search Report dated Jun. 1, 2005.
EP 03723096 Supplementary European Search Report dated Oct. 27, 2006.
EP 02793391 Supplementary European Search Report dated Mar. 28, 2006.
EP 03723098 Supplementary European Search Report dated Nov. 14, 2006.
EP 03723099.2 Supplementary European Search Report dated Nov. 14, 2006.
EP 03720896 Supplementary European Search Report dated Jul. 22, 2005.
EP 03720897.2 Supplementary European Search Report dated Jul. 18, 2006.
EP 04773700 Supplementary European Search Report dated Aug. 21, 2008.
EP 04773766.3 Supplementary European Search Report dated Oct. 16, 2006.
EP 04773768.9 European Search Report dated Mar. 10, 2009.

EP 04773769 Supplementary European Search Report dated Feb. 7, 2007.
EP 04773774.7 Supplementary European Search Report dated Aug. 28, 2007.
EP 04773775 Supplementary European Search Report dated Nov. 27, 2008.
EP 04773776 Supplementary European Search Report dated Nov. 19, 2007.
EP 04773776.2 Supplementary Partial European Search Report dated Aug. 2, 2007.
EP 04801651.3 Supplementary European Search Report dated Feb. 20, 2008.
EP 05768941 European Search Report dated Dec. 27, 2007.
EP 05799028 Supplementary European Search Report dated Mar. 10, 2008.
Ersdal-Badju et al., Biochem. J., 310:323-330 (1995).
Ferrara et al., Biotechnology and Bioengineering; 93(5):851-861 (2006).
Finne et al., Inter. J. of Cancer, 43(2):300-304 (1989).
Flieger et al., Hybridoma, 18(1):63-68 (1999).
Frade et al., J. Clin. Invest., 100(3):497-502 (1997).
Franzen et al., J. Biol. Chem., 255(11):5090-5093 (1980).
Friedberg et al., British Journal of Hematology, 117:828-834 (2002).
Garone et al., Biochem., 35:8881-8889 (1996).
Gawlitzek et al., Biotechnology and Bioengineering, 68(6):637-646 (2000).
Gerard et al., Nature Immunol. 2:108-115 (2001).
Ginaldi et al, Leukemia Research, 22(2):185-191 (1998).
Glycine MSDS, Mallinckrodt chemicals, p. 1-6 (2005).
Goeddel, *Chest*, 116:1-8 (1999).
Goldenberg, Clinical Therapeutics, 21(2):309-317 (1999).
Gomez et al., Mol. Biol. Evol., 21:266-275 (2004).
Griffiths, Microscopy Research and Technique, 41(5):344-358 (1998).
Hagberg et al., Medical Oncolology, 22:191-194 (2005).
Hale et al., J. Immunol. Methods, 103:59-67 (1987).
Hale et al., J. of Biological Regul. Homeos. Agents, 15:386-391 (2001).
Hallouin et al., Inter. J. of Cancer, 80(4):606-611 (1999).
Hanson et al., Molecular and Cellular Biology, 15(1):45-51 (1995).
Harada et al., Sanfujinka Chiryo, 86(6):1048-1054 (2003).
Hasty et al., "Gene targeting vectors for mammalian cells", In: Joyner Al, editor, Gene Targeting, New York: Oxford University Press, pp. 1-31 (Year).
Hayashi et al.; DNA Sequence; 11(1-2):91-96 (2000).
He et al., J. Immunol., 160(2):1029-1035 (1998).
Hennett et al., Biochemica et Biophysica Acta, 1473(1):123-136 (1999).
Hirose et al., Thrombosis Research, 119:631-641 (2007).
Hirschberg, Journal of Clinical Investigation, 108(1):3-6 (2001).
Holschneider et al., Int. J. Dev. Neuroscience, 18(6):615-618 (2000).
Horowitz et al., Proc. Natl. Acad. Sci., USA, 85:8678-8682 (1988).
Houdebine, J. Biotech., 34:269-287 (1994).
Huang et al., J. of Biol. Chemistry, 275(40):31353-31360 (2000).
Humpherys et al., Science, 293:95-97 (2001).
Hunter et al., Current Biology, 9:R440-R442 (1999).
Idusogie et al., The Journal of Immunology, 164:4178-4184 (2000).
Iellem et al., J. Exp. Med., 194(6):847-853 (2001).
iHOP, www.i hop-net.org, p. 1.
Imai et al., International Immunology, 11(1):81-88 (1999).
Javaud et al., Molecular Biology and Evolution, 17(11):1661-1672 (2000).
Jen et al., Stem Cells, 18:307-319 (2000).
Jensen et al., Ann. Hematol., 77:89-91 (1998).
Josh et al., Curr. Opin. Plant Biol., 8:223-226, Abstract (2005).
Jones et al., Blood, 96(2):685-690 (2000).
JP 2000611663 - Telephonic Correspondence Record issued Apr. 15, 2009 (and attached Third Party Observation).
Junghans et al., Cancer Res., 50(5):1495-1502 (1990).
Kabat et al., Sequences of proteins of immunological interest, 4th Edition, pp. 307-308 (1987).
Kanazawa et al., Cancer Immunology Immunotherapy, 49(4-5):253-258 (2000).
Kanda et al., J. of Biotechnology, 130(3):300-310 (2007).
Kappel et al., Current Opinion in Biotechnology, 3:548-553 (1992).
Kashmiri et al., Methods, 36:25-34 (2005).
Kawai et al., Nature, 409(6821):685-690 (2001).
Keen et al., Biology Research Division, United Kingdom., 17:193-202 (1995).
Kilmartin et al.; J. of Cell Biology, 93:576-582 (1982).
Kim et al., Arch., Pharm. Res., 20(4):297-305 (1997).
Kirchhoff, Biology of Reproduction, 50:896-902 (1994).
Kojima et al., Journal of Biochemistry, 124:726-737 (1998).
Koyama et al., Int. J. Gynecol. Obstet., 43:45-50 (1993).
Kruszewska et al., Glycobiology, 10(10):983-991 (2000).
Kubota et al, J. of Immunology, 145(11):3924-3931 (1990).
Kuroiwa et al., Nature Genetics, 36(7):775-780 (2004).
Kushihata et al., Transplantation, 78(7):995-1001 (2004).
Kusumoto, Igaku no Ayumi (Progress Med. Sci.), 190(5):522-529 (1999).
Ladisch et al., *The Lancet*, pp. 136-138 (1985).
Landolfi et al., J. Immunol., 166(3):1748-1754 (2001).
Lazar et al., Mol. & Cell Bio., 8:1247-1252 (1988).
Lederman et al., Mol. Immunol. 28:1171-1181 (1991).
Letter from Terry Kramer dated May 9, 2005 and Third Party Submission dated May 9, 2005 (received May 12, 2005).
Leonard et al., Immunological Reviews, 148:97-114 (1995).
Li et al., Acta Pharmacologicia Sinica, 21(11):1005-1010 (2000).
Liu et al., Mechanisms of Development, 116:227-230 (2002a).
Liu et al., J. of Cancer Res. and Clinical Oncology, 128(4):189-196 (2002b).
Lubiniecki et al., Dev. Biol. Stand., 99:153-156 (1999).
Lubke et al., Nature Genetics, 28(1):73-76 (2001).
Luhtala et al., Poultry Science, 77:1858-1873 (1998).
Luhn et al., Nature Genetics, 28(1):69-72 (2001).
Lyons et al., Current Biology, 15:513-524 (2005).
Ma et al., Glycobiology, 16(12):158R-184R (2006).
MacEwan; Cellular Signaling, 14:477-492 (2002).
Majeau et al., Journal of Immunology, 152:2753-2767 (1994).
Manfredi et al., Cancer Res., 59:5392-5397 (1999).
Marshall et al., Blood, 103(5):1755-1762 (2004).
Martinez-Duncker et al., Glycobiology, 14(1):13-25 (2004).
Merck Manuals Online Medical Library, Whitehouse Station, NJ: Merck Research Laboratories, 2006-2007, retrieved Oct. 2007, http://www.merck.com/mmpe/print/sec11ch143/ch143b.html, Hodgkin lymphoma, p. 1-5.
Merck Manuals Online Medical Library, Whitehouse Station, NJ: Merck Research Laboratories, 2006-2007, retrieved Oct. 2007, http://www.merck.com/mmpe/print/sec11ch142/ch142a.html, Leukemia, pp. 1-4.
Michaelsen et al., Scandinavian Journal of Immunology, 32:517-528 (1990).
Moreadith et al., J. Mol. Med., 75:208-216 (1997).
Mori et al., Biotechnology and Bioengineering, 88(7):901-908 (2004).
Mueller et al., J. of Immunology, 144(4):1382-1386 (1990).
Mullins et al., Journal of Clinical Investigation, 97(7):1557-1560 (1996).
Murray et al., The Annals of Pharmacotherapy, 31:1335-1338 (1997).
Nakamura et al., Cancer Research, 54:1511-1516 (1994).
Nakamura et al., Cancer Research, 59(20):5323-5330 (1999).
Nakamura et al., Molecular Immunology, 37:1035-1046 (2000).
Natsumi et al., J. of Immunol. Methods, 306:93-103 (2005).
Nishii et al., Br. J. Haematol., 91:169-172 (1995).
Niwa et al., Clinical Cancer Research, 10:6248-6255 (2004).
Norderhaug et al., European Journal of Immunology, 21:2379-2384 (1991).
Nose, J. Immunology., 145(3):910-941 (1990).
Okajima et al., Cell, 111(6):893-904 (2002).
Okazaki et al., Seikagaku, 77:45-50 (2005).
Olson et al., Arch. Biochem. Biophys., 341(2):212-221 (1997).
Omasa et al., Journal of Bioscience and Bioengineering, 106(2):168-173 (2008).
Onishi, Igaku no Ayumi (Progress Med. Sci.), 190(5):481-485 (1999).
Onizuka et al., Cancer Research, 59:3128-3133 (1999).

Ozturk et al., Journal of Biotechnology, 16:259-278 (1990).
Padlan et al., PNAS, 86:5938-5942 (1989).
Pastuszak et al.; J. of Biological Chemistry, 273(46):30165-30174 (1998).
PCT/JP2004/015315 International Search Report dated Feb. 1, 2005.
PCT/JP2004/015317 International Search Report dated Feb. 1, 2005.
PCT/JP2004/015325 International Search Report dated Feb. 1, 2005.
PCT/JP2005/014408 International Preliminary Report on Patentability dated Feb. 6, 2007.
Pearson, Nature, 415(6867):8-9 (2002).
Peipp et al.; *Blood.*, 112:2390-2399 (2008).
Pierrot et al., *Biochemical and Biophysical Res. Comm.*, 288:328-339 (2001).
Polejaeva et al., Theriogenology, 53(1): 117-126 (2000).
Potelligent Technology, BioWa, Inc., internet address: biowa.com/news/pdf/Bio2003%20&%20Anti-Cancer%20BioWa%20Non%20Confidential.pdf#search=%22Potelligent%20Techology%20BioWa%2C%20Inc.%20pdf%22 (Jul. 21, 2004).
Power et al., J. of Biological Chemistry, 270(33):19495-19500 (1995).
Prati et al., Biotechnology and Bioengineering, 59(4):445-450 (1998).
Priatel et al., Glycobiology, 7(1):45-56 (1997).
Pulczynski et al., Blood, 6:1549-1557 (1993).
Pulglielli et al., The J. of Biological Chemistry, 274(50):35596-35600 (1999).
Queen et al., Proc. Natl. Acad. Sci., 86(24):10029-10033 (1989).
Rader et al., PNAS, 95:8910-8915 (1998).
Rasmussen et al., Cytotechnology, 28:31-42 (1998).
Reff et al., Blood, 83:435-445 (1994).
Reitman et al., J. of Biological Chemistry, 255(20):9900-9906 (1980).
Reynolds et al., Nature Biology, 3:326-330 (2004).
Riechman et al., Nature, 332:323-327 (1988).
Ritter et al., Semin. Cancer Biol., 2:401-409 (1991).
Rixutan - Genentech product fact information insert, 2 pages (May 2006).
Rituxan (Rituximab)-IDEC Pharmaceuticals Corp. & Genentech Inc., product information, 2 pgs insert (2004) (facts).
Roos et al., Hematologically Important Mutations: Leukocytes Adhesion Deficiency, Blood Cells, Molecules, and Diseases, 276(6):1000-1004 (2001).
Rothman et al., Molecular Immunology, 26(12):1113-1123 (1989).
Rudikoff et al., Proc. Natl. Adac. Sci., USA, 79:1979-1983 (1982).
Rulicke et al., Experimental Physiology, 85:589-601 (2000).
Ruohola et al., Cancer Research, 61(10):4229-4237 (2001).
Schianova et al., Curr. Pharm. Design, 10:769-784 (2004).
Schimanski et al., World J. Gastroenterol., 14:4721-4724 (2008).
Scott et al., *Cytokine*, 12(7):858-866 (2000).
Seffernick et al., J. Bacteriol. 183(8):2405-2410 (2001).
Shafi et al., PNAS, 97(11):5735-5739 (2000).
Sharp, Genes & Development, 15:485-490 (2001).
Shibuya et al., Biol. Chem., 383:1573-1579 (2002).
Shinoda et al., Glycobiology Journal, 15:1079-1083 (1998).
Shoji-Hosaka et al., Journal of Biochemistry, 140(6):777-783 (2006).
Sigmund, Arteroscler. Throm. Vasc. Biol., 20:1425-1429 (2000).
Sims et al., The Journal of Immunology, 151(4):2296-2308 (1993).
Slevin et al., Int. J of Cancer, 82:412-423 (1999).
Smith et Al., J.of Cell Biology, 158(4):801-815 (2002).
Sondel et al., Cancer Journal from Scientific American, 3(Suppl. 1):S121-S127 (1997).
Sorbera et al., Drugs of the Future, 26(6):527-532 (2001).
Sousa et al., The J. Of Biological Chemistry, 278(9):7624-7629 (2003).
Staudacher et al., Biochemica et Biophysica Acta, 1473:216-236 (1999).
Stein et al., *J. Mol. Evol.*, 50:397-412 (2000).
Stevenson et all., Bioscience Report., 5(12):1071-1077 (1985).
Suzuki et al., International Immunology, 11(4):553-559 (1999).
Suzuki et al., Clinical Cancer Research, 13(6):1875-1882 (2007).
Tachibana et al., In Vitro Cell. and Dev. Biology Animal, 31(4):261-262 (1995).
Takahashi et al., Glycobiology, 10(5):503-510 (2000).
Takeuchi, Igaku no Ayumi (Progress Med. Sci.), 190(5):474-480 (1999).
Tao et al., Journal of Experimental Medicine, 178:661-667 (1993).
Tijsterman et al., Annu. Rev. Genet., 36:489-519 (2002).
Tonetti et al., The Journal of Biological Chemistry, 271(44):27274-27279 (1996).
Treumann et al., J. of Biological Chemistry, 270(11):6088-6099 (1995).
Trubion Pharmaceuticals poster (Apr. 2008).
Tutt et al., The Journal of Immunology, 161:3176-3185 (1998).
Umana et al., Nature Biotechnology, 17:176-180 (1999).
Umana et al, drugdisc.com/2005/brochure.pdf, May 12, 2005 (2005).
Valve et al., Laboratory Investigation, 81(6):815-826 (2001).
Van Den Berg et al., Am. J. of Pathology, 154(6):1685-1691 (1999).
Van Der Kolk et al., Leukemia, 17:1658-1664 (2003).
Wall, Theriogenology, 45:57-68 (1996).
Wall et al., J. Dairy Sci. 80:2213-2224 (1997).
Wang et al., Proc. Natl., Acad. Sci., USA, 102(44):15791-15796 (2005).
Wang et al., Journal of Biological Chemistry, 273(14):8112-8118 (1998).
Wells et al., Inflamm. Res. 48:353-362 (1999).
Wheeler et al., Theriogenology, 56:1345-1369 (2001).
Wild et al., Cells Tissues Organs, 172:161-173 (2002).
Willer et al., Proc. Natl. Acad. Sci., USA, 101(39):14126-14131 (2004).
Witkowski et al., Biochemistry, 38(36):11643-11650 (1999).
Wolf et al., Experimental Physiology, 85(6):615-625 (2000).
Wu et al., J. of Clinical Investigation, 100(5):1059-1070 (1997).
Xia et al., Biochem. J., 293:633-640 (1993).
Yamaguchi et al., Glycobiology, 10(6):637-643 (2000).
Yamaguchi et al., Biochemical & Biophysical Res. Comm., 291:554-559 (2002).
Yamane-Ohnuki et al., Biotechnology & Bioengineering, 87(5):614-622 (2004).
Yanagidani et al., J. of Biochemistry, 121(3):626-632 (1997).
Yanagimachi, Mol. Cell Endocrinol., 187:241-248 (2002).
Yokoi et al., Cancer Research, 65:10371-10380 (2005).
Yoneyama et al., J. Clin. Invest., 102(11):1933-1941 (1998).
Youn et al., Blood, 89(12):4448-4460 (1997).
Yuyama et al., Cancer, 75(6):1273-1280 (1995).
Zeitlin et al., Nature Biotechnology, 16:1361-1364 (1998).
Zettlmeissl et al., J. Biol. Chem., 264(35):21153-21159 (1989).
Zhou et al., Biotechnology and Bioengineering, 55(5):783-792 (1997).
Zhou et al., Cytotechnology, 22(1-3): 239-250 (1996).
Zhou et al.. Genbank Accession No. NP 058589, J. Biol. Chem., 281(50):38343-38350 (2006).
Zhou et al., Genbank Accession No. NM 016893, J. Biol., Chem., 281(50):38343-38350 (2006).
Zhou et al., Nucleic Acids Research, 30(7):1664-1669 (2002).
Restriction Requirement issued Apr. 28, 2004 in U.S. Appl. No. 09/958,307.
Response to Restriction Requirement filed May 26, 2004 in U.S. Appl. No. 09/958,307.
Non-Final OA issued Jun. 16, 2004 in U.S. Appl. No. 09/958,307.
1.111 Amendment filed Nov. 22, 2004 in U.S. Appl. No. 09/958,307.
Supplemental 1.111 Amendment filed Dec. 14, 2004 in U.S. Appl. No. 09/958,307.
Final OA issued Mar. 1, 2005 in U.S. Appl. No. 09/958,307.
1.116 Amendment filed May 2, 2005 in U.S. Appl. No. 09/958,307.
Supplemental 1.116 Amendment filed May 11, 2005 in U.S. Appl. No. 09/958,307.
Advisory Action issued May 12, 2005 in U.S. Appl. No. 09/958,307.
Advisory Action issued May 23, 2005 in U.S. Appl. No. 09/958,307.
Restriction Requirement issued Jan. 27, 2006 in U.S. Appl. No. 11/126,176.
Response to Restriction Requirement and Preliminary Amendment filed Mar. 27, 2006 in U.S. Appl. No. 11/126,176.
Non-Final OA issued May 19, 2006 in U.S. Appl. No. 11/126,176.
1.111 Amendment filed Aug. 21, 2006 in U.S. Appl. No. 11/126,176.
Final OA issued Nov. 15, 2006 in U.S. Appl. No. 11/126,176.

1.116 Amendment filed Nov. 21, 2006 in U.S. Appl. No. 11/126,176.
Notice of Allowance issued Dec. 28, 2006 in U.S. Appl. No. 11/126,176.
Restriction Requirement issued Jul. 17, 2007 in U.S. Appl. No. 11/126,299.
Response to Restriction Requirement filed Aug. 17, 2007 in U.S. Appl. No. 11/126,299.
Non-Final OA issued Nov. 1, 2007 in U.S. Appl. No. 11/126,299.
1.111 Amendment and Terminal Disclaimer filed Apr. 4, 2008 in U.S. Appl. No. 11/126,299.
Final OA mailed Jul. 8, 2008 in U.S. Appl. No. 11/126,299.
RCE and 1.114 Response filed Dec. 31, 2008 in U.S. Appl. No. 11/126,299.
Non-Final OA issued Apr. 16, 2009 in U.S. Appl. No. 11/126,299.
Notice of Abandonment issued Jun. 30, 2009, in U.S. Appl. No. 11/129,299.
Restriction Requirement issued May 17, 2007 in U.S. Appl. No. 11/126,298.
Response to Restriction Requirement filed Jun. 15, 2007 in U.S. Appl. No. 11/126,298.
Non-Final OA issued Aug. 24, 2007 in U.S. Appl. No. 11/126,298.
1.111 Amendment filed Feb. 22, 2008 in U.S. Appl. No. 11/126,298.
Non-Final OA issued May 15, 2008 in U.S. Appl. No. 11/126,298.
1.111 Amendment filed Aug. 15, 2008 in U.S. Appl. No. 11/126,298.
Final OA issued Nov. 28, 2008 in U.S. Appl. No. 11/126,298.
1.116 Amendment and Terminal Disclaimer filed Feb. 2, 2009 in U.S. Appl. No. 11/126,298.
Advisory Action issued Feb. 27, 2009 in U.S. Appl. No. 11/126,298.
Notice of Allowance issued Mar. 16, 2009 in U.S. Appl. No. 11/126,298.
RCE filed Jun. 16, 2009, in U.S. Appl. No. 11/126,298.
Non-Final OA issued Oct. 1, 2008 in U.S. Appl. No. 11/686,379.
1.111 Amendment and Terminal Disclaimer filed Jan. 2, 2009 in U.S. Appl. No. 11/686,379.
Notice of Allowance issued Apr. 28, 2009 in U.S. Appl. No. 11/686,379.
RCE filed Jul. 18, 2009, in U.S. Appl. No. 11/686,379.
Non-Final OA issued Oct. 1, 2008 in U.S. Appl. No. 11/686,391.
1.111 Amendment and Terminal Disclaimer filed Jan. 2, 2009 in U.S. Appl. No. 11/686,391.
Notice of Allowance issued May 1, 2009 in U.S. Appl. No. 11/686,391.
RCE filed Jul. 18, 2009, in U.S. Appl. No. 11/686,391.
Non-Final OA issued Oct. 2, 2008 in U.S. Appl. No. 11/686,404.
1.111 Amendment and Terminal Disclaimer filed Jan. 2, 2009 in U.S. Appl. No. 11/686,404.
Notice of Allowance issued Feb. 24, 2009 in U.S. Appl. No. 11/686,404.
RCE filed May 25, 2009 in U.S. Appl. No. 11/686,404.
Notice of Allowance issued Jun. 26, 2009, in U.S. Appl. No. 11/686,404.
RCE filed Jul. 18, 2009, in U.S. Appl. No. 11/686,404.
Non-Final OA issued Oct. 1, 2008 in U.S. Appl. No. 11/686,458.
1.111 Amendment and Terminal Disclaimer filed Jan. 2, 2009 in U.S. Appl. No. 11/686,458.
Notice of Allowance issued Feb. 24, 2009 in U.S. Appl. No. 11/686,458.
RCE filed May 25, 2009 in U.S. Appl. No. 11/686,458.
Notice of Allowance issued Jun. 26, 2009 in U.S. Appl. No. 11/686,458.
RCE filed Jul. 19, 2009, in U.S. Appl. No. 11/686,458.
Non-Final OA issued Sep. 30, 2008 in U.S. Appl. No. 11/686,906.
1.111 Amendment and Terminal Disclaimer filed Dec. 30, 2008 in U.S. Appl. No. 11/686,906.
Notice of Allowance issued Feb. 24, 2009 in U.S. Appl. No. 11/686,906.
RCE filed May 25, 2009 in U.S. Appl. No. 11/686,906.
Notice of Allowance issued Jun. 26, 2009 in U.S. Appl. No. 11/686,906.
RCE filed Jul. 20, 2009, in U.S. Appl. No. 11/686,906.
Non-Final OA issued Dec. 10, 2008 in U.S. Appl. No. 11/686,911.
1.111 Amendment and Terminal Disclaimer filed Jun. 10, 2009 in U.S. Appl. No. 11/686,911.
Notice of Allowance issued Jul. 10, 2009 in U.S. Appl. No. 11/686,911.
RCE filed Jul. 17, 2009, in U.S. Appl. No. 11/686,911.
Non-Final OA issued Dec. 10, 2008 in U.S. Appl. No. 11/686,915.
1.111 Amendment and Terminal Disclaimer filed Apr. 10, 2009 in U.S. Appl. No. 11/686,915.
Notice of Allowance issued Jun. 29, 2009, in U.S. Appl. No. 11/686,915.
RCE filed Jul. 19, 2009, in U.S. Appl. No. 11/686,915.
Non-Final OA issued Dec. 10, 2008, in U.S. Appl. No. 11/686,920.
1.111 Amendment and Terminal Disclaimer filed Apr. 10, 2009 in U.S. Appl. No. 11/686,920.
Notice of Allowance issued May 18, 2009 in U.S. Appl. No. 11/686,920.
RCE filed Jul. 18, 2009, in U.S. Appl. No. 11/686,920.
Non-Final OA issued May 19, 2005 in U.S. Appl. No. 10/110,997.
1.111 Amendment filed Nov. 21, 2005 in U.S. Appl. No. 10/110,997.
Non-Final OA issued Feb. 8, 2006 in U.S. Appl. No. 10/110,997.
1.111 Amendment filed Aug. 4, 2006 in U.S. Appl. No. 10/110,997.
Final OA issued Nov. 2, 2006 in U.S. Appl. No. 10/110,997.
1.116 Amendment filed Mar. 1, 2007 in U.S. Appl. No. 10/110,997.
Advisory Action issued Mar. 22, 2007 in U.S. Appl. No. 10/110,997.
RCE filed Apr. 2, 2007 in U.S. Appl. No. 10/110,997.
Final OA issued Jul. 5, 2007 in U.S. Appl. No. 10/110,997.
Non-Final OA issued Sep. 12, 2007 in U.S. Appl. No. 10/110,997.
1.111 Amendment filed Feb. 7, 2008 in U.S. Appl. No. 10/110,997.
Notice of Non-Compliant Amendment issued Jun. 17, 2008 in U.S. Appl. No. 10/110,997.
Response to Notice of Non-Compliant Amendment filed Jul. 9, 2008 in U.S. Appl. No. 10/110,997.
Notice of Allowance issued Nov. 3, 2008 in U.S. Appl. No. 10/110,997.
Restriction Requirement issued Jun. 17, 2003 in U.S. Appl. No. 09/971,773.
Response to Restriction Requirement filed Sep. 17, 2003 in U.S. Appl. No. 09/971,773.
Notice of Non-Responsive Response issued Oct. 7, 2003 in U.S. Appl. No. 09/971,773.
Response to Notice of Non-Response Response filed Dec. 8, 2003 in U.S. Appl. No. 09/971,773.
Non-Final OA issued Feb. 13, 2004 in U.S. Appl. No. 09/971,773.
1.111 Amendment filed Aug. 12, 2004 in U.S. Appl. No. 09/971,773.
Final OA issued Nov. 3, 2004 in U.S. Appl. No. 09/971,773.
1.116 Amendment filed Dec. 17, 2004 in U.S. Appl. No. 09/971,773.
Advisory Action issued Jan. 25, 2005 in U.S. Appl. No. 09/971,773.
1.116 Amendment filed Feb. 2, 2005 in U.S. Appl. No. 09/971,773.
Advisory Action issued Mar. 21, 2005 in U.S. Appl. No. 09/971,773.
Notice of Allowance issued Apr. 5, 2005 in U.S. Appl. No. 09/971,773.
Supplemental Submission under 37 C.F.R. § 1.116 filed Dec. 28, 2004, in U.S. Appl. No. 09/971,773.
Restriction Requirement issued Sep. 22, 2006 in U.S. Appl. No. 11/131,212.
Response to Restriction Requirement filed Oct. 18, 2006 in U.S. Appl. No. 11/131,212.
Non-Final OA issued Jan. 12, 2007 in U.S. Appl. No. 11/131,212.
1.111 Amendment and Terminal Disclaimer filed Jul. 12, 2007 in U.S. Appl. No. 11/131,212.
Non-Final OA issued Sep. 7, 2007 in U.S. Appl. No. 11/131,212.
1.111 Amendment filed Mar. 6, 2008 in U.S. Appl. No. 11/131,212.
Non-Final OA issued Jun. 5, 2008 in in U.S. Appl. No. 11/131,212.
1.111 Amendment and Terminal Disclaimer filed Jul. 29, 2008 in U.S. Appl. No. 11/131,212.
Final OA issued Nov. 24, 2008 in U.S. Appl. No. 11/131,212.
1.116 Amendment and Terminal Disclaimer filed Feb. 24, 2009 in U.S. Appl. No. 11/131,212.
Advisory Action issued Apr. 6, 2009 in U.S. Appl. No. 11/131,212.
RCE, 1.114 Amendment and Terminal Disclaimer filed Apr. 23, 2009 in U.S. Appl. No. 11/131,212.
Non-Final Office Action issued Jul. 9, 2009 in U.S. Appl. No. 11/131,212.
Non-Final OA issued Sep. 11, 2007 in U.S. Appl. No. 11/218,473.
Non-Final OA issued Oct. 18, 2007 in U.S. Appl. No. 11/218,473.

1.111 Amendment filed Apr. 18, 2008 in U.S. Appl. No. 11/218,473.
Final OA issued Jul. 25, 2008 in U.S. Appl. No. 11/218,473.
RCE and 1.114 Response and Terminal Disclaimers filed Nov. 25, 2008 in U.S. Appl. No. 11/218,473.
Non-Final OA issued Mar. 5, 2009 in U.S. Appl. No. 11/218,473.
1.111 Amendment filed Jun. 5, 2009 in U.S. Appl. No. 11/218,473.
Restriction Requirement issued Oct. 31, 2006 in U.S. Appl. No. 11/240,579.
Response to Restriction Requirement and Preliminary Amendment filed Nov. 30, 2006 in U.S. Appl. No. 11/240,579.
Non-Final OA issued Mar. 9, 2007 in U.S. Appl. No. 11/240,579.
Non-Final OA issued May 10, 2007 in U.S. Appl. No. 11/240,579.
1.111 Amendment filed Nov. 13, 2007 in in U.S. Appl. No. 11/240,579.
Final OA issued Feb. 14, 2008 in U.S. Appl. No. 11/240,579.
Notice of Appeal filed Aug. 14, 2008 in U.S. Appl. No. 11/240,579.
RCE and 1.114 Amendment filed Oct. 14, 2008 in U.S. Appl. No. 11/240,579.
Non-Final OA issued Jan. 7, 2009 in U.S. Appl. No. 11/240,579.
1.111 Amendment filed Apr. 7, 2009 in U.S. Appl. No. 11/240,579.
Final Office Action issued Jul. 24, 2009, in U.S. Appl. No. 11/240,579.
Restriction Requirement issued Dec. 5, 2006 in U.S. Appl. No. 11/287,324.
Response to Restriction Requirement filed Jan. 3, 2007 in U.S. Appl. No. 11/287,324.
Non-Final OA issued Mar. 22, 2007 in U.S. Appl. No. 11/287,324.
1.111 Amendment filed Sep. 24, 2007 in U.S. Appl. No. 11/287,324.
Notice of Allowance issued Jan. 7, 2008 in U.S. Appl. No. 11/287,324.
Restriction Requirement issued Dec. 5, 2006 in U.S. Appl. No. 11/287,359.
Response to Restriction Requirement filed Jan. 3, 2007 in U.S. Appl. No. 11/287,359.
Non-Final OA issued Mar. 22, 2007 in U.S. Appl. No. 11/287,359.
Non-Final OA issued Apr. 19, 2007 in U.S. Appl. No. 11/287,359.
1.111 Amendment and Terminal Disclaimer filed Jul. 19, 2007 in U.S. Appl. No. 11/287,359.
Final OA issued Oct. 3, 2007 in U.S. Appl. No. 11/287,359.
1.116 Amendment filed Feb. 22, 2008 in U.S. Appl. No. 11/287,359.
Supplemental 1.116 Amendment filed Mar. 3, 2008 in U.S. Appl. No. 11/287,359.
Advisory Action issued Mar. 17, 2008 in U.S. Appl. No. 11/287,359.
Supplemental 1.116 Response and Terminal Disclaimer filed Mar. 25, 2008 in U.S. Appl. No. 11/287,359.
Notice of Appeal filed Apr. 3, 2008 in U.S. Appl. No. 11/287,359.
Notice of Allowance issued May 2, 2008 in U.S. Appl. No. 11/287,359.
Non-Final OA issued Sep. 17, 2007 in U.S. Appl. No. 11/279,748.
Non-Final OA issued Oct. 18, 2007 in U.S. Appl. No. 11/279,748.
1.111 Amendment (with Terminal Disclaimers) filed Mar. 18, 2008 in U.S. Appl. No. 11/279,748.
Election of Species Requirement issued Jun. 13, 2008 in U.S. Appl. No. 11/279,748.
Response to Election of Species filed Jul. 14, 2008 in U.S. Appl. No. 11/279,748.
Final Office Action issued Sep. 30, 2008 in U.S. Appl. No. 11/279,748.
1.116 Amendment (with Terminal Disclaimer) filed Dec. 29, 2008 in U.S. Appl. No. 11/279,748.
Advisory Action issued Feb. 11, 2009 in U.S. Appl. No. 11/279,748.
Request for Continued Examination filed Feb. 27, 2009, in U.S. Appl. No. 11/279,748.
Non-Final Office Action issued May 28, 2009, in U.S. Appl. No. 11/279,748.
Restriction Requirement issued Apr. 21, 2004 in U.S. Appl. No. 10/327,663.
Response to Restriction Requirement and Preliminary Amendment filed May 21, 2004 in U.S. Appl. No. 10/327,663.
Restriction Requirement issued Jul. 29, 2004 in U.S. Appl. No. 10/327,663.
Response to Restriction Requirement filed Aug. 27, 2004 in U.S. Appl. No. 10/327,663.
Non-Final OA issued Nov. 9, 2004 in U.S. Appl. No. 10/327,663.
1.111 Amendment filed Feb. 3, 2005 in U.S. Appl. No. 10/327,663.
Non-Final OA issued Apr. 7, 2005 in U.S. Appl. No. 10/327,663.
Restriction Requirement issued Feb. 10, 2006, in U.S. Appl. No. 10/409,616.
Response to Restriction Requirement filed Apr. 10, 2006, in U.S. Appl. No. 10/409,616.
Non-Final Office Action issued Jun. 14, 2006, in U.S. Appl. No. 10/409,616.
1.111 Amendment (with IDS) filed Nov. 14, 2006, in U.S. Appl. No. 10/409,616.
Final Office Action issued Sep. 17, 2007, in U.S. Appl. No. 10/409,616.
1.116 Amendment filed Feb. 21, 2008, in U.S. Appl. No. 10/409,616.
Advisory Action issued Mar. 17, 2008, in U.S. Appl. No. 10/409,616.
Notice of Appeal filed Mar. 17, 2008, in U.S. Appl. No. 10/409,616.
Request for Continued Examination (with 1.114c Amendment) filed Apr. 4, 2008, in U.S. Appl. No. 10/409,616.
Notice of Non-Compliant Amendment issued Jul. 10, 2008, in U.S. Appl. No. 10/409,616.
Response to Notice of Non-Compliant Amendment filed Aug. 1, 2008, in U.S. Appl. No. 10/409,616.
Non-Final Office Action issued Jan. 23, 2009, in U.S. Appl. No. 10/409,616.
Restriction Requirement issued Jul. 26, 2004, in U.S. Appl. No. 10/409,609.
Response to Restriction Requirement filed Sep. 27, 2004, in U.S. Appl. No. 10/409,609.
Non-Final Office Action issued Nov. 18, 2004, in U.S. Appl. No. 10/409,609.
Notice of Abandonment issued Sep. 6, 2005, in U.S. Appl. No. 10/409,609.
Restriction Requirement issued Nov. 16, 2006, in U.S. Appl. No. 11/127,173.
Response to Restriction Requirement filed Dec. 13, 2006, in U.S. Appl. No. 11/127,173.
Non-Final Office Action issued Mar. 9, 2007, in U.S. Appl. No. 11/127,173.
1.111 Amendment filed Sep. 10, 2007, in U.S. Appl. No. 11/127,173.
Non-Final Office Action issued Dec. 4, 2007, in U.S. Appl. No. 11/127,173.
Non-Final Office Action issued May 22, 2008, in U.S. Appl. No. 11/127,173.
1.111 Amendment filed Aug. 22, 2008, in U.S. Appl. No. 11/127,173.
Restriction Requirement issued Nov. 26, 2008, in U.S. Appl. No. 11/127,173.
Response to Restriction Requirement issued Dec. 29, 2008, in U.S. Appl. No. 11/127,173.
Final Office Action issued Mar. 19, 2009, in U.S. Appl. No. 11/127,173.
Restriction Requirement issued Sep. 7, 2005, in U.S. Appl. No. 10/409,600.
Response to Restriction Requirement filed Oct. 6, 2005, in U.S. Appl. No. 10/409,600.
Notice of Non-Compliant Amendment issued Dec. 12, 2005, in U.S. Appl. No. 10/409,600.
Response to Notice of Non-Compliant Amendment filed Jan. 9, 2006, in U.S. Appl. No. 10/409,600.
Non-Final Office Action issued Mar. 6, 2006, in U.S. Appl. No. 10/409,600.
1.111 Amendment (with Declaration and IDS) filed Sep. 6, 2006, in U.S. Appl. No. 10/409,600.
Final Office Action issued Nov. 27, 2006, in U.S. Appl. No. 10/409,600.
1.116 Amendment (with Declaration) filed Apr. 27, 2007, in U.S. Appl. No. 10/409,600.
Non-Final Office Action issued May 30, 2007, in U.S. Appl. No. 10/409,600.
1.111 Amendment filed Nov. 30, 2007, in U.S. Appl. No. 10/409,600.
Restriction Requirement issued Apr. 30, 2008, in U.S. Appl. No. 10/409,600.
Response to Restriction Requirement and 1.111 Amendment filed May 30, 2008, in U.S. Appl. No. 10/409,600.

Notice of Non-Complaint Amendment mailed Jun. 6, 2008, in U.S. Appl. No. 10/409,600.
Response to Notice of Non-Complaint Amendment and Supplemental 1.111 Amendment filed Jun. 16, 2008, in U.S. Appl. No. 10/409,600.
Non-Final Office Action issued Jan. 6, 2009, in U.S. Appl. No. 10/409,600.
1.111 Amendment filed Apr. 6, 2009, in U.S. Appl. No. 10/409,600.
Final Office Action issued Jun. 22, 2009, in U.S. Appl. No. 10/409,600.
Restriction Requirement issued Jul. 13, 2005, in U.S. Appl. No. 10/409,611.
Response to Restriction Requirement filed Aug. 11, 2005, in U.S. Appl. No. 10/409,611.
Non-Final Office Action issued Oct. 12, 2005, in U.S. Appl. No. 10/409,611.
1.111 Amendment (with Declaration and IDS) filed Apr. 11, 2006, in U.S. Appl. No. 10/409,611.
Final Office Action issued Jun. 14, 2006, in U.S. Appl. No. 10/409,611.
Notice of Appeal filed Dec. 14, 2006, in U.S. Appl. No. 10/409,611.
Notice of Abandonment issued Jul. 12, 2007, in U.S. Appl. No. 10/409,611.
Request to Withdraw Abandonment, Request for Continued Examination, 116, Amendment and Information Disclosure Statement filed Jul. 13, 2007, in U.S. Appl. No. 10/409,611.
Communication, Withdrawal of Abandonment issued Jul. 24, 2007, in U.S. Appl. No. 10/409,611.
Decision on Petition issued Dec. 14, 2007, in U.S. Appl. No. 10/409,611.
Non-Final Office Action issued Apr. 21, 2008, in U.S. Appl. No. 10/409,611.
Decision on Petition issued Jul. 9, 2008, in U.S. Appl. No. 10/409,611.
1.111 Amendment filed Jul. 21, 2008, in U.S. Appl. No. 10/409,611.
Supplemental Submission filed Aug. 6, 2008, in U.S. Appl. No. 10/409,611.
Notice of Non-Complaint Amendment issued Nov. 14, 2008, in U.S. Appl. No. 10/409,611.
Response to Notice of Non-Compliant Amendment filed Dec. 15, 2008, in U.S. Appl. No. 10/409,611.
Final Office Action issued Apr. 13, 2009, in U.S. Appl. No. 10/409,611.
Restriction Requirement issued Aug. 22, 2005, in U.S. Appl. No. 10/409,608.
Amendment (Response to Restriction Requirement) filed Nov. 22, 2005, in U.S. Appl. No. 10/409,608..
Restriction Requirement issued Feb. 6, 2006, in U.S. Appl. No. 10/409,608.
Response to Restriction Requirement filed Mar. 27, 2006, in U.S. Appl. No. 10/409,608.
Non-Final Office Action issued May 31, 2006, in U.S. Appl. No. 10/409,608.
1.111 Amendment (with Sequence Listing and IDS) filed Nov. 30, 2006, in U.S. Appl. No. 10/409,608.
Final Office Action issued Feb. 22, 2007, in U.S. Appl. No. 10/409,608.
Notice of Appeal filed Aug. 22, 2007, in U.S. Appl. No. 10/409,608.
Request for Continued Examination and 1.114(c) Amendment filed Mar. 19, 2008, in U.S. Appl. No. 10/409,608.
Non-Final Office Action issued Jun. 6, 2008, in U.S. Appl. No. 10/409,608.
1.111 Amendment filed Sep. 26, 2008, in U.S. Appl. No. 10/409,608.
Final Office Action issued Dec. 31, 2008, in U.S. Appl. No. 10/409,608.
1.116 Amendment filed May 29, 2009, in U.S. Appl. No. 10/409,608.
Advisory Action issued Jun. 3, 2009, in U.S. Appl. No. 10/409,608.
RCE and Terminal Disclaimer filed Jun. 19, 2009, in U.S. Appl. No. 10/409,608.
Non-Final OA issued Oct. 12, 2006 in U.S. Appl. No. 10/803,100.
Non-Final OA issued Apr. 30, 2008 in U.S. Appl. No. 11/783,487.
Non-Final OA issued May 12, 2009 in U.S. Appl. No. 12/261,997.
Restriction Requirement issued Feb. 3, 2009 in U.S. Appl. No. 10/575,261.
Response to Restriction Requirement filed Mar. 3, 2009 in U.S. Appl. No. 10/575,261.
Election of Species Requirement issued May 26, 2009 in U.S. Appl. No. 10/575,261.
Response to Election of Species Requirement and Preliminary Amendment filed Jun. 25, 2009 in U.S. Appl. No. 10/575,261.
Restriction Requirement issued Jun. 20, 2006 in U.S. Appl. No. 10/959,326.
Response to Restriction Requirement filed Jul. 20, 2006 in U.S. Appl. No. 10/959,326.
Supplemental Response to Restriction Requirement and Preliminary Amendment filed Aug. 21, 2006 in U.S. Appl. No. 10/959,326.
Non-Final OA issued Oct. 5, 2006 in U.S. Appl. No. 10/959,326.
Restriction Requirement issued Apr. 8, 2008 in U.S. Appl. No. 11/730,992.
Restriction Requirement issued Oct. 23, 2006 in Ussn 10/959,310.
Response to Restriction Requirement filed Apr. 23, 2007 in U.S. Appl. No. 10/959,310.
Non-Final OA issued Jul. 6, 2007 in U.S. Appl. No. 10/959,310.
Restriction Requirement issued Sep. 14, 2006 in U.S. Appl. No. 10/959,322.
Response to Restriction Requirement filed Oct. 18, 2006 in U.S. Appl. No. 10/959,322.
Non-Final OA issued Mar. 21, 2007 in U.S. Appl. No. 10/959,322.
1.111 Amendment filed Sep. 19, 2007 in U.S. Appl. No. 10/959,322.
Final OA issued Apr. 28, 2008 in U.S. Appl. No. 10/959,322.
1.116 Amendment filed Aug. 28, 2008 in U.S. Appl. No. 10/959,322.
Advisory Action issued Sep. 19, 2008 in U.S. Appl. No. 10/959,322.
RCE and 1.114 Amendment filed Oct. 16, 2008 in U.S. Appl. No. 10/959,322.
Non-Final OA issued Dec. 5, 2008 in U.S. Appl. No. 10/959,322.
1.111 Response filed Apr. 2, 2009 in U.S. Appl. No. 10/959,322.
Notice of Allowance issued Jul. 23, 2009, in U.S. Appl. No. 10/959,322.
Restriction Requirement issued Feb. 28, 2007 in U.S. Appl. No. 10/959,309.
Response to Restriction Requirement filed Apr. 2, 2007 in U.S. Appl. No. 10/959,309.
Non-Final OA issued Jun. 14, 2007 in U.S. Appl. No. 10/959,309.
1.111 Amendment filed Dec. 14, 2007 in U.S. Appl. No. 10/959,309.
Final OA issued Apr. 2, 2008 in U.S. Appl. No. 10/959,309.
1.116 Amendment filed Aug. 1, 2008 in U.S. Appl. No. 10/959,309.
Advisory Action issued Aug. 14, 2008 in U.S. Appl. No. 10/959,309.
RCE filed Sep. 2, 2008 in U.S. Appl. No. 10/959,309.
Non-Final OA issued Oct. 10, 2008 in U.S. Appl. No. 10/959,309.
Restriction Requirement issued Jun. 26, 2008 in U.S. Appl. No. 10/575,253.
Response to Restriction Requirement filed Sep. 26, 2008 in U.S. Appl. No. 10/575,253.
Non-Final OA issued Jan. 13, 2009 in U.S. Appl. No. 10/575,253.
Restriction Requirement issued Apr. 1, 2009 in U.S. Appl. No. 10/575,096.
Response to Restriction requirement filed May 29, 2009 in U.S. Appl. No. 10/575,096.
Restriction Requirement issued Jun. 12, 2009 in U.S. Appl. No. 10/575,096.
Restriction Requirement issued Jun. 12, 2007 in U.S. Appl. No.11/196,503.
Response to Restriction Requirement filed Jul. 12, 2007 in U.S. Appl. No. 11/196,503.
Supplemental Response to Restriction Requirement filed Sep. 6, 2007 in U.S. Appl. No. 11/196,503.
Non-Final OA issued Nov. 13, 2007 in U.S. Appl. No. 11/196,503.
1.111 Amendment filed Feb. 21, 2008 in U.S. Appl. No. 11/196,503.
Final OA issued May 7, 2008 in U.S. Appl. No. 11/196,503.
1.116 Amendment filed Jul. 28, 2008 in U.S. Appl. No. 11/196,503.
Advisory Action issued Aug. 15, 2008 in U.S. Appl. No. 11/196,503.
RCE and 1.114 Amendment filed Sep. 5, 2008 in U.S. Appl. No. 11/196,503.
Non-Final OA issued Oct. 10, 2008 in U.S. Appl. No. 11/196,503.

1.111 Response and Terminal Disclaimer filed Mar. 10, 2009 in U.S. Appl. No. 11/196,503.
Final Office Action issued Jun. 22, 2009, in U.S. Appl. No. 11/196,503.
Restriction Requirement issued Sep. 11, 2007 in U.S. Appl. No. 11/491,501.
Response to Restriction Requirement filed Oct. 11, 2007 in U.S. Appl. No. 11/491,501.
Non-Final Office Action issued Feb. 6, 2008 in U.S. Appl. No. 11/491,501.
1.111 Amendment filed Jul. 7, 2008 in U.S. Appl. No. 11/491,501.
Notice to Comply issued Oct. 28, 2008 in U.S. Appl. No. 11/491,501.
Response to Notice to Comply filed Nov. 13, 2008 in U.S. Appl. No. 11/491,501.
Notice to Comply issued Feb. 25, 2009 in U.S. Appl. No. 11/491,501.
Response to Notice to Comply filed Mar. 18, 2009 in U.S. Appl. No. 11/491,501.
Restriction Requirement issued Jun. 14, 2002 in U.S. Appl. No. 09/796,744.
Response to Restriction Requirement filed Jul. 15, 2002 in U.S. Appl. No. 09/796,744.
Non-Final OA issued Oct. 16, 2002 in U.S. Appl. No. 09/796,744.
1.111 Amendment filed Mar. 17, 2003 in U.S. Appl. No. 09/796,744.
Non-Final OA issued Jun. 2, 2003 in U.S. Appl. No. 09/796,744.
1.111 Amendment and 1.132 Declaration filed Dec. 2, 2003 in U.S. Appl. No. 09/796,744.
Final OA issued Feb. 25, 2004 in U.S. Appl. No. 09/796,744.
1.116 Amendment and 1.132 Declaration filed Jul. 26, 2004 in U.S. Appl. No. 09/796,744.
Advisory Action issued Aug. 24, 2004 in U.S. Appl. No. 09/796,744.
Notice of Appeal filed Aug. 25, 2004 in U.S. Appl. No. 09/796,744.
RCE filed Sep. 7, 2004 in U.S. Appl. No. 09/796,744.
Non-Final OA issued Nov. 5, 2004 in U.S. Appl. No. 09/796,744.
1.111 Amendment filed Nov. 30, 2004 in U.S. Appl. No. 09/796,744.
Notice of Allowance issued Feb. 22, 2005 in U.S. Appl. No. 09/796,744.
Restriction Requirement issued Feb. 6, 2007 in U.S. Appl. No. 11/094,718.
Response to Restriction Requirement filed Mar. 16, 2007 in U.S. Appl. No. 11/094,718.
Non-Final OA issued May 30, 2007 in U.S. Appl. No. 11/094,718.
1.111 Amendment filed Oct. 29, 2007 in U.S. Appl. No. 11/094,718.
Final OA issued Dec. 21, 2007 in Ussn 11/094,718.
1.116 Amendment filed May 21, 2008 in U.S. Appl. No. 11/094,718.
Advisory Action issued Jun. 13, 2008 in U.S. Appl. No. 11/094,718.
RCE filed Jun. 20, 2008 in U.S. Appl. No. 11/094,718.
Non-Final OA issued Sep. 16, 2008 in U.S. Appl. No. 11/094,718.
1.111 Amendment filed Dec. 16, 2008 in U.S. Appl. No. 11/094,718.
Final OA issued Mar. 13, 2009 in U.S. Appl. No. 11/094,718.
1.116 Amendment filed Jun. 15, 2009 in U.S. Appl. No. 11/094,718.
Advisory Action issued Jun. 24, 2009 in U.S. Appl. No. 11/094,718.
RCE filed Jul. 13, 2009 in U.S. Appl. No. 11/094,718.
Restriction Requirement issued Jul. 12, 2005 in U.S. Appl. No. 10/231,452.
Response to Restriction Requirement filed Aug. 12, 2005 in U.S. Appl. No. 10/231,452.
Notice of Non-Compliant Response issued Sep. 28, 2005 in U.S. Appl. No. 10/231,452.
Response to Notice of Non-Compliant Response filed Oct. 25, 2005 in U.S. Appl. No. 10/231,452.
Non-Final OA issued Jan. 10, 2006 in U.S. Appl. No. 10/231,452.
1.111 Amendment filed Jul. 13, 2006 in U.S. Appl. No. 10/231,452.
Final OA issued Sep. 21, 2006 in U.S. Appl. No. 10/231,452.
Notice of Appeal filed Mar. 21, 2007 in U.S. Appl. No. 10/231,452.
1.116 Amendment and Terminal Disclaimer filed Apr. 5, 2007 in U.S. Appl. No. 10/231,452.
Advisory Action issued Apr. 24, 2007 in U.S. Appl. No. 10/231,452.
RCE filed May 21, 2007 in U.S. Appl. No. 10/231,452.
Non-Final OA issued Jul. 31, 2007 in U.S. Appl. No. 10/231,452.
Petition to Withdraw Terminal Disclaimer of Apr. 5, 2007 filed Oct. 31, 2007 in U.S. Appl. No. 10/231,452.
1.111 Amendment filed Nov. 30, 2007 in U.S. Appl. No. 10/231,452.
Decision on Petition issued on Jan. 3, 2008 in U.S. Appl. No. 10/231,452.
Final OA issued Feb. 20, 2008 in U.S. Appl. No. 10/231,452.
1.116 Amendment filed Jun. 20, 2008 in U.S. Appl. No. 10/231,452.
Advisory Action issued Aug. 5, 2008 in U.S. Appl. No. 10/231,452.
RCE and 1.114 Amendment filed Aug. 20, 2008 in U.S. Appl. No. 10/231,452.
Notice of Allowance issued Nov. 10, 2008 in U.S. Appl. No. 10/231,452.
Restriction Requirement issued Jan. 19, 2007 in U.S. Appl. No. 11/144,731.
Response to Restriction Requirement filed Feb. 12, 2007 in U.S. Appl. No. 11/144,731.
Non-Final OA issued Mar. 19, 2007 in U.S. Appl. No. 11/144,731.
1.111 Amendment filed Sep. 5, 2007 in U.S. Appl. No. 11/144,731.
Final OA issued Nov. 13, 2007 in U.S. Appl. No. 11/144,731.
RCE and 1.114 Amendment filed May 8, 2008 in U.S. Appl. No. 11/144,731.
Final OA issued May 29, 2008 in U.S. Appl. No. 11/144,731.
1.116 Amendment filed Sep. 29, 2008 in U.S. Appl. No. 11/144,731.
Advisory Action issued Oct. 15, 2008 in U.S. Appl. No. 11/144,731.
Pre-Appeal Brief Request for Review and Notice of Appeal filed Dec. 1, 2008 in U.S. Appl. No. 11/144,731.
Notice of Panel Decision issued Jan. 13, 2009 in U.S. Appl. No. 11/144,731.
RCE filed Feb. 13, 2009 in U.S. Appl. No. 11/144,731.
Notice of Non-Response Amendment issued Jun. 4, 2009 in U.S. Appl. No. 11/144,731.
Restriction Requirement issued Jul. 13, 2007 in U.S. Appl. No. 10/581,413.
Response to Restriction Requirement filed Aug. 27, 2007 in U.S. Appl. No. 10/581,413.
Non-Final OA issued Oct. 17, 2007 in U.S. Appl. No. 10/581,413.
1.111 Amendment filed Apr. 17, 2008 in U.S. Appl. No. 10/581,413.
Restriction Requirement issued Jul. 28, 2008 in U.S. Appl. No. 10/581,413.
Response to Restriction Requirement filed Aug. 28, 2008 in U.S. Appl. No. 10/581,413.
Final OA issued Dec. 11, 2008 in U.S. Appl. No. 10/581,413.
1.116 Amendment and Statement of Availability filed Apr. 13, 2009 in U.S. Appl. No. 10/581,413.
Advisory Action issued Apr. 27, 2009 in U.S. Appl. No. 10/581,413.
RCE filed May 11, 2009 in U.S. Appl. No. 10/581,413.
Non-Final Office Action issued Jul. 22, 2009, in U.S. Appl. No. 10/581,413.
Restriction Requirement issued Apr. 25, 2008 in U.S. Appl. No. 10/574,016.
Response to Restriction Requirement filed May 27, 2008 in U.S. Appl. No. 10/574,016.
Non-Final OA issued Aug. 4, 2008 in U.S. Appl. No. 10/574,016.
1.111 Amendment filed Nov. 4, 2008 in U.S. Appl. No. 10/574,016.
Non-Final OA issued Jan. 30, 2009 in U.S. Appl. No. 10/574,016.
1.111 Amendment and Rule 1.132 Declaration filed May 29, 2009 in U.S. Appl. No. 10/574,016.
Restriction Requirement issued Mar. 27, 2009 in U.S. Appl. No. 12/019,160.
Response to Restriction Requirement filed Apr. 27, 2009 in U.S. Appl. No. 12/019,160.
Non-Final Office Action issued Jun. 24, 2009, in U.S. Appl. No. 12/019,160.
Restriction Requirement issued Jul. 12, 2009, in U.S. Appl. No. 10/575,114.
European Communication issued Jul. 21, 2009, in EP 1176195.
R. Bruce Simonson et al., "Inhibition of Mannosidase in Hybridomas Yields Monoclonal Antibodies with Greater Capacity for Carbohydrate Labeling", Clinical Chemistry, 1968, 34(9):1713-1716.
Observation Letter dated Jul. 8, 2009 in EP 1173195.

* cited by examiner

FIG. 3
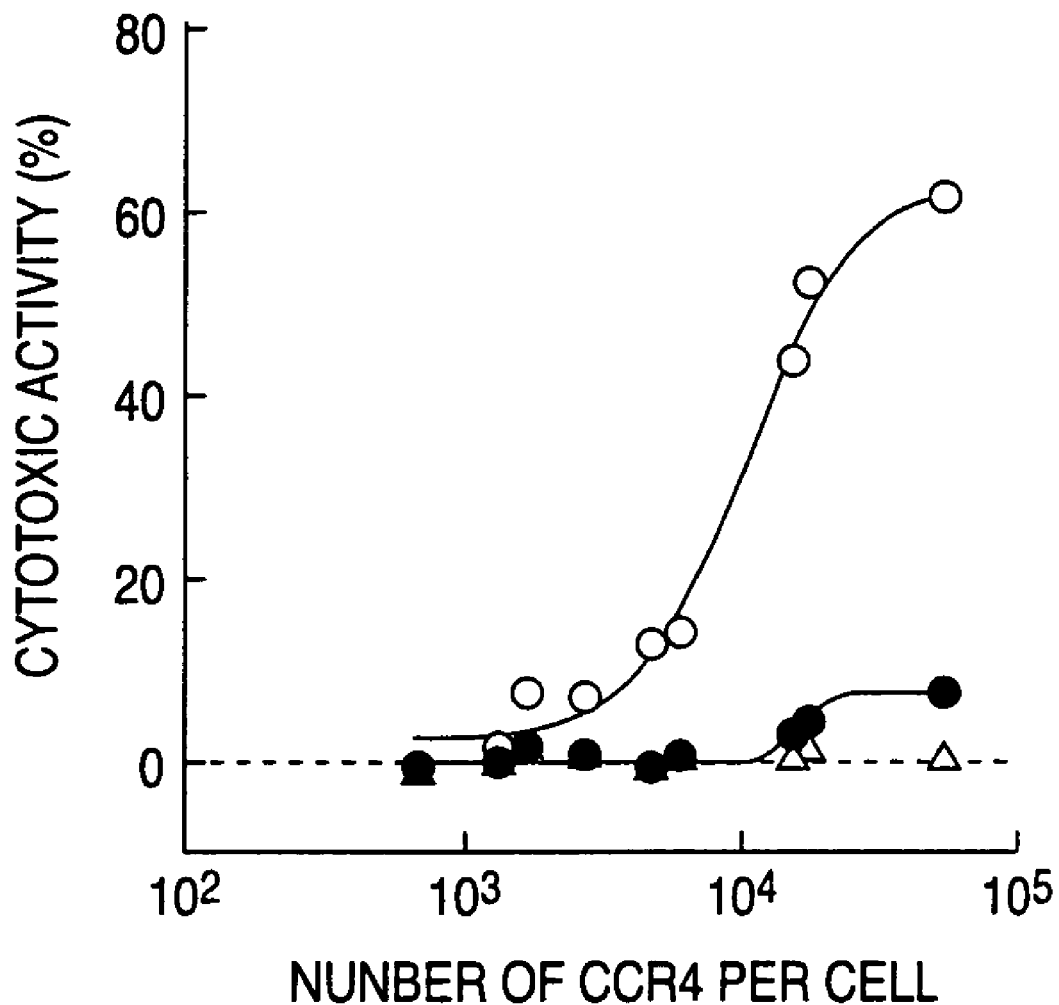
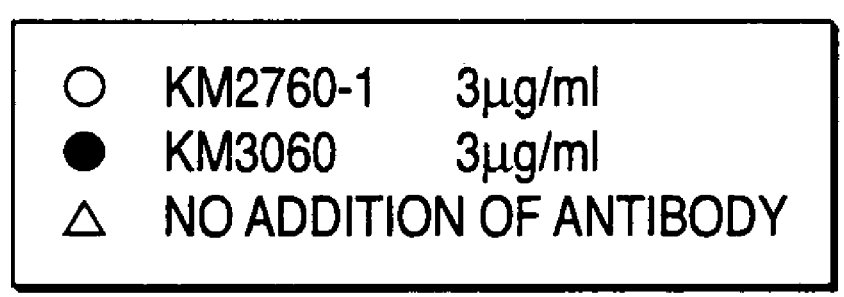

ANTIBODY COMPOSITION-CONTAINING MEDICAMENT

The present application claims benefit of JP 2002-106949, filed 9 Apr. 2002, the entire contents of which is incorporated herein by reference.

BACKGROUND OF THE INVENTION

1. Field of the Invention

The present invention relates to a medicament for treating a patient who cannot be cured with a medicament comprising as an active ingredient an antibody composition produced by a cell unresistant to a lectin which recognizes a sugar chain in which 1-position of fucose is bound to 6-position of N-acetylglucosamine in the reducing end through α-bond in a complex N-glycoside-linked sugar chain, and a method for screening the patient by using the medicament.

2. Brief Description of the Background Art

Since antibodies have high binding activity, binding specificity and high stability in blood, their applications to diagnosis, prevention and treatment of various human diseases have been attempted [*Monoclonal Antibodies: Principles and Applications*, Wiley-Liss, Inc., Chapter 2.1 (1995)]. Also, production of a humanized antibody such as a human chimeric antibody or a human complementarity determining region (hereinafter referred to as "CDR")-grafted antibody from a non-human animal antibody have been attempted by using genetic recombination techniques. The human chimeric antibody is an antibody in which its antibody variable region (hereinafter referred to as "V region") is derived from a non-human animal antibody and its constant region (hereinafter referred to as "C region") is derived from a human antibody. The human CDR-grafted antibody is an antibody in which the CDR of a human antibody is replaced by CDR derived from a non-human animal antibody.

It has been found that five classes, IgM, IgD, IgG, IgA and IgE, are present in mammal antibodies. Antibodies of human IgG class are mainly used for the diagnosis, prevention and treatment of various human diseases because they have functional characteristics such as long half-life in blood and various effector functions [Monoclonal Antibodies: Principles and Applications, Wiley-Liss, Inc., Chapter 1 (1995)]. The human IgG class antibody is further classified into the following 4 subclasses: IgG1, IgG2, IgG3 and IgG4. A large number of studies have so far been conducted for antibody-dependent cell-mediated cytotoxic activity (hereinafter referred to as "ADCC activity") and complement-dependent cytotoxic activity (hereinafter referred to as "CDC activity") as effector functions of the IgG class antibody, and it has been reported that among antibodies of the human IgG class, the IgG1 subclass has the highest ADCC activity and CDC activity [Chemical Immunology, 65, 88 (1997)]. In view of the above, most of the anti-tumor humanized antibodies, including commercially available an anti-CD20 antibody RITUXAN (Rituximab) (manufactured by IDEC/Genentech) and an anti-HER2 antibody HERCEPTIN (manufactured by Roche/Genentech), which require high effector functions for the expression of their effects, are antibodies of the human IgG1 subclass.

Also, ills known that the degrees of ADCC activity and CDC activity show a positive correlation to the expressed amount of antigens on target cells [J. Immunol., 116, 253 (1976), J. Natl. Cancer Inst., 72, 673 (1984), J. Nucl. Med., 27, 422 (1986), Cancer Res., 48, 6303 (1988), British J. Cancer, 78, 478 (1998)]. Also, it has been proved by examinations using Herceptin that commercially available therapeutic antibodies do not show their therapeutic effects unless an antigen amount at a certain degree is present on target cells.

That is, as a result of analysis on the correlation between the ADCC activity of HERCEPTIN and the expressed amount of HER2 antigen on target cancer cells, it was shown that the ADCC activity is hardly induced when the number of HER2 on the target cell is at the level of $10^4$, that significant ADCC activity is induced when the number of HER2 on the target cell is at the level of $10^5$ or more, and that high ADCC activity is induced when the number of HER2 on the target cell is at the level of about $10^6$. For example, HERCEPTIN shows high ADCC activity upon a human breast cancer cell line SK-BR-3 expressing $9.0 \times 10^5$ of BER2 molecules, but HERCEPTIN did not exert ADCC activity upon a human breast cancer cell line MCF7 expressing $2.2 \times 10^4$ of HER2 molecules [Cancer Immunol. Immunother., 37, 255 (1993), HERCEPTIN injection 150 pamphlet, HER.PA.1.2 (June, 2001)].

Also, in clinical tests, it is known that therapeutic effect of HERCEPTIN is significantly high for patients recognized to have high expression of tumor tissue BFR2 by an immunohistochemistry method or a fluorescence in situ hybridization method, rather than for patients having low HER2 expression [Proc. Am. Soci. Clin. Oncol., 20, 22a (2001)]. Thus, since its therapeutic effect is hardly shown for patients having low HER2 expression, application of HERCEPTIN is limited to patients having BER2 over-expression.

In addition to HERCEPTIN, an anti-CD20 antibody RITUXAN, an anti-CD52 antibody CAMPATH and the like are known as therapeutic antibodies. All of these antibodies aim at obtaining their therapeutic effects by destroying target cells, and the ADCC activity is considered to be the major mechanism in each case. The number of antigen molecules on the treatable target cell of these antibodies is 1 to $3 \times 10^5$ in CD20 [J. Olin. Pathol., 51, 364 (1998)] and is also 1 to $5 \times 10^5$ in CD52 [Seminars in Oncology, 26 (5 Suppl 14), 52 (1999)], each requiring $10^5$ or more. Thus, the therapeutic antibodies so far known require that an antigen is expressed at $10^5$ or more on the target cell for the expression of ADCC activity, and no therapeutic agent which uses, as an active ingredient, an antibody for a target cell which expresses an antigen at an amount of less than $10^5$ is known.

SUMMARY OF THE INVENTION

The present invention relates to the following (1) to (21):

(1) A medicament for treating a patient who cannot be cured with a medicament comprising as an active ingredient an antibody composition produced by a cell unresistant to a lectin which recognizes a sugar chain in which 1-position of fucose is bound to 6-position of N-acetylglucosamine in the reducing end through α-bond in a complex N-glycoside-linked sugar chain, which comprises as an active ingredient an antibody composition produced by a cell resistant to a lectin which recognizes a sugar chain in which 1-position of fucose is bound to 6-position of N-acetylglucosamine in the reducing end through α-bond in a complex N-glycoside-linked sugar chain.

(2) The medicament according to (1), wherein the patient who cannot be cured with a medicament comprising as an active ingredient an antibody composition produced by a cell unresistant to a lectin which recognizes a sugar chain in which 1-position of fucose is bound to 6-position of N-acetylglucosamine in the reducing end through α-bond in a complex N-glycoside-linked sugar chain is a patient in which an antigen which is recognized by the antibody composition is expressed in such an amount that the antibody composition cannot exert sufficient therapeutic effect.

(3) The medicament according to (2), wherein the amount that the antibody composition cannot exert sufficient therapeutic effect is such an amount that the antibody composition cannot exert sufficient antibody-dependent cell-mediated cytotoxic activity.

(4) A medicament for treating a disease which cannot be cured with a medicament comprising as an active ingredient an antibody composition produced by a cell unresistant to a lectin which recognizes a sugar chain in which 1-position of fucose is bound to 6-position of N-acetylglucosamine in the reducing end through α-bond in a complex N-glycoside-linked sugar chain, which comprises as an active ingredient an antibody composition produced by a cell resistant to a lectin which recognizes a sugar chain in which 1-position of fucose is bound to 6-position of N-acetylglucosamine in the reducing end through α-bond in a complex N-glycoside-linked sugar chain.

(5) The medicament according to (4), wherein the disease which cannot be cured with a medicament comprising as an active ingredient an antibody composition produced by a cell unresistant to a lectin which recognizes a sugar chain in which 1-position of fucose is bound to 6-position of N-acetylglucosamine in the reducing end through α-bond in a complex N-glycoside-linked sugar chain is a disease in which an antigen which is recognized by the antibody composition in a target cell relating to the disease is expressed in such an amount that the antibody composition cannot exert sufficient therapeutic effect.

(6) The medicament according to (5), wherein the amount that the antibody composition cannot exert sufficient therapeutic effect is such an amount that the antibody composition cannot exert a sufficient antibody-dependent cell-mediated cytotoxic activity.

(7) The medicament according to any one of (1) to (6), wherein the cell resistant to a lectin is a cell having a protein selected from the group consisting of the following (a), (b) and (c):
  (a) an enzyme protein relating to synthesis of an intracellular sugar nucleotide, GDP-fucose;
  (b) an enzyme protein relating to modification of a sugar chain in which 1-position of fucose is bound to 6-position of N-acetylglucosamine in the reducing end through α-bond in a complex N-glycoside-linked sugar chain; and
  (c) a protein relating to transport of an intracellular sugar nucleotide, GDP-fucose to the Golgi body,
    wherein the activity of the protein is decreased or deleted.

(8) The medicament according to any one of (1) to (7), wherein the lectin is at least one lectin selected from the group consisting of the following (a) to (d);
  (a) a *Lens culinaris* lectin;
  (b) a *Pisum sativum* lectin;
  (c) a *Vicia faba* lectin, and
  (d) an *Aleuria auranlia* lectin.

(9) The medicament according to any one of (1) to (8), wherein the cell is selected from the group consisting of a yeast, an animal cell, an insect cell and a plant cell.

(10) The medicament according to any one of (1) to (9), wherein the cell is selected from the group consisting of the following (a) to (j):
  (a) a CHO cell derived from a Chinese hamster ovary tissue;
  (b) a rat myeloma cell line YB2/3HL.P2.G11.16Ag.20 line;
  (c) a mouse myeloma cell line NS0 cell;
  (d) a mouse myeloma cell line SP2/0-Ag14 cell;
  (e) a BHK cell derived from a Syrian hamster kidney tissue;
  (f) a hybridoma cell;
  (g) a human leukemic cell line Namalwa cell;
  (h) an embryonic stem cell;
  (i) a fertilized egg cell; and
  (j) a plant cell.

(11) The medicament according to any one of (1) to (10), wherein the antibody molecule is selected from the group consisting of the following (a) to (d):
  (a) a human antibody;
  (b) a humanized antibody;
  (c) an antibody fragment comprising the Fc region of (a) or (b); and
  (d) a fusion protein comprising the Fc region of (a) or (b).

(12) The medicament according to (11), wherein the antibody molecule belongs to an IgG class.

(13) The medicament according to any one of (1) to (12), wherein the antibody composition produced by a cell resistant to a lectin which recognizes a sugar chain in which 1-position of fucose is bound to 6-position of N-acetylglucosamine in the reducing end through α-bond in a complex N-glycoside-linked sugar chain is an antibody composition having a higher antibody-dependent cell-mediated cytotoxic activity than the antibody composition produced by a cell unresistant to a lectin which recognizes a sugar chain in which 1-position of fucose is bound to 6-position of N-acetylglucosamine in the reducing end through α-bond in a complex N-glycoside-linked sugar chain.

(14) The medicament according to (13), wherein the higher antibody-dependent cell-mediated cytotoxic activity-having antibody composition has complex N-glycoside-linked sugar chains bound to Fc regions included in the antibody compositions, and the ratio of sugar chains in which fucose is not bound to N-acetylglucosamine in its reducing end to the total complex N-glycoside-linked sugar chains is higher than that of the antibody composition produced by a cell unresistant to a lectin which recognized a sugar chain in which 1-position of fucose is bound to 6-position of N-acetylglucosamine in the reducing end through α-bond in a complex N-glycoside-linked sugar chain.

(15) The medicament according to (14), wherein the sugar chain in which fucose is not bound is a complex N-glycoside-linked sugar chain in which 1-position of the fucose is not bound to 6-position of N-acetylglucosamine in the reducing end through α-bond.

(16) The medicament according to any one of (13) to (15), wherein the antibody composition having a higher antibody-dependent cell-mediated cytotoxic activity is an antibody composition wherein the ratio of sugar chains in which fucose is not bound to N-acetylglucosamine in the reducing end to the total complex N-glycoside-linked sugar chains bound to the Fc region in the antibody composition is 20% or more.

(17) The medicament according to (16), wherein the antibody composition in which the ratio of sugar chains in which fucose is not bound to N-acetylglucosamine in the reducing end is 20% or more is an antibody composition produced by a CHO cell.

(18) The medicament according to any one of (1) to (17), which is a diagnostic agent, an preventing agent or a treating agent for tumor-accompanied diseases, allergy-accompanied diseases, inflammatory-accompanied diseases, autoimmune diseases, cardiovascular diseases, viral infection-accompanied diseases or bacterial infection-accompanied diseases.

(19) Use of an antibody composition produced by a cell resistant to a lectin which recognizes a sugar chain in which 1-position of fucose is bound to 6-position of N-acetylglucosamine in the reducing end through α-bond in a complex N-glycoside-linked sugar chain for the manufacture of the medicament according to any one of (1) to (17).

(20) A method for screening a patient to whom the medicament according to any one of (1) to (17) is effective, which comprises (i) contacting a medicament comprising as an active ingredient an antibody composition produced by a cell unresistant to a lectin which recognizes a sugar chain in which 1-position of fucose is bound to 6-position of N-acetylglucosamine in the reducing end through α-bond in a complex N-glycoside-linked sugar chain or the medicament according to any one of (1) to (17), with a target cell for the medicaments obtained from a patient;

(ii) measuring the activity of each of the medicaments reacted with the target cell, (iii) comparing the activity of the medicament comprising as an active ingredient an antibody composition produced by a cell unresistant to a lectin which recognizes a sugar chain in which 1-position of fucose is bound to 6-position of N-acetylglucosamine in the reducing end through α-bond in a complex N-glycoside-linked sugar chain with the activity of the medicament according to any one of (1) to (17); and (iv) selecting a patient in which the activity of the medicament comprising as an active ingredient an antibody composition produced by a cell unresistant to a lectin which recognizes a sugar chain in which 1-position of fucose is bound to 6-position of N-acetylglucosamine in the reducing end through α-bond in a complex N-glycoside-linked sugar chain is lower.

(21) The method according to (20), wherein the method for measuring the activity of the medicament reacted with the target cell is a method selected from the group consisting of (a) to (d):

(a) an antibody-dependent cell-mediated cytotoxic activity;

(b) an Fcγ receptor IIIa binding activity;

(c) a complement-dependent cytotoxic activity; and (d) a growth inhibition activity.

BRIEF DESCRIPTION OF THE DRAWINGS

FIG. 3 shows ADCC activities of KM2760-1 and KM3060 when clones which express CCR4 at various amounts were used as target cells. The ordinate and the abscissa show the cytotoxic activity (%) and the number of CCR4 molecules on the target cell, respectively. "○", "●" and "Δ" show cytotoxic activities in the presence of KM2760-1, in the presence of KM3060 and in the absence of antibody, respectively.

FIG. 4A and FIG. 4B show results of KM2760-1 and KM3060, respectively.

DETAILED DESCRIPTION OF THE INVENTION

Figure 1:
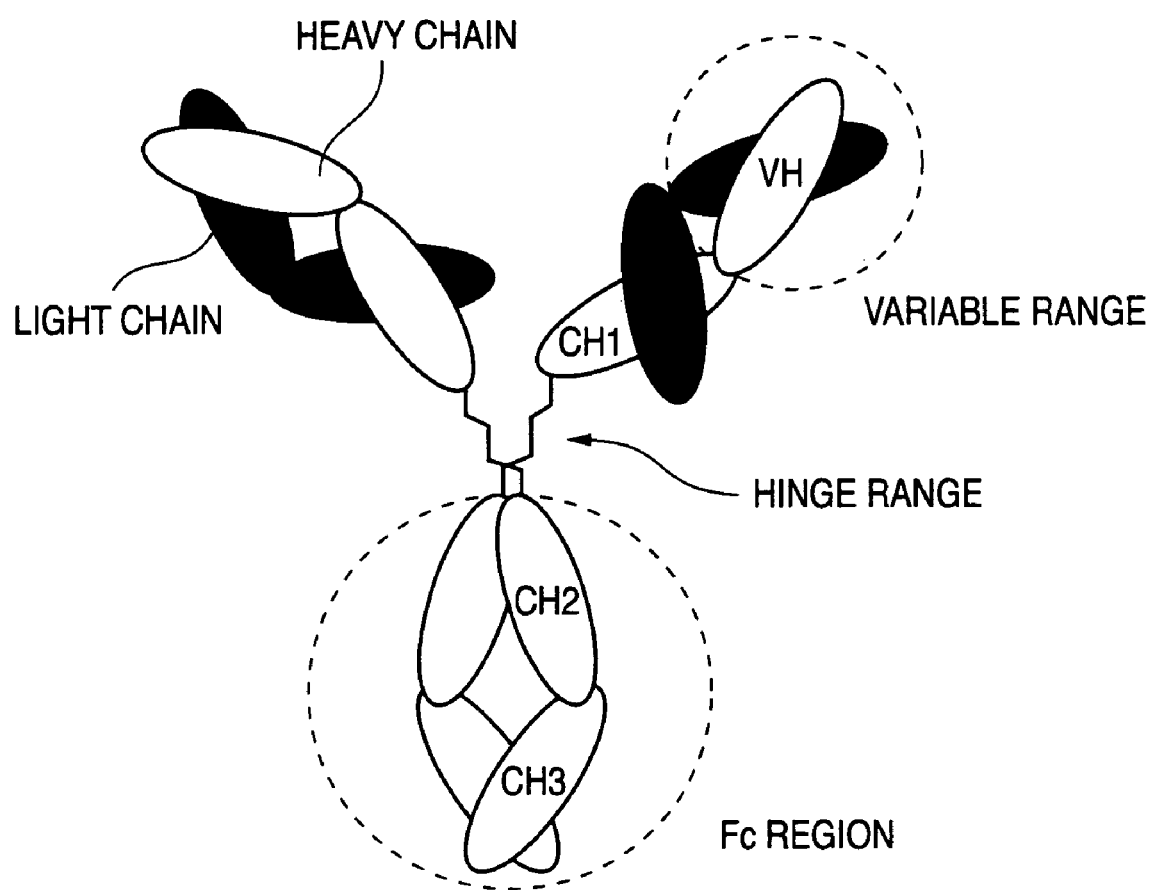
FIG. 1 shows a schematic illustration of a human IgG1 molecule.

The present invention relates to a medicament for treating a patient who cannot be cured with a medicament (hereinafter referred to as "conventional antibody medicament of the present invention") comprising as an active ingredient an antibody composition produced by a cell unresistant to a lectin which recognizes a sugar chain in which 1-position of fucose is bound to 6-position of N-acetylglucosamine in the reducing end through α-bond in a complex N-glycoside-linked sugar chain (hereinafter referred to as "α1,6-fucose/lection-unresistant cell"), which comprises as an active ingredient an antibody composition produced by a cell resistant to a lectin which recognizes a sugar chain in which 1-position of fucose is bound to 6-position of N-acetylglucosamine in the reducing end through α-bond in a complex N-glycoside-linked sugar chain (hereinafter referred to as "α1,6-fucose/lection-resistant cell").

As the α1,6-fucose/lectin-resistant cell of the present invention, any cell may be used, so long as it is a cell such as yeast, an animal cell, an insect cell or a plant cell which can be used for producing an antibody composition and is a cell resistant to a lectin which recognizes a sugar chain in which 1-position of fucose is bound to 6-position of N-acetylglucosamine in the reducing end through α-bond in a complex N-glycoside-linked sugar chain.

Examples include a hybridoma cell, a host cell for producing a human antibody or a humanized antibody, an embryonic stem cell and fertilized egg cell for producing a transgenic non-human animal which produces a human antibody, a myeloma cell, a cell derived from a transgenic non-human animal and the like which are resistant to lectin which recognizes a sugar chain in which 1-position of fucose is bound to 6-position of N-acetylglucosamine in the reducing end through α-bond in a complex N-glycoside-linked sugar chain. The myeloma cell can be used as a fusion cell for producing a hybridoma cell. Also, a hybridoma cell can be produced by immunizing a transgenic non-human animal with an antigen and using spleen cells of the animal.

The lectin-resistant cell is a cell of which growth is not inhibited even when a lectin is applied at an effective concentration.

In the present invention, the effective concentration of a lectin which does not inhibit the growth can be decided depending on the cell line, and which is generally 10 μg/ml to 10.0 mg/ml, preferably 0.5 to 2.0 mg/ml. The effective concentration in the case where mutation is introduced into a parent cell is a concentration in which the parent cell cannot normally grow or higher than the concentration, and is a concentration which is preferably similar to, more preferably 2 to 5 times, still more preferably at least 10 times, and most preferably at least 20 times, higher than the concentration in which the parent cell cannot normally grow.

The parent cell means a cell before a certain treatment is applied, namely a cell before the step for selecting the α1,6-fucose-resistant cell used in the present invention is carried out or a cell before genetic engineering techniques for decreasing or deleting the above enzyme activity are carried out.

Although the parent cell is not particularly limited, the following cells are exemplified.

The parent cell of NS0 cell includes NS0 cells described in literatures such as *BIO/TECHNOLOGY*, 10, 169 (1992) and *Biotechnol. Bioeng.*, 73, 261 (2001). Furthermore, it includes NS0 cell line (RCB 0213) registered at RIKEN Cell Bank, The Institute of Physical and Chemical Research, sub-cell lines obtained by acclimating these cell lines to media in which they can grow, and the like.

The parent cell of SP2/0-Ag14 cell includes SP2/0-Ag14 cells described in literatures such as *J. Immunol.*, 126, 317 (1981), *Nature*, 276, 269 (1978) and *Human Antibodies and Hybridomas*, 3, 129 (1992). Furthermore, it includes SP2/0-Ag14 cell (ATCC CRL-1581) registered at ATCC, sub-cell lines obtained by acclimating these cell lines to media in which they can grow (ATCC CRL-1581.1), and the like.

The parent cell of CHO cell derived from Chinese hamster ovary tissue includes CHO cells described in literatures such as *Journal of Experimental Medicine*, 108, 945 (1958), *Proc. Natl. Acad. Sci. USA*, 60, 1275 (1968), *Genetics*, 55, 513 (1968), *Chromosoma*, 41, 129 (1973), *Methods in Cell Science*, 18, 115 (1996), *Radiation Research*, 148, 260 (1997), *Proc. Natl. Acad. Sci. USA*, 77, 4216 (1980), *Proc. Natl. Acad. Sci. USA*, 60, 1275 (1968), *Cell*, 6, 121 (1975) and *Molecular Cell Genetics*, Appendix I, II (p. 883-900). Furthermore, it includes cell line CHO-K1 (ATCC CCL-61), cell line DUXB11 (ATCC CRL-9060) and cell line Pro-5 (ATCC CRL-1781) registered at ATCC, commercially available cell line CHO-S (Cat # 11619 of Life Technologies), sub-cell lines obtained by acclimating these cell lines to media in which they can grow, and the like.

The parent cell of a rat myeloma cell line YB2/3HL.P2.G11.16Ag.20 cell includes cell lines established from Y3/Ag1.2.3 cell (ATCC CRL-1631) such as YB2/3HL.P2.G11.16Ag.20 cell described in literatures such as *J. Cell. Biol.*, 93, 576 (1982) and *Methods Enzymol.*, 73B, 1 (1981). Furthermore, it include YB2/3HL.P2.G11.16Ag.20 cell (ATCC CRL-1662) registered at ATCC, sub-lines obtained by acclimating these cell lines to media in which they can grow, and the like.

As the lectin which recognizes a sugar chain structure in which 1-position of fucose is bound to 6-position of N-acetylglucosamine in the reducing end through α-bond in the N-glycoside-linked sugar chain, any lectin can be used, so long as it can recognize the sugar chain structure. Examples include a *Lens culinaris* lectin LCA (lentil agglutinin derived from *Lens culinaris*), a pea lectin PSA (pea lectin derived from *Pisuom sativum*), a broad bean lectin VFA (agglutinin derived from *Vicia faba*), an *Aleuria aurantia* lectin AAL (lectin derived from *Aleuria aurantia*) and the like.

In the present invention, the α1,6-fucose/lectin-resistant cell may be any cell, so long as growth of the cell is not inhibited in the presence of a lectin at a definite effective concentration. Examples include cells in which the activity of at least one protein shown below is decreased or deleted, and the like.

(a) an enzyme protein relating to the synthesis of an intracellular sugar nucleotide, GDP-fucose, (hereinafter referred to "GDP-fucose synthase");

(b) an enzyme protein relating to the sugar chain modification in which 1-position of fucose is bound to 6-position of N-acetylglucosamine in the reducing end through α-bond in a complex N-glycoside-linked sugar chain (hereinafter referred to as "α1,6-fucose modifying enzyme"); and (c) a protein relating to the transportation of the intracellular sugar nucleotide, GDP-fucose, to the Golgi body (hereinafter referred to as "GDP-fucose transport protein").

The GDP-fucose synthase may be any enzyme, so long as it is an enzyme relating to the synthesis of the intracellular sugar nucleotide, GDP-fucose, as a supply source of fucose to a sugar chain, and includes an enzyme which has influence on the synthesis of the intracellular sugar nucleotide, GDP-fucose, and the like.

The intracellular sugar nucleotide, GDP-fucose, is supplied by a de novo synthesis pathway or a salvage synthesis pathway. Thus, all enzymes relating to the synthesis pathways are included in the GDP-fucose synthase.

The GDP-fucose synthase relating to the de novo synthesis pathway includes GDP-mannose 4-dehydratase (hereinafter referred to as "GMD"), GDP-keto-6-deoxymannose 3,5-epimerase, 4-reductase (hereinafter referred to as "Fx") and the like.

The GDP-fucose synthase relating to the salvage synthesis pathway includes GDP-beta-L-fucose pyrophosphorylase (hereinafter referred to as "GFPP"), fucokinase and the like.

The enzyme which has influence on the synthesis of an intracellular sugar nucleotide, GDP-fucose also includes an enzyme which has influence on the activity of the enzyme relating to the synthesis of the intracellular sugar nucleotide, GDP-fucose, and an enzyme which has influence on the structure of substances as the substrate of the enzyme.

The α1,6-fucose modifying enzyme includes any enzyme, so long as it is an enzyme relating to the reaction of binding of 1-position of fucose to 6-position of N-acetylglucosamine in the reducing end through α-bond in the complex N-glycoside-linked sugar chain. The enzyme relating to the reaction of binding of 1-position of fucose to 6-position of N-acetylglucosamine in the reducing end through α-bond in the complex N-glycoside-linked sugar chain includes an enzyme which has influence on the reaction of binding of 1-position of fucose to 6-position of N-acetylglucosamine in the reducing end through α-bond in the complex N-glycoside-linked sugar chain. Examples include α1,6-fucosyltransferase, α-L-fucosidase and the like.

Also, the enzyme relating to the reaction of binding of 1-position of fucose to 6-position of N-acetylglucosamine in the reducing end through α-bond in the complex N-glycoside-linked sugar chain includes an enzyme which has influence on the activity the enzyme relating to the reaction of binding of 1-position of fucose to 6-position of N-acetylglucosamine in the reducing end through α-bond in the complex N-glycoside-linked sugar chain and an enzyme which has influence on the structure of substances as the substrate of the enzyme.

The GDP-fucose transport protein may be any protein, so long as it is a protein relating to the transportation of the intracellular sugar nucleotide, GDP-fucose, to the Golgi body, and includes a GDP-fucose transporter and the like.

Furthermore, the GDP-fucose transport protein includes a protein which has an influence on the reaction to transport the intracellular sugar nucleotide, GDP-fucose, to the Golgi body, and specifically includes a protein which has an influence on the above protein relating to the transportation of the intracellular sugar nucleotide, GDP-fucose, to the Golgi body or has an influence on the expression thereof.

As a method for obtaining a cell used in the production process of the present invention, any technique can be used, so long as it is a technique by which can select the α1,6-fucose/lectin-resistance cell. Specifically, the method includes a technique for decreasing or deleting the activity of the above protein. The technique for decreasing or deleting the above protein includes:

(a) a gene disruption technique which comprises targeting a gene encoding the protein, (b) a technique for introducing a dominant negative mutant of a gene encoding the protein, (c) a technique for introducing mutation into the protein, (d) a technique for suppressing transcription and/or translation of a gene encoding the protein, and the like.

The patient who cannot be cured with the conventional medicament includes a patient in which an antigen which is recognized by the antibody composition in the target cell of the patient is expressed in such an amount that the antibody composition cannot exert sufficient therapeutic effect.

As the antigen of the present invention, any antigen which reacts with the antibody composition expressed in the target cell is included.

As the target cell in the present invention, any cell which expresses the antigen which reacts with the antibody composition relating to the disease of the patient is included.

As the diseases in the present invention, any diseases can be included, so long as the target cell directly or indirectly relates to the pathology. Examples include malignant tumors relating to tumor cells, neovascular cells, interstitial cells and the like; allergies, inflammation and autoimmune diseases relating to immune cells, cardiovascular diseases relating to vascular cells, platelets, smooth muscle cells and the like; diseases accompanied with viral infection, and diseases accompanied with bacterial infection.

The upper limit of the expression amount of the antigen in the target cell in which the expression of the antigen is few and for which the medicament of the present invention is effective is preferably $10^5$, more preferably $5 \times 10^4$, still more preferably $2 \times 10^4$, particularly preferably 1 and most preferably $5 \times 10^3$, per target cell.

Specifically, in the case of one of human chemokine receptors, CCR4 (hereinafter referred to as "CCR4"), the upper limit is preferably $10^5$, more preferably $5 \times 10^4$, still more preferably $2 \times 10^4$, particularly preferably $10^4$ and most preferably $5 \times 10^3$, per target cell.

In the case of human CD20 (hereinafter referred to as "CD20"), the upper limit is preferably $10^5$, more preferably $5 \times 10^4$, still more preferably $3 \times 10^4$, particularly preferably $2 \times 10^4$ and most preferably $10^4$, per target cell.

In the case of human HER2 (hereinafter referred to as "HER2"), the upper limit is preferably $5 \times 10^5$, more preferably $10^5$, still more preferably $5 \times 10^4$, particularly preferably $3 \times 10^4$ and most preferably $2 \times 10^4$, per target cell.

The lower limit of the expression amount of the antigen in the target cell in which the expression of the antigen is few and for which the medicament of the present invention is effective is preferably 1, more preferably $10^2$, still more preferably $3 \times 10^2$, particularly preferably $10^3$ and most preferably $3 \times 10^3$, per target cell.

Specifically, in the case of CCR4, the lower limit is preferably 1, more preferably $10^2$, still more preferably $5 \times 10^2$, particularly preferably $10^3$ and most preferably $3 \times 10^3$, per target cell.

In the case of CD20, the lower limit is preferably 1, more preferably $10^2$, still more preferably $10^3$, particularly preferably $2 \times 10^3$ and most preferably $5 \times 10^3$, per target cell.

In the case of HER2, the lower limit is preferably 1, more preferably $10^2$, still more preferably $10^3$, particularly preferably $5 \times 10^3$ and most preferably $1 \times 10^4$, per target cell.

The expression amount of the antigen in the target cell in the patient or disease which is the subject for treatment of the medicament of the present invention can be measured by any immunological method using the binding reaction between the antibody and the antigen such as flow cytometory, Scatchard plot, tissue immunostaining and immunoassay.

Furthermore, when the ligand for the antigen is known, the binding activity of the ligand to the target cell can be measured by detection using a method such as flow cytometory, Scatchard plot, tissue immunostaining or immunoassay.

The amount that the antibody composition cannot exert sufficient therapeutic effect is such an amount that the antibody composition cannot exert sufficient ADCC activity.

Specifically, when the amount that the antibody composition cannot exert sufficient ADCC activity, the antibody composition cannot injure the target cell in the patient.

In the present invention, the antibody composition may be any composition, so long as it comprises an antibody molecule having a complex N-glycoside-linked sugar chain in the Fc region.

The antibody molecule is a tetramer in which two molecules of each of two polypeptide chains, a heavy chain and a light chain (hereinafter referred to as "H chain" and "L chain", respectively), are respectively associated. Each of about a quarter of the N-terminal side of the H chain and about a quarter of the N-terminal side of the L chain (more than 100 amino acids for each) is called V region which is rich in diversity and directly relates to the binding with an antigen. The greater part of the moiety other than the V region is called C region. Based on homology with the C region, antibody molecules are classified into classes IgG, IgM, IgA, IgD and IgE.

Also, the IgG class is further classified into subclasses IgG1 to IgG4 based on homology with the C region. A schematic illustration of the antibody molecule belonging to IgG1 subclass is shown in FIG. 1.

The H chain is divided into four immunoglobulin domains VH, CH1, CH2 and CH3 from its N-terminal side, and a highly flexible peptide region called hinge region is present between CH1 and CH2 to divide CH1 and CH2. A structural unit comprising CH2 and CH3 after the hinge region is called Fc region to which a complex N-glycoside-linked sugar chain is bound and is also a region to which an Fc receptor, a complement and the like are bound (*Immunology Illustrated*, the Original, 5th edition, published on Feb. 10, 2000, by Nankodo; *Handbook of Antibody Technology* (*Xotai Kogaku Nyumon*), 1st edition on Jan. 25, 1994, by Chijin Shokan).

Sugar chains of glycoproteins such as an antibody molecule are roughly divided into two types, namely a sugar chain which binds to asparagine (N-glycoside-linked sugar chain) and a sugar chain which binds to other amino acid such as serine, threonine (O-glycoside-linked sugar chain), based on the binding form to the protein moiety. The N-glycoside-linked sugar chains have a basic common core structure shown by the following structural formula (I):

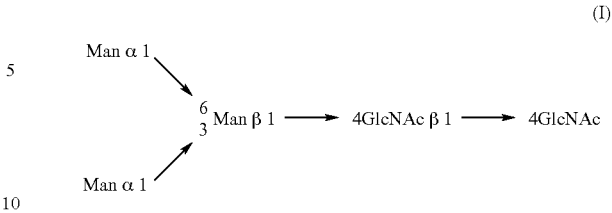

In formula (I), the sugar chain terminus which binds to asparagine is called a reducing end, and the opposite side is called a non-reducing end.

The N-glycoside-linked sugar chain may be any N-glycoside-linked sugar chain, so long as it comprises the core structure of formula (I). Examples include a high mannose type in which mannose alone binds to the non-reducing end of the core structure; a complex type in which the non-reducing end side of the core structure has at least one parallel branches of galactose-N-acetylglucosamine (hereinafter referred to as "Gal-GlcNAc") and the non-reducing end side of Gal-GlcNAc has a structure of sialic acid, bisecting N-acetylglucosamine or the like; a hybrid type in which the non-reducing end side of the core structure has branches of both of the high mannose type and complex type, and the like.

Since the Fc region in the antibody molecule has positions to which N-glycoside-linked sugar chains are separately bound, two sugar chains are bound per one antibody molecule. Since the N-glycoside-linked sugar chain which binds to an antibody molecule includes any sugar chain having the core structure represented by formula (I), a number of combinations of sugar chains may possible for the two N-glycoside-linked sugar chains which bind to the antibody.

Accordingly, the antibody composition of the present invention which is produced by the α1,6-fucose/lectin-resistant cell may comprise an antibody which is bound to the same sugar chain structure or an antibody having different sugar chain structures, so long as the effect of the present invention is obtained from the composition.

The antibody molecule may be any antibody molecule, so long as it is a molecule comprising the Fc region of an antibody. Examples include an antibody, an antibody fragment, a fusion protein comprising an Fc region, and the like.

The antibody includes an antibody secreted by a hybridoma cell prepared from a spleen cell of an animal immunized with an antigen, an antibody prepared by genetic engineering technique, i.e., an antibody obtained by introducing an antibody expression vector to which DNA encoding an antibody is inserted, into a host cell; and the like. Examples include an antibody produced by a hybridoma, a humanized antibody, a human antibody and the like.

A hybridoma is a cell which is obtained by cell fusion between a B cell obtained by immunizing a non-human mammal with an antigen and a myeloma cell derived from mouse or the like, and can produce a monoclonal antibody having the desired antigen specificity.

The humanized antibody includes a human chimeric antibody, a human CDR-grafted antibody and the like.

A human chimeric antibody is an antibody which comprises an antibody H chain V region (hereinafter referred to as "HV" or "VH") and an antibody L chain V region (hereinafter referred to as "LV" or "VL"), both of a non-human animal, a human antibody H chain C region (hereinafter also referred to as "CH") and a human antibody L chain C region (hereinafter also referred to as "CL"). The non-human animal may be any animal such as mouse, rat, hamster or rabbit, so long as a hybridoma can be prepared therefrom.

The human chimeric antibody can be produced by obtaining cDNAs encoding VH and VL from a monoclonal antibody-producing hybridoma, inserting them into an expression vector for host cell having genes encoding human antibody CH and human antibody CL to thereby construct a human chimeric antibody expression vector, and then introducing the vector into a host cell to express the antibody.

The CH of human chimeric antibody may be any CH, so long as it belongs to human immunoglobulin (hereinafter referred to as "gIg") can be used. Those belonging to the hIgG class are preferred and any one of the subclasses belonging to the hIgG class, such as hIgG1, hIgG2, hIgG3 and hIgG4, can be used. Also, as the CL of human chimeric antibody, any CL can be used, so long as it belongs to the hIg class, and those belonging to the κ class or λ class can also be used.

A human CDR-grafted antibody is an antibody in which amino acid sequences of CDRs of VH and VL of a non-human animal antibody are grafted into appropriate positions of VH and VL of a human antibody.

The human CDR-grafted antibody can be produced by constructing cDNAs encoding V regions in which CDRs of VH and VL of a non-human animal antibody are grafted into CDRs of VH and VL of a human antibody, inserting them into an expression vector for host cell having genes encoding human antibody CH and human antibody CL to thereby construct a human CDR-grafted antibody expression vector, and then introducing the expression vector into a host cell to express the human CDR-grafted antibody.

The CH of human CDR-grafted antibody may be any CH, so long as it belongs to the hIg. Those of the hIgG class are preferred and any one of the subclasses belonging to the hIgG class, such as hIgG1, hIgG2, hIgG3 and hIgG4, can be used. Also, as the CL of human CDR-grafted antibody, any CL can be used, so long as it belongs to the hIg class, and those belonging to the κ class or λ class can also be used.

A human antibody is originally an antibody naturally existing in the human body, but it also includes antibodies obtained from a human antibody phage library, a human antibody-producing transgenic animal and a human antibody-producing transgenic plant, which are prepared based on the recent advance in genetic engineering, cell engineering and developmental engineering techniques.

Regarding the antibody existing in the human body, a lymphocyte capable of producing the antibody can be cultured by isolating a human peripheral blood lymphocyte, immortalizing it by its infection with EB virus or the like and then cloning it, and the antibody can be purified from the culture.

The human antibody phage library is a library in which antibody fragments such as Fab and single chain antibody are expressed on the phage surface by inserting a gene encoding an antibody prepared from a human B cell into a phage gene. A phage expressing an antibody fragment having binding activity for the desired antigen can be collected from the library based on the activity to bind to an antigen-immobilized substrate. The antibody fragment can be converted further into a human antibody molecule comprising two full H chains and two full L chains by genetic engineering techniques.

A human antibody-producing transgenic non-human animal is an animal in which a gene encoding a human antibody is introduced into cells. Specifically, a human antibody-producing transgenic non-human animal can be prepared by introducing a gene encoding a human antibody into ES cell derived from a mouse, transplanting the ES cell into an early stage embryo derived from other mouse and then developing it. By introducing a gene encoding a human antibody gene into a fertilized egg and developing it, the transgenic non-human animal can be also prepared. Regarding the preparation method of a human antibody from the human antibody-producing transgenic non-human animal, the human antibody can be produced and accumulated in a culture by obtaining a human antibody-producing hybridoma by a hybridoma preparation method usually carried out in non-human mammals and then culturing it.

The transgenic non-human animal includes cattle, sheep, goat, pig, horse, mouse, rat, fowl, monkey, rabbit and the like.

An antibody fragment is a fragment which comprises at least a part of the Fc region consisting of an antibody. The Fc region is a region at the C-terminal of H chain consisting of an antibody, consists CH2 region and CH3 region, and includes a natural type and a mutant type. The at least part of the Fc region is preferably a fragment comprising CH2 region, more preferably a region comprising aspartic acid at position 1 present in the CH2 region. The Fc region of the IgG class is from Cys at position 226 to the C-terminal or from Pro at position 230 to the C-terminal according to the numbering of EU Index of Kabat et al. [*Sequences of Proteins of Immunological Interest*, 5$^{th}$ Ed., Public Health Service, National Institutes of Health, Bethesda, Md. (1991)]. The antibody fragment includes an H chain monomer, an H chain dimer and the like.

A fusion protein comprising an Fc region is a composition in which an antibody comprising the Fc region of an antibody or the antibody fragment is fused with a protein such as an enzyme or a cytokine (hereinafter referred to as "Fc fusion protein").

Furthermore, the present invention relates to a medicament which comprises an antibody composition produced by the α1,6-fucose/lectin-resistant cell which has a higher ADCC than the antibody composition produced by the α1,6-fucose/lectin-unresistant cell.

The antibody composition having a higher ADCC than the antibody composition produced by the α1,6-fucose/lectin-unresistant cell can be produced by the above α1,6-fucose/lectin-resistant cell.

The ADCC activity is a cytotoxic activity in which an antibody bound to a cell surface antigen on a cell such as a tumor cell in the living body activates an effector cell through an Fc receptor existing on the antibody Fc region and effector cell surface and thereby injure the tumor cell and the like [*Monoclonal Antibodies: Principles and Applications*, Wiley-Liss, Inc., Chapter 2.1 (1995)]. The effector cell includes immune cells such as natural killer cells, macrophages, monocytes, dendritic cells and granulocytes. Furthermore, the Fc receptor is classified into Fcα receptor I, Fcε receptor I, Fcε receptor II, Fcγ receptor I, Fcγ receptor IIa, Fcγ receptor IIb, Fcγ receptor IIc, Fcγ receptor BIIa, Fcγ receptor IIIb, Fc receptor n and the like. Among these, the Fcγ receptor IIIa is mainly expressed on the natural killer cell, and is one of the important Fc receptors for the ADCC activity [*Monoclonal Antibodies: principles and practise*, Third Edition, Acad. Press, 1996 (hereinafter referred to as "*Monoclonal Antibodies*")].

Also, in addition to the ADCC activity, the cyotoxic activity owned by the antibody composition includes CDC activity (*Monoclonal Antibody*), growth inhibition activity of antigen-expressing cells due to binding to the antigen, and the like. The growth inhibition activity also includes activity of promoting apoptosis induction or differentiation induction of the target cell [*Cancer Research*, 60, 7170 (2000); *Nature Medicine*, 1, 644 (1995); *Cell Growth Differ.*, 3, 401 (1992)].

When, in the antibody composition, the ratio of sugar chains in which fucose is not bound to N-acetylglucosamine in the reducing end among the total complex N-glycoside-linked sugar chains binding to the Fc region contained in the antibody molecule is higher than that of the antibody composition produced by the α1,6-fucose/lectin-unresistant cell, the antibody composition produced by the α1,6-fucose/lectin-resistant cell has higher ADCC activity than the antibody composition produced by the α1,6-fucose/lectin-unresistant cell.

As the ratio of sugar chains in which fucose is not bound to N-acetylglucosamine in the reducing end in the sugar chain among the total complex N-glycoside-linked sugar chains binding to the Fc region contained in the antibody composition is the higher, the ADCC activity of the antibody composition is the higher. The antibody composition having high ADCC activity includes an antibody composition in which the ratio of sugar chains in which fucose is not bound to N-acetylglucosamine in the reducing end among the total complex N-glycoside-linked sugar chains binding to the Fc region contained in the antibody composition is preferably 20% or more, more preferably 30% or more, still more preferably 40% or more, particularly preferably 50% or more and most preferably 100%.

Furthermore, the antibody composition having high ADCC activity produced by CHO cell includes an antibody composition in which the ratio of sugar chains in which fucose is not bound to N-acetylglucosamine in the reducing end among the total complex N-glycoside-linked sugar chains binding to the Fc region contained in the antibody composition is preferably 20% or more, more preferably 30% or more, still more preferably 40% or more, particularly preferably 50% or more and most preferably 100%.

The ratio of sugar chains in which fucose is not bound to N-acetylglucosamine in the reducing end among the total complex N-glycoside-linked sugar chains bound to the Fc region contained in the antibody composition is a ratio of the number of a sugar chain in which fucose is not bound to N-acetylglucosamine in the reducing end in the sugar chain to the total number of the complex N-glycoside-linked sugar chains bound to the Fc region contained in the composition. Also, the ratio of sugar chains is preferably a ratio of sugar chains in which 1-position of fucose is not bound to 6-position of N-acetylglucosamine in the reducing end through α-bond.

The sugar chain in which fucose is not bound to N-acetylglucosamine in the reducing end in the complex N-glycoside-linked sugar chain is a complex N-glycoside-linked sugar chain in which fucose is not bound to N-acetylglucosamine in the reducing end through α-bond. Preferably, it is a complex N-glycoside-linked sugar chain in which 1-position of fucose is not bound to 6-position of N-acetylglucosamine through α-bond.

The ratio of a sugar chain in which fucose is not bound to N-acetylglucosamine in the reducing end in the sugar chains contained in the composition which comprises an antibody molecule having complex N-glycoside-linked sugar chains in the Fc region can be determined by separating the sugar chain from the antibody molecule using a known method such as hydrazinolysis, enzyme digestion or the like [*Biochemical Experimentation Methods* 23—*Method for Studying Glycoprotein Sugar Chain* (Japan Scientific Societies Press), edited by Reiko Takahashi (1989)]), carrying out fluorescence labeling or radioisotope labeling of the released sugar chain, and then separating the labeled sugar chain by chromatography.

Also, the separating sugar chain can be determined by analyzing it with the HPAED-PAD method [*J. Liq. Chromatogr.*, 6, 1577 (1983)].

Moreover, in the present invention, the antibody is preferably an antibody which recognizes a tumor-related antigen, an antibody which recognizes an allergy- or inflammation-related antigen, an antibody which recognizes cardiovascular disease-related antigen or an antibody which recognizes a viral or bacterial infection-related antigen. Also, the class of the antibody is preferably IgG.

The antibody which recognizes a tumor-related antigen includes anti-GD2 antibody [*Anticancer Res.*, 13, 331-336 (1993)], anti-GD3 antibody [*Cancer Immunol. Immunother.*, 36, 260-266 (1993)], anti-GM2 antibody [*Cancer Res.*, 54, 1511-1516 (1994)], anti-HER2 antibody [*Proc. Natl. Acad. Sci. USA*, 89, 4285-4289 (1992)], anti-CD52 antibody [*Proc Natl. Acad. Sci. USA*, 89, 4285-4289 (1992)], anti-MAGE antibody [*British J. Cancer*, 83, 493497 (2000)], anti-HM1.24 antibody [*Molecular Immunol.*, 36, 387-395 (1999)], anti-parathyroid hormone-related protein (PTHrP) antibody [*Cancer*, 88, 2909-2911 (2000)], anti-basic fibroblast growth factor antibody and anti-FGF8 antibody [*Proc. Natl. Acad. Sci. USA*, 86, 9911-9915 (1989)], anti-basic fibroblast growth factor receptor antibody and anti-FGF8 receptor antibody [*J. Biol. Chem.*, 265, 16455-16463 (1990)], anti-insulin-like growth factor antibody [*J. Neurosci. Res.*, 40, 647-659 (1995)], anti-insulin-like growth factor receptor antibody [*J. Neurosci. Res.*, 40, 647-659 (1995)], anti-PMSA antibody [*J. Urology*, 160, 2396-2401 (1998)], anti-vascular endothelial cell growth factor antibody [*Cancer Res.*, 57, 4593-4599 (1997)], anti-vascular endothelial cell growth factor receptor antibody [*Oncogene*, 19, 2138-2146 (2000)] and the like.

The antibody which recognizes an allergy- or inflammation-related antigen includes anti-interleukin 6 antibody [*Immunol Rev.*, 127, 5-24 (1992)], anti-interleukin 6 receptor antibody [*Molecular Immunol.*, 31, 371-381 (1994)], anti-interleukin 5 antibody [*Immunol. Rev.*, 127, 5-24 (1992)], anti-interleukin 5 receptor antibody and anti-interleukin 4 antibody [*Cytokine*, 3, 562-567 (1991)], anti-tumor necrosis factor antibody [*Hybridoma*, 13, 183-190 (1994)], anti-tumor necrosis factor receptor antibody [*Molecular Pharmacol.*, 58, 237-245 (2000)], anti-CCR4 antibody [Nature, 400, 776-780 (1999)], anti-chemokine antibody [*J. Immuno. Meth.*, 174, 249-257 (1994)], anti-chemokine receptor antibody [*J. Exp. Med.*, 186, 1373-1381 (1997)] and the like. The antibody which recognizes a cardiovascular disease-related antigen includes anti-GpIIb/IIIa antibody [*J. Immunol.*, 152, 2968-2976 (1994)], anti-platelet-derived growth factor antibody [*Science*, 253, 1129-1132 (1991)], anti-platelet-derived growth factor receptor antibody [*J. Biol. Chem.*, 272, 17400-17404 (1997)] and anti-blood coagulation factor antibody [*Circulation*, 101, 1158-1164 (2000)] and the like.

The antibody which recognizes a viral or bacterial infection-related antigen includes anti-gp120 antibody [*Structure*, 8, 385-395 (2000)], anti-CD4 antibody [*J. Rheumatology*, 25, 2065-2076 (1998)], anti-CCR4 antibody and anti-Vero toxin antibody [*J. Clin. Microbiol*, 37, 39&399 (1999)] and the like.

Furthermore, the present invention relates to a method for treating a patient using the medicament of the present invention. The treatment of the patient using the medicament means that the patient is treated by administration of the medicament.

Moreover, the present invention relates to a distinction method for expecting effects before the administration of the medicament to a patient. Specifically, the method includes a method comprising the following steps: (i) contacting a medicament of conventional antibody or a medicament of the present invention with target cells collected from a patient, (ii) measuring the activity of each medicament reacted with the target cells, (iii) comparing the activity of the medicament of conventional antibody with the activity of the medicament of the present invention.

The present invention is explained in detail below.

1. Preparation of Host Cell

The host cell for the production of an antibody composition used in the present invention can be prepared by the following techniques.

(1) Gene Disruption Technique which Comprises Targeting a Gene Encoding an Enzyme The host cell can be prepared by using a gene disruption technique by targeting a gene encoding a GDP-fucose synthase, α1,6-fucose modifying enzyme or a GDP-fucose transport protein. The GDP-fucose synthase includes GMD, Fx, GFPP, fucokinase and the like. The α1,6-fucose modifying enzyme includes α-1,6-fucosyltransferase, α-L-fucosidase and the like. The GDP-fucose transport protein includes GDP-fucose transporter.

The gene as used herein includes DNA and RNA.

The gene disruption method may be any method, so long as it can disrupt the gene encoding the target enzyme. Examples include an antisense method, a ribozyme method, a homologous recombination method, an RNA-DNA oligonucleotide (RDO) method, an RNA interference (RNAi) method, a method using retrovirus, a method using transposon and the like. The methods are specifically described below.

(a) Preparation of Host Cell by the Antisense Method or the Ribozyme Method

The host cell can be prepared by targeting the GDP-fucose synthase, α1,6-fucose modifying enzyme or the GDP-fucose transport protein according to the antisense or ribozyme method described in *Cell Technology*, 12, 239 (1993); *BIO/TECHNOLOGY*, 17, 1097 (1999); *Hum. Mol. Genet.*, 5, 1083 (1995), *Cell Technology*, 13, 255 (1994); *Proc. Natl. Acad. Sci. USA*, 96, 1886 (1999); or the like, e.g., in the following manner.

A cDNA or a genomic DNA encoding the GDP-fucose synthase, α1,6-fucose modifying enzyme or the GDP-fucose transport protein is prepared.

The nucleotide sequence of the prepared cDNA or genomic DNA is determined.

Based on the determined DNA sequence, an antisense gene or ribozyme construct of an appropriate length comprising a part of a DNA which encodes the GDP-fucose synthase, α1,6-fucose modifying enzyme or the GDP-fucose transport protein, its untranslated region or an intron is designed.

In order to express the antisense gene or ribozyme in a cell, a recombinant vector is prepared by inserting a fragment or total length of the prepared DNA into downstream of the promoter of an appropriate expression vector.

A transformant is obtained by introducing the recombinant vector into a host cell suitable for the expression vector.

The host cell can be obtained by selecting a transformant based on the activity of the GDP-fucose synthase, the α1,6-fucose modifying enzyme or the GDP-fucose transport protein. The host cell of the present invention can also be obtained by selecting a transformant based on the sugar chain structure of a glycoprotein on the cell membrane or the sugar chain structure of the produced antibody molecule.

As the host cell for preparing the host cell of the present invention, any cell such as yeast, an animal cell, an insect cell or a plant cell can be used, so long as it has a gene encoding the target GDP-fucose synthase, α1,6-fucose modifying enzyme or GDP-fucose transport protein. Examples include host cells described in the following item 3.

As the expression vector, a vector which is autonomously replicable in the host cell or can be integrated into the chromosome and comprises a promoter at such a position that the designed antisense gene or ribozyme can be transferred can be used. Examples include expression vectors described in the following item 3.

As the method for introducing a gene into various host cells, the methods for introducing recombinant vectors suitable for various host cells described in the following item 3 can be used.

The method for selecting a transformant based on the activity of the GDP-fucose synthase, the α1,6-fucose modifying enzyme or the GDP-fucose transport protein includes biochemical methods or genetic engineering techniques described in *New Biochemical Experimentation Series (Shin-Jikken Kagaku Koza)* 3—*Saccharides (Toshitsu) I*, Glycoprotein (Totanpakushitu) (Tokyo Kagaku Dojin), edited by Japanese Biochemical Society (1988); *Cell Engineering (Saibo Kogaku)*, Supplement, Experimental Protocol Series, Glycobiology Experimental Protocol, Glycoprotein, Glycolipid and Proteoglycan (Shujun-sha), edited by Naoyuki Taniguchi, Akemi Suzuki, Kiyoshi Furukawa and Kazuyuki Sugawara (1996); *Molecular Cloning, A Laboratory Manual*, Second Edition, Cold Spring Harbor Laboratory Press, 1989 (hereinafter referred to as *Molecular Cloning*, Second Edition); *Current Protocols in Molecular Biology*, John Wiley & Sons, 1987-1997 (hereinafter referred to as "*Current Protocols in Molecular Biology*"); and the like. The biochemical method includes a method in which the enzyme activity is evaluated using an enzyme-specific substrate and the like. The genetic engineering technique include the Northern analysis, RT-PCR and the like wherein the amount of mRNA of a gene encoding the enzyme is measured.

The method for selecting a transformant based on the sugar chain structure of a glycoprotein on the cell membrane includes the methods described later in the following item 1(5). The method for selecting a transformant based on the sugar chain structure of a produced antibody molecule includes the methods described in the following items 5 and 6.

As the method for preparing cDNA encoding the GDP-fucose synthase, α1,6-fucose modifying enzyme or the GDP-fucose transport protein, the following method is exemplified.

Preparation Method of DNA:

A total RNA or mRNA is prepared from human or non-human animal tissues or cells.

A cDNA library is prepared from the prepared total RNA or mRNA.

Degenerative primers are produced based on the amino acid sequence of the GDP-fucose synthase, the α1,6-fucose modifying enzyme or the GDP-fucose transport protein, and a gene fragment encoding the GDP-fucose synthase, α1,6-fucose modifying enzyme or the GDP-fucose transport protein is obtained by PCR using the prepared cDNA library as the template.

A DNA encoding the GDP-fucose synthase, α1,6-fucose modifying enzyme or the GDP-fucose transport protein can be obtained by screening the cDNA library using the obtained gene fragment as a probe.

As the mRNA of human or non-human tissues or cells, a commercially available product (e.g., manufactured by Clontech) may be used. Also, the mRNA can be prepared as poly(A)$^+$ RNA from a total RNA by the oligo(dT)-immobilized cellulose column method (*Molecular Cloning*, Second Edition) and the like, the total RNA being prepared from human or non-human animal tissues or cells by the guanidine thiocyanate-cesium trifluoroacetate method [*Methods in Enzymology*, 114, 3 (1987)], the acidic guanidine thiocyanate phenol chloroform (AGPC) method [*Analytical Biochemistry*, 162, 156 (1987), *Experimental Medicine*, 9, 1937 (1991)] and the like.

In addition, mRNA can be prepared using a kit such as Fast Track mRNA Isolation Kit (manufactured by Invitrogen) or Quick Prep mRNA Purification Kit (manufactured by Pharmacia).

A method for preparing a cDNA library from the prepared mRNA of human or non-human animal tissues or cells includes the methods described in *Molecular Cloning*, Second Edition; *Current Protocols in Molecular Biology*, and the like, or methods using a commercially available kit such as SuperScript Plasmid System for cDNA Synthesis and Plasmid Cloning (manufactured by Life Technologies) or ZAP-cDNA Synthesis Kit (manufactured by STRATAGENE) or the like.

As the cloning vector for preparing the cDNA library, any vector such as a phage vector or a plasmid vector or the like can be used, so long as it is autonomously replicable in *Escherichia coli* K12. Examples include ZAP Express [manufactured by STRATAGENE, *Strategies*, 5, 58 (1992)], pBluescript II SK(+) [*Nucleic Acids Research*, 17, 9494 (1989)], Lambda ZAP II (manufactured by STRATAGENE), λgt10 and λgt11 [DNA Cloning, A Practical Approach, 1, 49 (1985)], λTriplEx (manufactured by Clontech), λExCell (manufactured by Pharmacia), pcD2 [*Mol. Cell. Biol.*, 3, 280 (1983)], pUC18 [*Gene*, 33, 103 (1985)] and the like.

Any microorganism can be used as the host microorganism for the preparation of the cDNA library, and *Escherichia coli* is preferably used. Examples include *Escherichia coli* XL1-Blue MRF' [manufactured by STRATAGENE, *Strategies*, 5, 81 (1992)], *Escherichia coli* C600 [Genetics, 39, 440 (1954)], *Escherichia coli* Y1088 [*Science*, 222, 778 (1983)], *Escherichia coli* Y1090 [*Science*, 222, 778 (1983)], *Escherichia coli* NM522 [*J. Mol. Biol.*, 166, 1 (1983)], *Escherichia coli* K802 [*J. Mol. Biol.*, 16, 118 (1966)], *Escherichia coli* JM105 [*Gene*, 38, 275 (1985)] and the like.

The cDNA library can be used as such in the subsequent analysis, and in order to obtain a full length cDNA as efficient as possible by decreasing the ratio of an infull length cDNA, a cDNA library prepared by using the oligo cap method developed by Sugano et al. [*Gene*, 138, 171 (1994); *Gene*, 200, 149 (1997); *Protein, Nucleic Acid and Protein*, 41, 603 (1996); *Experimental Medicine*, 11, 2491 (1993); *cDNA Cloning* (Yodo-sha) (1996); *Methods for Preparing Gene Libraries* (Yodo-sha) (1994)] can be used in the following analysis.

Based on the amino acid sequence of the GDP-fucose synthase, the α1,6-fucose modifying enzyme or the GDP-fucose transport protein, degenerative primers specific for the 5'-terminal and 3'-terminal nucleotide sequences of a nucleotide sequence presumed to encode the amino acid sequence are prepared, and DNA is amplified by PCR [*PCR Protocols*, Academic Press (1990)] using the prepared cDNA library as the template to obtain a gene fragment encoding the GDP-fucose synthase, the (α1,6-fucose modifying enzyme or the GDP-fucose transport protein.

It can be confirmed that the obtained gene fragment is a DNA encoding the GDP-fucose synthase, the α1,6-fucose modifying enzyme or the GDP-fucose transport protein, by a method generally used for analyzing a nucleotide such as the dideoxy method of Sanger et al. [*Proc. Natl. Acad. Sci. USA*, 74, 5463 (1977)] or by using a nucleotide sequence analyzer such as ABIPRISM 377 DNA Sequencer (manufactured by PE Biosystems) or the like.

A DNA encoding the GDP-fucose synthase, the α1,6-fucose modifying enzyme or the GDP-fucose transport protein can be obtained by carrying out colony hybridization or plaque hybridization (*Molecular Cloning*, Second Edition) for the cDNA or cDNA library synthesized from the mRNA contained in the human or non-human animal tissue or cell, using the gene fragment as a DNA probe.

Also, using the primers used for obtaining the gene fragment encoding the GDP-fucose synthase, the α1,6-fucose modifying enzyme or the GDP-fucose transport protein, a DNA encoding the GDP-fucose synthase, the α1,6-fucose modifying enzyme or the GDP-fucose transport protein can also be obtained by carrying out screening by PCR using the cDNA or cDNA library synthesized from the mRNA contained in human or non-human animal tissues or cells as the template.

The nucleotide sequence of the obtained DNA encoding the GDP-fucose synthase, the α1,6-fucose modifying enzyme or the GDP-fucose transport protein is analyzed from its terminus and determined by a method generally used for analyzing a nucleotide such as the dideoxy method of Sanger et al. [*Proc. Natl. Acad. Sci. USA*, 74, 5463 (1977)] or by using a nucleotide sequence analyzer such as ABIPRISM 377 DNA Sequencer (manufactured by PE Biosystems).

A gene encoding the GDP-fucose synthase, the α1,6-fucose modifying enzyme or the GDP-fucose transport protein can also be determined from genes in data bases by searching nucleotide sequence data bases such as GenBank, EMBL and DDBJ using a homology searching program such as BLAST based on the determined cDNA nucleotide sequence.

The cDNA encoding the GDP-fucose synthase, the α1,6-fucose modifying enzyme or the GDP-fucose transport protein can also be obtained by chemically synthesizing it with a DNA synthesizer such as DNA Synthesizer model 392 manufactured by Perkin Elmer using the phosphoamidite method, based on the determined DNA nucleotide sequence.

The method for preparing a genomic DNA of the GDP-fucose synthase, the α1,6-fucose modifying enzyme or the GDP-fucose transport protein includes known methods described in *Molecular Cloning*, Second Edition, *Current Protocols in Molecular Biology*, and the like. Furthermore, the genomic DNA can be prepared by using a kit such as Genome DNA Library Screening System (manufactured by Genome Systems) or Universal GenomeWalker™ Kits (manufactured by CLONTECH).

In addition, the host cell can also be obtained without using an expression vector, by directly introducing an antisense oligonucleotide or ribozyme into a host cell, which is designed based on the nucleotide sequence encoding the GDP-fucose synthase, the α1,6-fucose modifying enzyme or the GDP-fucose transport protein.

The antisense oligonucleotide or ribozyme can be prepared in the usual method or by using a DNA synthesizer. Specifically, it can be prepared based on the sequence information of an oligonucleotide having a corresponding sequence of continued 5 to 150 bases, preferably 5 to 60 bases, and more preferably 10 to 40 bases, among nucleotide sequences of a cDNA and a genomic DNA of the GDP-fucose synthase, the α1,6-fucose modifying enzyme or the GDP-fucose transport protein by synthesizing an oligonucleotide which corresponds to a sequence complementary to the oligonucleotide (antisense oligonucleotide) or a ribozyme comprising the oligonucleotide sequence.

The oligonucleotide includes oligo RNA and derivatives of the oligonucleotide (hereinafter referred to as "oligonucleotide derivatives").

The oligonucleotide derivatives includes oligonucleotide derivatives in which a phosphodiester bond in the oligonucleotide is converted into a phosphorothioate bond, an oligonucleotide derivative in which a phosphodiester bond in the oligonucleotide is converted into an N3'-P5' phosphoamidate bond, an oligonucleotide derivative in which ribose and a phosphodiester bond in the oligonucleotide are converted into a peptide-nucleic acid bond, an oligonucleotide derivative in which uracil in the oligonucleotide is substituted with C-5 propynyluracil, an oligonucleotide derivative in which uracil in the oligonucleotide is substituted with C-5 thiazoleuracil, an oligonucleotide derivative in which cytosine in the oligonucleotide is substituted with C-5 propynylcytosine, an oligonucleotide derivative in which cytosine in the oligonucleotide is substituted with phenoxazine-modified cytosine, an oligonucleotide derivative in which ribose in the oligonucleotide is substituted with 2'-O-propylribose and an oligonucleotide derivative in which ribose in the oligonucleotide is substituted with 2'-methoxyethoxyribose [*Cell Technology (Saibo Kogaku)*, 16, 1463 (1997)].

(b) Preparation of Host Cell by Homologous Recombination

The host cell can be prepared by targeting a gene encoding the GDP-fucose synthase, the α1,6-fucose modifying enzyme or the GDP-fucose transport protein and modifying the target gene on chromosome through a homologous recombination technique.

The target gene on the chromosome can be modified by using a method described in *Manipulating the Mouse Embryo, A Laboratory Manual*, Second Edition, Cold Spring Harbor Laboratory Press (1994) (hereinafter referred to as "*Manipulating the Mouse Embryo, A Laboratory Manual*"); *Gene Targeting, A Practical Approach*, IRL Press at Oxford University Press (1993); *Biomanual Series 8, Gene Targeting, Preparation of Mutant Mice using ES*, Yodo-sha (1995) (hereinafter referred to as "*Preparation of Mutant Mice using ES Cells*"); or the like, for example, as follows.

A genomic DNA encoding the GDP-fucose synthase, the α1,6-fucose modifying enzyme or the GDP-fucose transport protein is prepared.

Based on the nucleotide sequence of the genomic DNA, a target vector is prepared for homologous recombination of a target gene to be modified (e.g., structural gene of the GDP-fucose synthase, the α1,6-fucose modifying enzyme or the GDP-fucose transport protein or a promoter gene).

The host cell can be produced by introducing the prepared target vector into a host cell and selecting a cell in which homologous recombination occurred between the target gene and target vector.

As the host cell, any cell such as yeast, an animal cell, an insect cell or a plant cell can be used, so long as it has a gene encoding the GDP-fucose synthase, the α1,6-fucose modifying enzyme or the GDP-fucose transport protein. Examples include the host cells described in the following item 3.

The method for preparing a genomic DNA encoding the GDP-fucose synthase, the α1,6-fucose modifying enzyme or the GDP-fucose transport protein includes the methods described in "Preparation method of genomic DNA" in the item 1(1)(a) and the like.

The target vector for the homologous recombination of the target gene can be prepared in accordance with a method described in *Gene Targeting, A Practical Approach*, IRL Press at Oxford University Press (1993), *Preparation of Mutant Mice using ES Cells*; or the like. The target vector can be used as either a replacement type or an insertion type.

For introducing the target vector into various host cells, the methods for introducing recombinant vectors suitable for various host cells described in the following item 3, can be used.

The method for efficiently selecting a homologous recombinant includes a method such as the positive selection, promoter selection, negative selection or polyA selection described in *Gene Targeting, A Practical Approach*, IRL Press at Oxford University Press (1993); *Preparation of Mutant Mice using ES Cells*; or the like. The method for selecting the homologous recombinant of interest from the selected cell lines includes the Southern hybridization method for genomic DNA (*Molecular Cloning*, Second Edition), PCR [*PCR Protocols*, Academic Press (1990)], and the like.

(c) Preparation of Host Cell by RDO Method

The host cell of the present invention can be prepared by targeting a gene encoding the GDP-fucose synthase, the α1,6-fucose modifying enzyme or the GDP-fucose transport protein according to an RDO method, for example, as follows.

A cDNA or a genomic DNA of the GDP-fucose synthase, the α1,6-fucose modifying enzyme or the GDP-fucose transport protein is prepared.

The nucleotide sequence of the prepared cDNA or genomic DNA is determined.

Based on the determined DNA sequence, an RDO construct of an appropriate length comprising a part encoding the GDP-fucose synthase, the α1,6-fucose modifying enzyme or the GDP-fucose transport protein, a part of its untranslated region or a part of an intron, is designed and synthesized.

The host cell of the present invention can be obtained by introducing the synthesized RDO into a host cell and then selecting a transformant in which a mutation occurred in the target enzyme, i.e., the GDP-fucose synthase, the α1,6-fucose modifying enzyme or the GDP-fucose transport protein.

As the host cell, any cell such as yeast, an animal cell, an insect cell or a plant cell can be used, so long as it has a gene encoding the target GDP-fucose synthase, α1,6-fucose modifying enzyme or GDP-fucose transport protein. Examples include the host cells which will be described in the following item 3.

The method for introducing RDO into various host cells includes the methods for introducing recombinant vectors suitable for various host cells described in the following item 3.

The method for preparing cDNA of the GDP-fucose transport protein includes the methods described in "Preparation method of cDNA" in the item 1(1)(a) and the like.

The method for preparing a genomic DNA of the GDP-fucose synthase, α1,6-fucose modifying enzyme or the GDP-fucose transport protein includes the methods in "Preparation method of genomic DNA" described in the item 1(1)(a) and the like.

The nucleotide sequence of the DNA can be determined by digesting it with appropriate restriction enzymes, cloning the fragments into a plasmid such as pBluescript SK(−) (manufactured by Stratagene), subjecting the clones to the reaction generally used as a method for analyzing a nucleotide sequence such as the dideoxy method of Sanger et al. [*Proc. Natl. Acad. Sci. USA,* 74, 5463 (1977)] or the like, and then analyzing the clones using an automatic nucleotide sequence analyzer such as A.L.F. DNA Sequencer (manufactured by Pharmacia) or the like.

The RDO can be prepared in the usual method or by using a DNA synthesizer.

The method for selecting a cell in which a mutation occurred, by introducing the RDO into the host cell, in the gene encoding the targeting enzyme, the GDP-fucose synthase, the α1,6-fucose modifying enzyme or the GDP-fucose transport protein includes the methods for directly detecting mutations in chromosomal genes described in *Molecular Cloning*, Second Edition, *Current Protocols in Molecular Biology* and the like.

Furthermore, the method described in the item 1(1)(a) for selecting a transformant based on the activity of the GDP-fucose synthase, the α1,6-fucose modifying enzyme or the GDP-fucose transport protein and the method for selecting a transformant based on the sugar chain structure of a glycoprotein on the cell membrane described in the following item 1(5) can also be used.

The construct of the RDO can be designed in accordance with the methods described in *Science*, 273, 1386 (1996), *Nature Medicine*, 4, 285 (1998), *Hepatology*, 25, 1462 (1997); *Gene Therapy*, 5, 1960 (1999); *J. Mol. Med.*, 75, 829 (1997), *Proc. Natl. Acad. Sci. USA*, 96, 8774 (1999); *Proc. Natl. Acad. Sci. USA*, 96, 8768 (1999); *Nuc. Acids. Res*, 27, 1323 (1999); *Invest. Dematol.*, 111, 1172 (1998); *Nature Biotech.*, 16, 1343 (1998), *Nature Biotech.*, 18, 43 (2000); *Nature Biotech.*, 18, 555 (2000); and the like.

(d) Preparation of Host Cell by RNAi Method

The host cell of the present invention can be prepared by targeting a gene encoding the GDP-fucose synthase, the α1,6-fucose modifying enzyme or the GDP-fucose transport protein according to the RNAi (RNA interference) method, for example, as follows.

A cDNA encoding the GDP-fucose synthase, the α1,6-fucose modifying enzyme or the GDP-fucose transport protein is prepared.

The nucleotide sequence of the prepared cDNA is determined.

Based on the determined DNA sequence, an RNAi gene construct of an appropriate length comprising a part of DNA encoding the GDP-fucose synthase, the α1,6-fucose modifying enzyme or the GDP-fucose transport protein or a part of its untranslated region, is designed.

In order to express the RNAi gene in a cell, a recombinant vector is prepared by inserting a fragment or full length of the prepared DNA into downstream of the promoter of an appropriate expression vector, A transformant is obtained by introducing the recombinant vector into a host cell suitable for the expression vector.

The host cell can be obtained by selecting a transformant based on the activity of the GDP-fucose synthase, the α1,6-fucose modifying enzyme or the GDP-fucose transport protein, or the sugar chain structure of the produced antibody molecule or of a glycoprotein on the cell membrane.

As the host cell, any cell such as yeast, an animal cell, an insect cell or a plant cell can be used, so long as it has a gene encoding the target GDP-fucose synthase, α1,6-fucose modifying enzyme or GDP-fucose transport protein. Examples include host cells described in the following item 3.

As the expression vector, a vector which is autonomously replicable in the host cell or can be integrated into the chromosome and comprises a promoter at such a position that the designed RNAi gene can be transferred is used. Examples include the expression vectors transcribed by polymerase III described in the following item 3.

As the method for introducing a gene into various host cells, the methods for introducing recombinant vectors suitable for various host cells, which will be described in the following item 3, can be used.

The method for selecting a transformant based on the activity having the GDP-fucose synthase, the α1,6-fucose modifying enzyme or the GDP-fucose transport protein includes the methods described in the item 1(1)(a).

The method for selecting a transformant based on the sugar chain structure of a glycoprotein on the cell membrane includes the methods which will be described in the following item 1(5). The method for selecting a transformant based on the sugar chain structure of a produced antibody molecule includes the methods which will be described in the following item 5 or 6.

The method for preparing cDNA of the GDP-fucose synthase, the α1,6-fucose modifying enzyme or the GDP-fucose transport protein includes the methods described in "Preparation method of cDNA" in the item 1(1)(a) and the like.

In addition, the host cell of the present invention can also be obtained without using an expression vector, by directly introducing an RNAi gene designed based on the nucleotide sequence encoding the GDP-fucose synthase, the α1,6-fucose modifying enzyme or the GDP-fucose transport protein.

The RNAi gene can be prepared in the usual method or by using a DNA synthesizer.

The RNAi gene construct can be designed in accordance with the methods described in *Nature*, 391, 806 (1998), *Proc. Natl. Acad. Sci. USA*, 95, 15502 (1998), *Nature*, 395, 854 (1998); *Proc. Natl. Acad. Sci. USA*, 96, 5049 (1999); *Cell*, 95, 1017 (1998), *Proc. Natl. Acad. Sci. USA*, 96, 1451 (1999), *Proc. Natl. Acad. Sci. USA*, 95, 13959 (1998); *Nature Cell Biol.*, 2, 70 (2000); and the like.

(e) Preparation of Host Cell by Method Using Transposon

The host cell can be prepared by selecting a mutant based on the activity of the GDP-fucose synthase, the α1,6-fucose modifying enzyme or the GDP-fucose transport protein or the sugar chain structure of a produced antibody molecule or of a glycoprotein on the cell membrane by using a transposon system described in *Nature Genet.*, 25, 35 (2000) or the like.

The transposon system is a system in which a mutation is induced by randomly inserting an exogenous gene into chromosome, wherein an exogenous gene interposed between transposons is generally used as a vector for inducing a mutation, and a transposase expression vector for randomly inserting the gene into chromosome is introduced into the cell at the same time.

Any transposase can be used, so long as it is suitable for the sequence of the transposon to be used.

As the exogenous gene, any gene can be used, so long as it can induce a mutation in the DNA of a host cell.

As the host cell, any cell such as yeast, an animal cell, an insect cell or a plant cell can be used, so long as it has a gene encoding the targeting GDP-fucose synthase, α1,6-fucose modifying enzyme or GDP-fucose transport protein. Examples include the host cells described in the following item 3. For introducing the gene into various host cells, the method for introducing recombinant vectors suitable for various host cells, which will be described in the following item 3, can be used.

The method for selecting a mutant based on the activity of the GDP-fucose synthase, the α1,6-fucose modifying enzyme or the GDP-fucose transport protein includes the methods described above in the item 1(1)(a).

The method for selecting a mutant based on the sugar chain structure of a produced antibody molecule includes the methods be described in the following item 1(5). The method for selecting a transformant based on the sugar chain structure of a produced antibody molecule includes the methods described in the following item 5 or 6.

(2) Method for Introducing Dominant Negative Mutant of Enzyme

The host cell can be prepared by targeting a gene encoding the GDP-fucose synthase, the α1,6-fucose modifying enzyme or the GDP-fucose transport protein according to a technique for introducing a dominant negative mutant of the protein. The GDP-fucose synthase includes GMD, Fx, GFPP, fucokinase and the like. The α1,6-fucose modifying enzyme includes α1,6-fucosyltransferase, α-L-fucosidase and the like. The GDP-fucose transport protein includes GDP-fucose transporter and the like.

The enzymes catalyze specific reactions having substrate specificity, and dominant negative mutants of a gene encoding the enzymes can be prepared by disrupting the active center of the enzymes which catalyze the catalytic activity having substrate specificity. The method for preparing a dominant negative mutant is specifically described as follows with reference to GMD among the target enzymes.

As a result of the analysis of the three-dimensional structure of *E. coli*-derived GMD, it has been found that 4 amino acids (threonine at position 133, glutamic acid at position 135, tyrosine at position 157 and lysine at position 161) have an important function on the enzyme activity [*Structure*, 8, 2 (2000)]. That is, when mutants were prepared by substituting the 4 amino acids with other different amino acids based on the three-dimensional structure information, the enzyme activity of all of the mutants was significantly decreased. On the other hand, changes in the ability of mutant GMD to bind to GMD coenzyme NADP or its substrate GDP-mannose were hardly observed in the mutants. Accordingly, a dominant negative mutant can be prepared by substituting the 4 amino acids which control the enzyme activity of GMD. A dominant negative mutant can be prepared by comparing the homology and predicting the three-dimensional structure using the amino acid sequence information based on the results of the *E coli*-derived GMD. Such a gene into which amino acid substitution is introduced can be prepared by the site-directed mutagenesis described in *Molecular Cloning*, Second Edition, *Current Protocols in Molecular Biology* or the like.

The host cell can be prepared by using the prepared dominant negative mutant gene of the target enzyme according to the method described in *Molecular Cloning*, Second Edition, *Current Protocols in Molecular Biology, Manipulating the Mouse Embryo*, Second Edition or the like, for example, as follows.

A gene encoding the dominant negative mutant (hereinafter referred to as "dominant negative mutant gene") of the GDP-fucose synthase, the α1,6-fucose modifying enzyme or the GDP-fucose transport protein is prepared.

Based on the full length DNA of the prepared dominant negative mutant gene, a DNA fragment of an appropriate length containing a part encoding the protein is prepared, if necessary.

A recombinant vector is prepared by inserting the DNA fragment or full length DNA into downstream of the promoter of an appropriate expression vector.

A transformant is obtained by introducing the recombinant vector into a host cell suitable for the expression vector.

The host cell can be prepared by selecting a transformant based on the activity of the GDP-fucose synthase, the α1,6-fucose transport protein or the GDP-fucose transport protein, or the sugar chain structure of a produced antibody molecule or of a glycoprotein on the cell membrane.

As the host cell, any cell such as yeast, an animal cell, an insect cell or a plant cell can be used, so long as it has a gene encoding the GDP-fucose synthase, the α1,6-fucose transport protein or the GDP-fucose transport protein, Examples include the host cells described in the following item 3.

As the expression vector, a vector which is autonomously replicable in the host cell or can be integrated into the chromosome and comprises a promoter at a position where transcription of the DNA encoding the dominant negative mutant of interest can be effected is used. Examples include the expression vectors which will be described in the following item 3.

For introducing the gene into various host cells, the methods for introducing recombinant vectors suitable for various host cells, which will be described in the following item 3, can be used.

The method for selecting a mutant based on the activity of the GDP-fucose synthase, the α1,6-fucose transport protein or the GDP-fucose transport protein or the method for selecting a mutant based on the sugar chain structure of a glycoprotein on the cell membrane includes the methods be described in item 1(1)(a).

The method for selecting a mutant based on the sugar chain structure of a produced antibody molecule includes the methods described in the following item 1(5). The method for selecting a transformant based on the sugar chain structure of a produced antibody molecule includes the methods described in the following item 5 or 6.

(3) Method for Introducing Mutation into Enzyme

The host cell of the present invention can be prepared by introducing a mutation into a gene encoding the GDP-fucose synthase, the α1,6-fucose transport protein or the GDP-fucose transport protein, and then by selecting a clone of interest in which the mutation occurred in the enzyme.

The GDP-fucose synthase includes GMD, Fx, GFPP, fucokinase and the like. The α1,6-fucose modifying enzyme includes α1,6-fucosyltransferase, α-L-fucosidase and the like. The GDP-fucose transport protein includes GDP-fucose transporter and the like.

The method for introducing mutation into an enzyme includes 1) a method in which a desired clone is selected from mutants obtained by a mutation-inducing treatment of a parent cell line with a mutagen or spontaneously generated mutants, based on the activity of the GDP-fucose synthase, the α1,6-fucose transport protein or the GDP-fucose transport protein, 2) a method in which a desired clone is selected from mutants obtained by a mutation-inducing treatment of a parent cell line with a mutagen or spontaneously generated mutants, based on the sugar chain structure of a produced antibody molecule, 3) a method in which a desired clone is selected from mutants obtained by a mutation-inducing treatment of a parent cell line with a mutagen or spontaneously generated mutants, based on the sugar chain structure of a glycoprotein on the cell membrane, and the like.

As the mutation-inducing treatment, any treatment can be used, so long as it can induce a point mutation or a deletion or frame shift mutation in the DNA of cells of the parent cell line.

Examples include treatment with ethyl nitrosourea, nitrosoguanidine, benzopyrene or an acridine pigment and treatment with radiation. Also, various alkylating agents and carcinogens can be used as mutagens. The method for allowing a mutagen to act upon cells includes the methods described in *Tissue Culture Techniques*, 3rd edition (Asakura Shoten), edited by Japanese Tissue Culture Association (1996), *Nature Genet.*, 24, 314 (2000) and the like.

The spontaneously generated mutant includes mutants which are spontaneously formed by continuing subculture under general cell culture conditions without applying special mutation-inducing treatment.

The method for measuring the activity of the GDP-fucose synthase, the α1,6-fucose transport protein or the GDP-fucose transport protein includes the methods described above in the item 1(1)(a). The method for discriminating the sugar chain structure of a glycoprotein on the cell membrane includes the methods described in the following item 1(5).

(4) Method for Inhibiting Transcription and/or Translation of Enzyme

The host cell of the present invention can be prepared by targeting a gene encoding the GDP-fucose synthase or the α1,6-fucose modifying enzyme or the GDP-fucose transport protein and inhibiting transcription and/or translation of the target gene according to the antisense RNA/DNA technique [*Bioscience and Industry*, 50, 322 (1992); *Chemistry*, 46, 681 (1991); *Biotechnology*, 2, 358 (1992); *Trends in Biotechnology*, 10, 87 (1992); *Trends in Biotechnology*, 10, 152 (1992), *Cell Engineering*, 16, 1463 (1997)], the triple helix technique [*Trends in Biotechnology*, 10, 132 (1992)] or the like.

The GDP-fucose synthase includes GMD, Fx, GFPP, fucokinase and the like. The α1,6-fucose modifying enzyme includes α1,6-fucosyltransferase, α-L-fucosidase and the like. The GDP-fucose transport protein includes GDP-fucose transporter and the like.

(5) Method for Selecting Clone Resistant to Lectin which Recognizes Sugar Chain Structure in which 1-Position of Fucose is Bound to 6-Position of N-Acetylglucosamine in the Reducing End through α-Bond in the N-Glycoside-Linked Sugar Chain The host cell can be prepared by using a method for selecting a clone resistant to a lectin which recognizes a sugar chain structure in which 1-position of fucose is bound to 6-position of N-acetylglucosamine in the reducing end through α-bond in the N-glycoside-linked sugar chain.

The method for selecting a clone resistant to a lectin which recognizes a sugar chain structure in which 1-position of fucose is bound to 6-position of N-acetylglucosamine in the reducing end through α-bond in the N-glycoside-linked sugar chain includes the methods using lectin described in *Somatic Cell Mol. Genet*, 12, 51 (1986) and the like.

As the lectin, any lectin can be used, so long as it is a lectin which recognizes a sugar chain structure in which 1-position of fucose is bound to 6-position of N-acetylglucosamine in the reducing end through α-bond in the N-glycoside-linked sugar chain. Examples include a *Lens culinaris* lectin LCA (lentil agglutinin derived from *Lens culinaris*), a pea lectin PSA (pea lectin derived from *Pisum sativum*), a broad bean lectin VFA (agglutinin derived from *Vicia faba*), an *Aleuria aurantia* lectin AAL (lectin derived from *Aleuria aurantia*) and the like.

Specifically, the clone of the present invention resistant to a lectin which recognizes a sugar chain structure in which 1-position of fucose is bound to 6-position of N-acetylglucosamine in the reducing end through α-bond in the N-glycoside-linked sugar chain can be selected by culturing cells for 1 day to 2 weeks, preferably from 1 day to 1 week, using a medium comprising the lectin at a concentration of 1 μg/ml to 1 mg/ml, subculturing surviving cells or picking up a colony and transferring it into a culture vessel, and subsequently continuing the culturing using the lectin-containing medium.

The method for confirming that the cell is a lectin-resistant cell includes a method for confirming expression of the GDP-fucose synthase, α1,6-fucose modifying enzyme or the GDP-fucose transport protein, a method for culturing the cell in a medium to which lectin is directly added and the like. Specifically, when the expression amount of the mRNA of α1,6-fucosyltransferase which is one of α1,6-fucose modifying enzymes in the cell is measured, the decrease of the expression of mRNA demonstrates that the cell is a lectin-resistant cell.

2. Preparation of Transgenic Non-Human Animal or Plant or the Progenies

The antibody composition of the present invention can be prepared by using a transgenic non-human animal or plant or the progenies thereof in which a genomic gene is modified in such a manner that the activity of the GDP-fucose synthase, the α1,6-fucose modifying enzyme or the GDP-fucose transport protein is decreased or deleted. The transgenic non-human animal or plant or the progenies thereof can be prepared by targeting a gene encoding the above protein according to the method similar to that in the item 1.

In a transgenic non-human animal, the embryonic stem cell in which the activity of the GDP-fucose synthase, the α1,6-fucose modifying enzyme or the GDP-fucose transport protein is decreased or deleted can be prepared by applying the method similar to that in the item 1 to an embryonic stem cell of the intended non-human animal such as cattle, sheep, goat, pig, horse, mouse, rat, fowl, monkey or rabbit.

Specifically, a mutant clone is prepared in which a gene encoding the GDP-fucose synthase, the α1,6-fucose modifying enzyme or the GDP-fucose transport protein is inactivated or substituted with any sequence, by a known homologous recombination technique [e.g., *Nature*, 326, 6110, 295 (1987); *Cell*, 51, 3, 503 (1987); etc.]. Using the prepared stem cell (e.g., the mutant clone), a chimeric individual comprising an embryonic stem cell clone and a normal cell can be prepared by an injection chimera method into blastocyst of fertilized egg of an animal or by an aggregation chimera method. The chimeric individual is crossed with a normal individual, so that a transgenic non-human animal in which the activity of the GDP-fucose synthase, the α1,6-fucose modifying enzyme or the GDP-fucose transport protein is decreased or deleted in the whole body cells can be obtained.

The target vector for the homologous recombination of the target gene can be prepared in accordance with a method described in *Gene Targeting, A Practical Approach*, IRL Press at Oxford University Press (1993); *Biomanual Series 8, Gene Targeting, Preparation of Mutant Mice using ES Cells*, Yodo-sha (1995) or the like. The target vector can be used as any of a replacement type, an insertion type, a gene trap type and the like.

As the method for introducing the target vector into the embryonic stem cell, any method can be used, so long as it can introduce DNA into an animal cell. Examples include electroporation [*Cytotechnology*, 3, 133 (1990)], the calcium phosphate method (Japanese Published Examined Patent Application No. 227075/90), the lipofection method [*Proc. Natl. Acad. Sci. USA*, 84, 7413 (1987)], the injection method [*Manipulating the Mouse Embryo, A Laboratory Manual*], a method using particle gun (gene gun) (Japanese Patent No. 2606856, Japanese Patent No. 2517813), the DEAE-dextran method [*Biomanual Series 4-Gene Transfer and Expression Analysis* (Yodo-sha), edited by Takashi Yokota and Kenichi Arai (1994)], the virus vector method [*Manipulating Mouse Embryo*, Second Edition] and the like.

The method for efficiently selecting a homologous recombinant includes a method such as the positive selection, promoter selection, negative selection or polyA selection described in *Gene Targeting, A Practical Approach*, IRL Press at Oxford University Press (1993); *Biomanual Series* 8, *Gene Targeting, Preparation of Mutant Mice using ES Cells*, Yodo-sha (1995); or the like. Specifically, in the case of the target vector containing hprt gene, it is introduced into the hprt gene-defected embryonic stem cell, the embryonic stem cell is cultured in a medium containing aminopterin, hypoxanthine and thymidine, and positive selection which selects the homologous recombinant of the hprt gene can be carried out by selecting a homogenous recombinant containing an aminopterin-resistant clone. In the case of the target vector containing a neomycin-resistant gene, the vector-introduced embryonic stem cell is cultured in a medium containing G418, and positive selection can be carried out by selecting a homogenous recombinant containing a neomycin-resistant gene. In the case of the target vector containing DT gene, the vector-introduced embryonic stem cell is cultured, and negative selection being capable of selecting a DT gene-free homogenous recombinant can be carried out by selecting the grown clone (in the recombinants introduced into a chromosome at random rather than the homogenous recombination, since the DT gene is expressed while integrated in the chromosome, they cannot grow due to the toxicity of DT). The method for selecting the homogenous recombinant of interest among the selected clones include the Southern hybridization for genomic DNA (*Molecular Cloning*, Second Edition), PCR [*PCR Protocols*, Academic Press (1990)] and the like.

When the embryonic stem cell is introduced into a fertilized egg by using an aggregation chimera method, in general, a fertilized egg at the development stage before 8-cell stage is preferably used. When the embryonic stem cell is introduced into a fertilized egg by using an injection chimera method, in general, it is preferred that a fertilized egg at the development stage from 8-cell stage to blastocyst stage is used.

When the fertilized egg is transplanted into a female mouse, it is preferred that a fertilized egg obtained from a pseudopregnant female mouse in which fertility is induced by mating with a male non-human mammal which is subjected to vasoligation is artificially transplanted or implanted. Although the psuedopregnant female mouse can be obtained by natural mating, the pseudopregnant female mouse in which fertility is induced can be obtained by mating with a male mouse after administration of a luteinizing hormone-releasing hormone (hereinafter referred to as "LHRH") or its analogue thereof. The analogue of LHRH includes [3,5-Dil-Tyr5]-LHWL [Gln8]-LHRH, (D-Ala61-LHRH, des-Gly10-[D-His(Bzl)6]-LHRH ethylamide and the like.

Also, a fertilized egg cell in which the activity of the GDP-fucose synthase, the ($\alpha$1,6-fucose modifying enzyme or the GDP-fucose transport protein is decreased or deleted can be prepared by applying the method similar to that in the item 1 to fertilized egg of a non-human animal of interest such as cattle, sheep, goat, pig, horse, mouse, rat, fowl, monkey, rabbit or the like.

A transgenic non-human animal in which the activity of the GDP-fucose synthase, the $\alpha$1,6-fucose modifying enzyme or the GDP-fucose transport protein is decreased or deleted can be prepared by transplanting the prepared fertilized egg cell into the oviduct or uterus of a pseudopregnant female using the embryo transplantation method described in *Manipulating Mouse Embryo*, Second Edition or the like, followed by childbirth by the animal.

In a transgenic plant, the callus in which the activity of the GDP-fucose synthase, the $\alpha$1,6-fucose modifying enzyme or the GDP-fucose transport protein is decreased or deleted can be prepared by applying the method similar to that in the item 1 to a callus or cell of the plant of interest.

A transgenic plant in which the activity of the GDP-fucose synthase, the ($\alpha$1,6-fucose modifying enzyme or the GDP-fucose transport protein is decreased or deleted can be prepared by culturing the prepared callus in a medium comprising auxin and cytokinin to redifferentiate it in accordance with a known method [*Tissue Culture (Soshiki Baiyo)*, 20 (1994); *Tissue Culture (Soshiki Baiyo)*, 21 (1995); *Trends in Biotechnology*, 15, 45 (1997)].

3. Method for Producing Antibody Composition

The antibody composition can be obtained by expressing it in a host cell using the methods described in *Molecular Cloning*, Second Edition; *Current Protocols in Molecular Biology, Antibodies, A Laboratory Manual*, Cold Spring Harbor Laboratory, 1988 (hereinafter sometimes referred to as "*Antibodies*"); *Monoclonal Antibodies: Principles and Practice*, Third Edition, Acad. Press, 1993 (hereinafter sometimes referred to as "*Monoclonal Antibodies*"); and *Antibody Engineering, A Practical Approach*, IRL Press at Oxford University Press (hereinafter sometimes referred to as "*Antibody Engineering*"), for example, as follows.

A full length cDNA encoding an antibody molecule is prepared, and a DNA fragment of an appropriate length comprising a DNA encoding the antibody molecule is prepared.

A recombinant vector is prepared by inserting the DNA fragment or the full length cDNA into downstream of the promoter of an appropriate expression vector.

A transformant which produces the antibody molecule can be obtained by introducing the recombinant vector into a host cell suitable for the expression vector.

As the host cell, the host cell of yeast, an animal cell, an insect cell, a plant cell or the like which can express the gene of interest described in the above 1 is used.

As the expression vector, a vector which is autonomously replicable in the host cell or can be integrated into the chromosome and comprises a promoter at such a position that the DNA encoding the antibody molecule of interest can be transferred is used.

The cDNA can be prepared from a human or non-human tissue or cell using, e.g., a probe primer specific for the antibody molecule of interest according to the methods described in "Preparation method of cDNA" in the item 1(1)(a).

When yeast is used as the host cell, the expression vector includes YEP13 (ATCC 37115), YEp24 (ATCC 37051), YCp50 (ATCC 37419) and the like.

Any promoter can be used, so long as it can function in yeast. Examples include a promoter of a gene of the glycolytic pathway such as a hexose kinase gene, PHO5 promoter, PGK promoter, GAP promoter, ADH promoter, gal 1 promoter, gal 10 promoter, heat shock protein promoter, MF$\alpha$1 promoter, CUP 1 promoter and the like.

The host cell includes microorganisms belonging to the genus Saccharomyces, the genus Schizosaccharomyces, the genus Kluvyeromyces, the genus Trichosporon, the genus Schwanniomyces and the like, such as *Saccharomyces cerevisiae, Schizosaccharomyces pombe, Kluyveromyces lactis, Trichosporon pullulans* and *Schwanniomyces alluvius*.

As the method for introducing the recombinant vector, any method can be used, so long as it can introduce DNA into yeast. Examples include electroporation (*Methods in Enzymology*, 14, 182 (1990)], spheroplast method [*Proc. Natl. Acad. Sci. USA*, 84, 1929 (1978)], lithium acetate method [*J. Bacteriol.*, 153, 163 (1983)], a method described in *Proc. Natl. Acad. Sci. USA*, 75, 1929 (1978) and the like.

When an animal cell is used as the host cell, the expression vector includes pcDNAI, pcDM8 (available from Funakoshi), pAGE107 [Japanese Published Examined Patent Application No. 22979/91; *Cytotechnology,* 3, 133 (1990)], pAS3-3 (Japanese Published Examined Patent Application No. 227075/90), pCDM8 [*Nature,* 329, 840 (1987)], pCD-NAI/Amp (manufactured by Invitrogen), pREP4 (manufactured by Invitrogen), pAGE103 [*J. Biochemistry,* 101, 1307 (1987)], pAGE210 and the like.

Any promoter can be used, so long as it can function in an animal cell. Examples include a promoter of IE (immediate early) gene derived from cytomegalovirus (CMV), an early promoter derived from SV40, a promoter derived from retrovirus, a promoter derived from metallothionein, a heat shock promoter, an SRα promoter and the like. Also, an enhancer of the IE gene derived from human CMV may be used together with the promoter.

The host cell includes a human cell such as Namalwa cell, a monkey cell such as COS cell, a Chinese hamster cell such as CHO cell or HBT5637 (Japanese Published Examined Patent Application No. 299/88), a rat myeloma cell, a mouse myeloma cell, a cell derived from Syrian hamster kidney, an embryonic stem cell, a fertilized egg cell and the like.

As the method for introducing the recombinant vector, any method can be used, so long as it can introduce DNA into an animal cell. Examples include electroporation [*Cytotechnology*, 3, 133 (1990)], the calcium phosphate method (Japanese Published Examined Patent Application No. 227075/90), the lipofection method [*Proc. Natl. Acad. Sci. USA,* 84, 7413 (1987)], the injection method [*Manipulating the Mouse Embryo, A Laboratory Manual*], a method by using particle gun (gene gun) (Japanese Patent No. 2606856, Japanese Patent No. 2517813), the DEAE-dextran method [*Biomanual Series 4—Gene Transfer and Expression Analysis* (Yodosha), edited by Takashi Yokota and Kenichi Arai (1994)], the virus vector method [*Manipulating Mouse Embryo*, Second Edition] and the like.

When an insect cell is used as the host, the protein can be expressed by the method described in *Current Protocols in Molecular Biology, Baculovirus Expression Vectors, A Laboratory Manual*, W. H. Freeman and Company, New York (1992), *Bio/Technology,* 6, 47 (1988) or the like.

That is, the protein can be expressed by co-introducing a recombinant gene-introducing vector and a baculovirus into an insect cell to obtain a recombinant virus in an insect cell culture supernatant and then infecting the insect cell with the recombinant virus.

The gene introducing vector used in the method includes pVL1392, pVL1393, pBlueBacIII (all manufactured by Invitrogen) and the like.

The baculovirus includes *Autographa californica* nuclear polyhedrosis virus which is infected by an insect of the family Barathra.

The insect cell includes *Spodoptera frugiperda* oocytes Sf9 and Sf21 [*Current Protocols in Molecular Biology, Baculovirus Expression Vectors, A Laboratory Manual*, W. H. Freeman and Company, New York (1992)], a *Trichoplusia ni* oocyte High 5 (manufactured by Invitrogen) and the like.

The method for the co-introducing the recombinant gene-introducing vector and the baculovirus for preparing the recombinant virus includes the calcium phosphate method (Japanese Published Examined Patent Application No. 227075/90), the lipofection method [*Proc. Natl. Acad. Sci. USA,* 84, 7413 (1987)] and the like.

When a plant cell is used as the host cell, the expression vector includes Ti plasmid, tobacco mosaic virus and the like.

As the promoter, any promoter can be used, so long as it can function in a plant cell. Examples include cauliflower mosaic virus (CaMV) 35S promoter, rice actin 1 promoter and the like.

The host cell includes plant cells of tobacco, potato, tomato, carrot, soybean, rape, alfalfa, rice, wheat, barley and the like.

As the method for introducing the recombinant vector, any method can be used, so long as it can introduce DNA into a plant cell. Examples include a method using Agrobacterium (Japanese Published Examined Patent Application No. 140885/84, Japanese Published Examined Patent Application No. 70080/85, WO94/00977), electroporation (Japanese Published Examined Patent Application No. 251887/85), a method in which a particle gun (gene gun) is used (Japanese Patent No. 2606856, Japanese Patent No. 2517813) and the like.

As the method for expressing an antibody gene, secretion production, expression of a fusion protein of the Fc region with other protein and the like can be carried out in accordance with the method described in *Molecular Cloning*, Second Edition or the like, in addition to the direct expression.

When a gene is expressed by yeast, an animal cell, an insect cell or a plant cell into which a gene relating to the synthesis of a sugar chain is introduced, an antibody molecule to which a sugar or a sugar chain is added can be obtained depending on the introduced gene.

An antibody composition can be obtained by culturing the obtained transformant in a medium to produce and accumulate the antibody molecule in the culture and then recovering it from the resulting culture. The method for culturing the transformant in a medium can be carried out in accordance with a general method which is used for the culturing of host cells.

As the medium for culturing a transformant obtained by using a yeast cell, as the host, the medium may be either a natural medium or a synthetic medium, so long as it comprises materials such as a carbon source, a nitrogen source and an inorganic salt which can be assimilated by the organism and culturing of the transformant can be efficiently carried out.

As the carbon source, those which can be assimilated by the organism can be used. Examples include carbohydrates such as glucose, fructose, sucrose, molasses containing them, starch and starch hydrolysate; organic acids such as acetic acid and propionic acid; alcohols such as ethanol and propanol; and the like.

The nitrogen source includes ammonia; ammonium salts of inorganic acid or organic acid such as ammonium chloride, ammonium sulfate, ammonium acetate and ammonium phosphate, other nitrogen-containing compounds; peptone; meat extract; yeast extract, corn steep liquor casein hydrolysate; soybean meal soybean meal hydrolysate; various fermented cells and hydrolysates thereof, and the like.

The inorganic salt includes potassium dihydrogen phosphate, dipotassium hydrogen phosphate, magnesium phosphate, magnesium sulfate, sodium chloride, ferrous sulfate, manganese sulfate, copper sulfate, calcium carbonate, and the like.

The culturing is carried out generally under aerobic conditions such as a shaking culture or submerged-aeration stirring culture. The culturing temperature is preferably 15 to 40° C., and the culturing time is generally 16 hours to 7 days. During the culturing, the pH is maintained at 3.0 to 9.0. The pH is adjusted using an inorganic or organic acid, an alkali solution, urea, calcium carbonate, ammonia or the like.

Furthermore, if necessary, an antibiotic such as ampicillin or tetracycline can be added to the medium during the culturing.

When a microorganism transformed with a recombinant vector obtained by using an inducible promoter as the promoter is cultured, an inducer can be added to the medium, if necessary. For example, when a microorganism transformed with a recombinant vector obtained by using lac promoter is cultured, isopropyl-β-D-thiogalactopyranoside can be added to the medium, and when a microorganism transformed with a recombinant vector obtained by using trp promoter is cultured, indoleacrylic acid can be added to the medium.

When a transformant obtained by using an animal cell as the host is cultured, the medium includes generally used RPMI 1640 medium [*The Journal of the American Medical Association*, 199, 519 (1967)], Eagle's MEM medium [*Science*, 122, 501 (1952)], Dulbecco's modified MEM medium [*Virology*, 8, 396 (1959)], 199 medium [*Proceeding of the Society for the Biological Medicine*, 73, 1 (1950)] and Whitten's medium [*Developmental Engineering Experimentation Manual—Preparation of Transgenic Mice* (Kodan-sha), edited by M. Katsuki (1987)], the media to which fetal calf serum, etc. are added, and the like.

The culturing is carried out generally at a pH of 6 to 8 and 30 to 40° C. for 1 to 7 days in the presence of 5% $CO_2$ for 1 to 7 days.

Furthermore, if necessary, an antibiotic such as kanamycin or penicillin can be added to the medium during the culturing.

The medium for culturing a transformant obtained by using an insect cell as the host includes generally used TNM-FR medium (manufactured by Pharmingen), Sf-900 II SFM medium (manufactured by Life Technologies), ExCell 400 and ExCell 405 (both manufactured by JRH Biosciences), Grace's Insect Medium [*Nature*, 195, 788 (1962)] and the like.

The culturing is carried out generally at a medium pH of 6 to 7 and 25 to 30° C. for 1 to 5 days.

Furthermore, if necessary, an antibiotic such as gentamicin can be added to the medium during the culturing.

A transformant obtained by using a plant cell as the host can be cultured as a cell or by differentiating it into a plant cell or organ. The medium for culturing the transformant includes generally used Murashige and Skoog (MS) medium and White medium, wherein the media are added to a plant hormone such as auxin, cytokinin, and the like.

The culturing is carried out generally at a pH of 5 to 9 and 20 to 40° C. for 3 to 60 days.

Furthermore, if necessary, an antibiotic such as kanamycin or hygromycin can be added to the medium during the culturing.

As discussed above, an antibody composition can be produced by culturing a transformant derived from a yeast cell, an animal cell or a plant cell, which comprises a recombinant vector into which a DNA encoding an antibody molecule is inserted, in accordance with a general culturing method, to thereby produce and accumulate the antibody composition, and then recovering the antibody composition from the culture.

As the method for expressing the gene encoding an antibody, secretion production, expression of a fusion protein and the like can be carried out in accordance with the method described in *Molecular Cloning*, Second Edition in addition to the direct expression.

The method for producing an antibody composition includes a method of intracellular expression in a host cell, a method of extracellular secretion from a host cell, and a method of production on a host cell membrane outer envelope. The method can be selected by changing the host cell used or the structure of the antibody composition produced.

When the antibody composition is produced in a host cell or on a host cell membrane outer envelope, it can be positively secreted extracellularly in accordance with the method of Paulson et al. [*J. Biol. Chem.*, 264, 17619 (1989)], the method of Lowe et al. [*Proc. Natl. Acad. Sci. USA*, 86, 8227 (1989), *Genes Develop.*, 4, 1288 (1990)], the methods described in Japanese Published Examined Patent Application No. 336963/93 and Japanese Published Examined Patent Application No. 823021/94 and the like.

That is, an antibody molecule of interest can be positively secreted extracellularly from a host cell by inserting a DNA encoding the antibody molecule and a DNA encoding a signal peptide suitable for the expression of the antibody molecule into an expression vector according to a gene recombination technique, introducing the expression vector into the host cell and then expressing the antibody molecule.

Also, its production amount can be increased in accordance with the method described in Japanese Published Examined Patent Application No. 227075/90 according to a gene amplification system using a dihydrofolate reductase gene.

In addition, the antibody composition can also be produced by using a gene-introduced animal individual (transgenic non-human animal) or a plant individual (transgenic plant) which is constructed by the redifferentiation of an animal or plant cell into which the gene is introduced.

When the transformant is an animal individual or a plant individual, an antibody composition can be produced in accordance with a general method by rearing or cultivating it to thereby produce and accumulate the antibody composition and then recovering the antibody composition from the animal or plant individual.

The method for producing an antibody composition using an animal individual includes a method in which the antibody composition of interest is produced in an animal constructed by introducing a gene in accordance with a known method [*American Journal of Clinical Nutrition*, 63, 639S (1996); *American Journal of Clinical Nutrition*, 63, 627S (1996), *Bio/Technology*, 9, 830 (1991)].

In the case of an animal individual, an antibody composition can be produced by rearing a transgenic non-human animal into which a DNA encoding an antibody molecule is introduced to thereby produce and accumulate the antibody composition in the animal, and then recovering the antibody composition from the animal. The place of the animal where the composition is produced and accumulated includes milk (Japanese Published Examined Patent Application No. 309192/88) and eggs of the animal. As the promoter used in this case, any promoter can be used, so long as it can function in an animal. Preferred examples include mammary gland cell-specific promoters such as a casein promoter, β casein promoter, β lactoglobulin promoter, whey acidic protein promoter and the like.

The method for producing an antibody composition using a plant individual includes a method in which an antibody composition is produced by cultivating a transgenic plant into which a DNA encoding an antibody molecule is introduced by a known method [*Tissue Culture (Soshiki Baiyo)*, 20 (1994); *Tissue Culture (Soshiki Baiyo)*, 21 (1995); *Trends in Biotechnology*, 15, 45 (1997)] to produce and accumulate the antibody composition in the plant, and then recovering the antibody composition from the plant.

Regarding purification of an antibody composition produced by a transformant into which a gene encoding an antibody molecule is introduced, for example, when the antibody composition is intracellularly expressed in a dissolved state, the cells after culturing are recovered by centrifugation, suspended in an aqueous buffer and then disrupted by using ultrasonic oscillator, French press, Manton Gaulin homogenizer, dynomill or the like to obtain a cell-free extract. A purified product of the antibody composition can be obtained from a supernatant obtained by centrifuging the cell-free extract according to a general enzyme isolation purification techniques such as solvent extraction; salting out or desalting with ammonium sulfate; precipitation with an organic solvent; anion exchange chromatography using a resin such as diethylaminoethyl (DEAE)-Sepharose or DLAION BPA-75 (manufactured by Mitsubishi Chemical), cation exchange chromatography using a resin such as S-Sepharose FF (manufactured by Pharmacia), hydrophobic chromatography using a resin such as butyl-Sepharose or phenyl-Sepharose, gel filtration using a molecular sieve; affinity chromatography; chromatofocusing; electrophoresis such as isoelectric focusing, and the like which may be used alone or in combination.

Also, when the antibody composition is expressed intracellularly by forming an insoluble body, the cells are recovered, disrupted and centrifuged in the same manner, and the insoluble body of the antibody composition is recovered as a precipitation fraction. The recovered insoluble body of the antibody composition is solubilized by using a protein denaturing agent. The antibody composition is made into a normal three-dimensional structure by diluting or dialyzing the solubilized solution, and then a purified product of the antibody composition is obtained by the same isolation purification method.

When the antibody composition is secreted extracellularly, the antibody composition or derivatives thereof can be recovered from the culture supernatant. That is, the culture is treated according to a technique such as centrifugation to obtain a soluble fraction, and a purified preparation of the antibody composition can be obtained from the soluble fraction by the same isolation purification method.

The thus obtained antibody composition includes an antibody, the fragment of the antibody, a fusion protein comprising the Fc region of the antibody, and the like.

As an example for obtaining antibody compositions, methods for producing a humanized antibody composition and Fc fusion protein are described below in detail, but other antibody compositions can also be obtained in a manner similar to the method.

A. Preparation of Humanized Antibody Composition (1) Construction of Vector for Expression of Humanized Antibody A vector for expression of humanized antibody is an expression vector for animal cell into which genes encoding CH and CL of a human antibody are inserted, and which can be constructed by cloning each of genes encoding CH and CL of a human antibody into an expression vector for animal cell.

The C regions of a human antibody may be CH and CL of any human antibody. Examples include the C region belonging to IgG1 subclass in the H chain of a human antibody (hereinafter referred to as "hCγ1"), the C region belonging to K class in the L chain of a human antibody (hereinafter referred to as "hCK"), and the like.

As the genes encoding CH and CL of a human antibody, a chromosomal DNA comprising an exon and an intron can be used, and a cDNA can also be used.

As the expression vector for animal cell, any vector can be used, so long as a gene encoding the C region of a human antibody can be inserted thereinto and expressed therein. Examples include pAGE107 [*Cytotechnology*, 3, 133 (1990)], pAGE103 [*J. Biochem.*, 101, 1307 (1987)], pHSG274 [*Gene*, 27, 223 (1984)], pKCR [*Proc Natl. Acad. Sci. USA*, 78, 1527 (1981), PSGI β d2-4 [*Cytotechnology*, 4, 173 (1990)] and the like. The promoter and enhancer in the expression vector for animal cell includes SV40 early promoter and enhancer [*J. Biochem.*, 101, 1307 (1987)], Moloney mouse leukemia virus LTR [*Biochem. Biophys. Res. Commun.*, 149, 960 (1987)], immunoglobulin H chain promoter [*Cell*, 41, 479 (1985)] and enhancer [*Cell*, 33, 717 (1983)], and the like.

The vector for expression of humanized antibody may be either of a type in which genes encoding the H chain and L chain of an antibody exist on separate vectors or of a type in which both genes exist on the same vector (hereinafter referred to as "tandem type"). In respect of easiness of construction of a vector for expression of humanized antibody, easiness of introduction into animal cells, and balance between the expression amounts of the H and L chains consisting of an antibody in animal cells, a tandem type of the vector for expression of humanized antibody is more preferred [*J. Immunol. Methods*, 167, 271 (1994)].

The constructed vector for expression of humanized antibody can be used for expression of a human chimeric antibody and a human CDR-grafted antibody in animal cells.

(2) Preparation Method of cDNA Encoding V Region of Non-Human Animal Antibody cDNAs encoding VH and VL of a non-human animal antibody such as a mouse antibody can be obtained in the following manner.

A cDNA is synthesized from mRNA extracted from a hybridoma cell which produces the mouse antibody of interest. The synthesized cDNA is cloned into a vector such as a phage or a plasmid to obtain a cDNA library. Each of a recombinant phage or recombinant plasmid comprising a cDNA encoding VH and a recombinant phage or recombinant plasmid comprising a cDNA encoding VL is isolated from the library by using a C region part or a V region part of an existing mouse antibody as the probe. Full nucleotide sequences of VH and VL of the mouse antibody of interest on the recombinant phage or recombinant plasmid are determined, and full length amino acid sequences of VH and VL are deduced from the nucleotide sequences.

As the non-human animal, any animal such as mouse, rat, hamster or rabbit can be used, so long as a hybridoma cell can be produced therefrom.

The method for preparing a total RNA from a hybridoma cell includes the guanidine thiocyanate-cesium trifluoroacetate method [*Methods in Enzymology*, 154, 3 (1987)] and the like, and the method for preparing mRNA from total RNA includes an oligo(dT)-immobilized cellulose column method (*Molecular Cloning*, Second Edition) and the like. In addition, a kit for preparing mRNA from a hybridoma cell includes Fast Track mRNA Isolation Kit (manufactured by Invitrogen), Quick Prep mRNA Purification Kit (manufactured by Pharmacia) and the like.

The method for synthesizing a cDNA and preparing a cDNA library includes the usual methods (*Molecular Cloning*, Second Edition, *Current Protocols in Molecular Biology*, Supplement 1-34), methods using a commercially available kit such as SuperScript™, Plasmid System for cDNA Synthesis and Plasmid Cloning (manufactured by GEBCO BRL) or ZAP-cDNA Synthesis Kit (manufactured by Stratagene), and the like.

In preparing the cDNA library, the vector into which a cDNA synthesized by using mRNA extracted from a hybridoma cell as the template is inserted may be any vector, so long as the cDNA can be inserted. Examples include ZAP Express [*Strategies*, 5, 58 (1992)], pBluescript II SK(+) (*Nucleic Acids Research*, 17, 9494 (1989)1, λzapII (manufactured by Stratagene), λgt10 and λgt11 [*DNA Cloning, A Practical Approach*, I, 49 (1985)], Lambda BlueMid (manufactured by Clontech), λExCell, pT7T3 18U (manufactured by Pharmacia), pcD2 [*Mol. Cell. Biol.*, 3, 280 (1983)], pUC18 [Gene, 33, 103 (1985)] and the like.

As *Escherichia coli* into which the cDNA library constructed from a phage or plasmid vector is introduced, any *Escherichia coli* can be used, so long as the cDNA library can be introduced, expressed and maintained. Examples include XL1-Blue MRF' [*Strategies*, 5, 81 (1992)], C600 [*Genetics*, 39, 440 (1954)], Y1088 and Y1090 [*Science*, 222, 778 (1983)], NM522 [*J. Mol. Biol*, 166, 1 (1983)], K802 (J. Mol. Biol., 16, 118 (1966)], JM105 [Gene, 38, 275 (1985)] and the like.

As the method for selecting a cDNA clone encoding VH and VL of a non-human animal antibody from the cDNA library, a colony hybridization or a plaque hybridization using an isotope- or fluorescence-labeled probe can be used (*Molecular Cloning*, Second Edition). The cDNA encoding VH and VL can also be prepared by preparing primers and carrying out polymerase chain reaction (hereinafter referred to as "PCR"; *Molecular Cloning*, Second Edition; *Current Protocols in Molecular Biology*, Supplement 1-34) using a cDNA synthesized from mRNA or a cDNA library as the template.

The nucleotide sequences of the cDNAs can be determined by digesting the selected cDNAs with appropriate restriction enzymes, cloning the fragments into a plasmid such as pBluescript SK(−) (manufactured by Stratagene), carrying out the reaction of a generally used nucleotide sequence analyzing method such as the dideoxy method of Sanger et al. [*Proc. Natl. Acad. Sci., USA*, 74, 5463 (1977)], and then analyzing the clones using an automatic nucleotide sequence analyzer such as A.L.F. DNA Sequencer (manufactured by Pharmacia).

Whether or not the obtained cDNAs encode the full length amino acid sequences of VH and VL of the antibody comprising a secretory signal sequence can be confirmed by deducing the full length amino acid sequences of VH and VL from the determined nucleotide sequence and comparing them with the full length amino acid sequences of VH and VL of known antibodies [*Sequences of Proteins of Immunological Interest*, US Dep. Health and Human Services (1991), hereinafter referred to as "*Sequences of Proteins of Immunological Interest*"].

(3) Analysis of Amino Acid Sequence of V Region of Non-Human Animal Antibody

Regarding the full length amino acid sequences of VH and VL of the antibody comprising a secretory signal sequence, the length of the secretory signal sequence and the N-terminal amino acid sequences can be deduced and subgroups to which they belong can also be found, by comparing them with the full length amino acid sequences of VH and VL of known antibodies (*Sequences of Proteins of Immunological Interest*). In addition, the amino acid sequences of each CDR of VH and VL can also be found by comparing them with the amino acid sequences of VH and VL of known antibodies (*Sequences of Proteins of Immunological Interest*).

(4) Construction of Human Chimeric Antibody Expression Vector

A human chimeric antibody expression vector can be constructed by cloning cDNAs encoding VH and VL of a non-human animal antibody into upstream of genes encoding CH and CL of a human antibody in the vector for expression of humanized antibody described in the item 3(1). For example, a human chimeric antibody expression vector can be constructed by linking each of cDNAs encoding VH and VL of a non-human animal antibody to a synthetic DNA comprising nucleotide sequences at the 3'-terminals of VH and VL of a non-human animal antibody and nucleotide sequences at the 5'-terminals of CH and CL of a human antibody and also having a recognition sequence of an appropriate restriction enzyme at both terminals, and by cloning them into upstream of genes encoding CH and CL of a human antibody contained in the vector for expression of humanized antibody constructed described in the item 3(1) in such a manner that they can be expressed in a suitable form.

(5) Construction of cDNA Encoding V Region of Human CDR-Grafted Antibody cDNAs encoding VH and VL of a human CDR-grafted antibody can be obtained as follows. First, amino acid sequences of the frameworks (hereinafter referred to as "FR") of VH and VL of a human antibody for grafting CDR of VH and VL of a non-human animal antibody is selected. As the amino acid sequences of FRs of VH and VL of a human antibody, any amino acid sequences can be used so long as they are derived from a human antibody. Examples include amino acid sequences of FRs of VH and VL of human antibodies registered at databases such as Protein Data Bank, amino acid sequences common in each subgroup of FRs of VH and VL of human antibodies (Sequences of Proteins of Immunological Interest) and the like. In order to produce a human CDR-grafted antibody having enough activities, it is preferred to select an amino acid sequence having homology as high as possible (at least 60% or more) with amino acid sequences of VH and VL of a non-human animal antibody of interest.

Next, the amino acid sequences of CDRs of VH and VL of the non-human animal antibody of interest are grafted to the selected amino acid sequences of FRs of VH and VL of a human antibody to design amino acid sequences of VH and VL of the human CDR-grafted antibody. The designed amino acid sequences are converted into DNA sequences by considering the frequency of codon usage found in nucleotide sequences of antibody genes (Sequences of Proteins of Immunological Interest), and the DNA sequences encoding the amino acid sequences of VH and VL of the human CDR-grafted antibody are designed. Based on the designed DNA sequences, several synthetic DNAs having a length of about 100 bases are synthesized, and PCR is carried out by using them. In this case, it is preferred in each of the H chain and the L chain that 6 synthetic DNAs are designed in view of the reaction efficiency of PCR and the lengths of DNAs which can be synthesized.

Also, they can be easily cloned into the vector for expression of humanized antibody described in the item 3(1) by introducing recognition sequences of an appropriate restriction enzyme into the 5'-terminals of the synthetic DNA on both terminals. After the PCR, the amplified product is cloned into a plasmid such as pBluescript SK(−) (manufactured by Stratagene) and the nucleotide sequences are determined by the method in the item 3(2) to thereby obtain a plasmid having DNA sequences encoding the amino acid sequences of VH and VL of the desired human CDR-grafted antibody.

(6) Construction of Human CDR-Grafted Antibody Expression Vector

A human CDR-grafted antibody expression vector can be constructed by cloning the cDNAs encoding VH and VL of the human CDR-grafted antibody constructed in the item 3(5) into upstream of the gene encoding CH and CL of a human antibody in the vector for expression of humanized antibody described in the item 3(1). For example, recognizing sequences of an appropriate restriction enzyme are introduced into the 5'-terminals of both terminals of a synthetic DNA fragment, among the synthetic DNA fragments which are used in the item 3(5) for constructing the VH and VL of the human CDR-grafted antibody, so that they are cloned into upstream of the genes encoding CH and CL of a human antibody in the vector for expression of humanized antibody described in the item 3(1) in such a manner that they can be expressed in a suitable form, to thereby construct the human CDR-grafted antibody expression vector.

(7) Stable Production of Humanized Antibody

A transformant capable of stably producing a human chimeric antibody and a human CDR-grafted antibody (both hereinafter referred to as "humanized antibody") can be obtained by introducing the humanized antibody expression vector described in the items 3(4) and (6) into an appropriate animal cell.

The method for introducing a humanized antibody expression vector into an animal cell includes electroporation [Japanese Published Unexamined Patent Application No. 257891/90, *Cytotechnology*, 3, 133 (1990)] and the like.

As the animal cell into which a humanized antibody expression vector is introduced, any cell can be used so long as it is an animal cell which can produce the humanized antibody.

Examples include mouse myeloma cells such as NS0 cell and SP2/0 cell, Chinese hamster ovary cells such as CHO/dhfr− cell and CHO/DG44 cell, rat myeloma such as YB2/0 cell and IR983F cell, BHK cell derived from a syrian hamster kidney, a human myeloma cell such as Namalwa cell, and the like, and a Chinese hamster ovary cell CHO/DG44 cell, a rat myeloma YB2/0 cell and the host cells of the present invention described in the item 5 are preferred.

After introduction of the humanized antibody expression vector, a transformant capable of stably producing the humanized antibody can be selected by using a medium for animal cell culture comprising an agent such as G418 sulfate (hereinafter referred to as "G418"; manufactured by SIGMA) and the like in accordance with the method described in Japanese Published Unexamined Patent Application No. 257891/90. The medium to culture animal cells includes RPMI 1640 medium (manufactured by Nissui Pharmaceutical), GIT medium (manufactured by Nihon Pharmaceutical), EX-CELL 302 medium (manufactured by JRH), IMDM medium (manufactured by GIBCO BRL), Hybridoma-SFM medium (manufactured by GIBCO BRL), media obtained by adding various additives such as fetal bovine serum (hereinafter referred to as "FBS") to these media, and the like. The humanized antibody can be produced and accumulated in the culture supernatant by culturing the obtained transformant in a medium. The amount of production and antigen binding activity of the humanized antibody in the culture supernatant can be measured by a method such as enzyme-linked immunosorbent assay (hereinafter referred to as "ELISA"; Antibodies, Monoclonal Antibodies) or the like. Also, the amount of the humanized antibody produced by the transformant can be increased by using a DHFR gene amplification system in accordance with the method described in Japanese Published Unexamined Patent Application No. 257891/90.

The humanized antibody can be purified from a medium culturing the transformant by using a protein A column (*Antibodies*, Chapter 8, *Monoclonal Antibodies*). In addition, purification methods generally used for the purification of proteins can also be used. For example, the purification can be carried out through the combination of gel filtration, ion exchange chromatography and ultrafiltration. The molecular weight of the H chain, L chain or antibody molecule as a whole of the purified humanized antibody can be measured, e.g., by polyacrylamide gel electrophoresis [hereinafter referred to as "SDS-PAGE"; *Nature*, 27, 680 (1970)], Western blotting (*Antibodies*, Chapter 12, *Monoclonal Antibodies*) or the like.

B. Preparation of Fc Fusion Protein (1) Construction of Vector for Expression of Fc Fusion Protein An Fc fusion protein expression vector is an expression vector for animal cell into which genes encoding the Fc region of a human antibody and a protein to be fused are inserted, which can be constructed by cloning each of genes encoding the Fc region of a human antibody and the protein to be fused into an expression vector for animal cell.

The Fc region of a human antibody includes those containing a part of a hinge region and/or CH1 in addition to regions containing CH2 and CH3 regions. Also, it can be any Fc region so long as at least one amino acid of CH2 or CH3 may be deleted, substituted, added or inserted, and substantially has the binding activity to the Fcγ receptor.

As the genes encoding the Fc region of a human antibody and the protein to be fused, a chromosomal DNA comprising an exon and an intron can be used, and a cDNA can also be used. The method for linking the genes and the Fc region includes PCR using each of the gene sequences as the template (*Molecular Cloning*, Second Edition, *Current Protocols in Molecular Biology*, Supplement 1-34).

As the expression vector for animal cell, any vector can be used, so long as a gene encoding the C region of a human antibody can be inserted thereinto and expressed therein. Examples include pAGE107 [*Cytotechnology*, 3, 133 (1990)], pAGE103 [*J. Biochem*, 101, 1307 (1987)], pHSG274 [*Gene*, 27, 223 (1984)], pKCR [*Proc. Natl. Acad. Sci. USA*, 78, 1527 (1981), pSG1 β d2-4 [*Cytotechnology*, 4, 173 (1990)] and the like. The promoter and enhancer in the expression vector for animal cell include SV40 early promoter and enhancer [*J. Biochem.*, 101, 1307 (1987)], Moloney mouse leukemia virus LTR [*Biochem. Biophys. Res. Commun.*, 149, 960 (1987)], immunoglobulin H chain promoter [*Cell*, 41, 479 (1985)] and enhancer [*Cell*, 33, 717 (1983)], and the like.

(2) Preparation of DNA Encoding Fc Region of Human Antibody and Protein to be Fused A DNA encoding the Fc region of a human antibody and the protein to be fused can be obtained in the following manner.

A cDNA is synthesized from mRNA extracted from a cell or tissue which expresses the protein of interest to be fused with Fc. The synthesized cDNA is cloned into a vector such as a phage or a plasmid to obtain a cDNA library. A recombinant phage or recombinant plasmid comprising cDNA encoding the protein of interest is isolated from the library by using the gene sequence part of the protein of interest as the probe. A full nucleotide sequence of the antibody of interest on the recombinant phage or recombinant plasmid is determined, and a full length amino acid sequence is deduced from the nucleotide sequence.

As the non-human animal, any animal such as mouse, rat, hamster or rabbit can be used, so long as a cell or tissue can be removed therefrom.

The method for preparing a total RNA from a cell or tissue includes the guanidine thiocyanate-cesium trifluoroacetate method [*Methods in Enzymology*, 154, 3 (1987)] and the like, and the method for preparing mRNA from total RNA includes an oligo (dT)-immobilized cellulose column method (*Molecular Cloning*, Second Edition) and the like. In addition, a kit for preparing mRNA from a cell or tissue includes Fast Track mRNA Isolation Kit (manufactured by Invitrogen), Quick Prep mRNA Purification Kit (manufactured by Pharmacia) and the like.

The method for synthesizing a cDNA and preparing a cDNA library includes the usual methods (*Molecular Cloning*, Second Edition; *Current Protocols in Molecular Biology*, Supplement 1-34); methods using a commercially available kit such as SuperScript™, Plasmid System for cDNA Synthesis and Plasmid Cloning (manufactured by GIBCO BRL) or ZAP-cDNA Synthesis Kit (manufactured by Stratagene), and the like.

In preparing the cDNA library, the vector into which a cDNA synthesized by using mRNA extracted from a cell or tissue as the template is inserted may be any vector so long as the cDNA can be inserted. Examples include ZAP Express [*Strategies*, 5, 58 (1992)], pBluescript II SK(+) [*Nucleic Acids Research*, 17, 9494 (1989)], λzapII (manufactured by Stratagene), λgt10 and λgt11 [*DNA Cloning, A Practical Approach, I*, 49 (1985)], Lambda BlueMid (manufactured by Clontech), λExCell, pT7T3 18U (manufactured by Pharmacia), pcD2 [*Mol. Cell. Biol*, 3, 280 (1983)], pUC18 [*Gene*, 33, 103 (1985)] and the like.

As *Escherichia coli* into which the cDNA library constructed from a phage or plasmid vector is introduced, any *Escherichia coli* can be used, so long as the cDNA library can be introduced, expressed and maintained. Examples include XL1-Blue MRF' [*Strategies*, 5, 81 (1992)], C600 [*Genetics*, 39, 440 (1954)], Y1088 and Y1090 [*Science*, 222, 778 (1983)], NM522 [*J. Mol. Biol.*, 166, 1 (1983)], K802 [*J. Mol. Biol.*, 16, 118 (1966)], JM105 [*Gene*, 38, 275 (1985)] and the like.

As the method for selecting a cDNA clone encoding the protein of interest from the cDNA library, a colony hybridization or a plaque hybridization using an isotope- or fluorescence-labeled probe can be used (*Molecular Cloning*, Second Edition). The cDNA encoding the protein of interest can also be prepared by preparing primers and using a cDNA synthesized from mRNA or a cDNA library as the template according to PCR.

The method for fusing the protein of interest with the Fc region of a human antibody includes PCR. For example, synthesized oligo DNAs (primers) are designed at the 5'-terminal and 3'-terminal of the gene sequence encoding the protein of interest, and PCR is carried out to prepare a PCR product. In the same manner, primers are designed for the gene sequence encoding the Fc region of a human antibody to be fused. At this time, the primers are designed in such a manner that the same restriction enzyme site or the same gene sequence is present between the 3'-terminal of the PCR product of the protein to be fused and the 5'-terminal of the PCR product of the Fc region. When it is necessary to modify the amino acids around the linked site, mutation is introduced by using the primer into which the mutation is introduced. PCR is further carried out by using the two kinds of the obtained PCR fragments to link the genes. Also, they can be linked by carrying out ligation after treatment with the same restriction enzyme.

The nucleotide sequence of the DNA can be determined by digesting the gene sequence linked by the above method with appropriate restriction enzymes, cloning the fragments into a plasmid such as pBluescript SK(−) (manufactured by Stratagene), carrying out analysis by using a generally used nucleotide sequence analyzing method such as the dideoxy method of Sanger et al. [*Proc. Natl. Acad. Sci. USA*, 74, 5463 (1977)] or an automatic nucleotide sequence analyzer such as A.L.F. DNA Sequencer (manufactured by Pharmacia).

Whether or not the obtained cDNA encodes the full length amino acid sequences of the Fc fusion protein containing a secretory signal sequence can be confirmed by deducing the full length amino acid sequence of the Fc fusion protein from the determined nucleotide sequence and comparing it with the amino acid sequence of interest.

(3) Stable Production of Fc Fusion Protein

A transformant capable of stably producing an Fc fusion protein can be obtained by introducing the Fc fusion protein expression vector described in the item (1) into an appropriate animal cell.

The method for introducing the Fc fusion protein expression vector into an animal cell include electroporation [Japanese Published Unexamined Patent Application No. 257891/90, *Cytotechnology*, 3, 133 (1990)] and the like.

As the animal cell into which the Fc fusion protein expression vector is introduced, any cell can be used, so long as it is an animal cell which can produce the Fc fusion protein.

Examples include mouse myeloma cells such as NS0 cell and SP2/0 cell, Chinese hamster ovary cells such as CHO/dhfr⁻ cell and CHO/DG44 cell, rat myeloma such as YB2/0 cell and IR983F cell, BHK cell derived from a syrian hamster kidney, a human myeloma cell such as Namalwa cell, and the like, and preferred are a Chinese hamster ovary cell CHO/DG44 cell, a rat myeloma YB2/0 cell and the host cells used in the method of the present invention described in the item 1.

After introduction of the Fc fusion protein expression vector, a transformant capable of stably producing the Fc fusion protein expression vector can be selected by using a medium for animal cell culture comprising an agent such as G418 and the like in accordance with the method described in Japanese Published Unexamined Patent Application No. 257891/90. The medium to culture animal cells includes RPNU 1640 medium (manufactured by Nissui Pharmaceutical), GIT medium (manufactured by Nihon Pharmaceutical), EX-CELL 302 medium (manufactured by JRH), IMDM medium (manufactured by GIBCO BRL), Hybridoma-SFM medium (manufactured by GIBCO BRL), media obtained by adding various additives such as fetal bovine serum to these media, and the like. The Fc fusion protein can be produced and accumulated in the culture supernatant by culturing the obtained transformant in a medium. The amount of production and antigen binding activity of the Fc fusion protein in the culture supernatant can be measured by a method such as ELISA. Also, the amount of the Fc fusion protein produced by the transformant can be increased by using a dhfr gene amplification system in accordance with the method described in Japanese Published Unexamined Patent Application No. 257891/90.

The Fc fusion protein can be purified from a culture supernatant culturing the transformant by using a protein A column or a protein G column (*Antibodies*, Chapter 8; *Monoclonal Antibodies*). In addition, purification methods generally used for purifying proteins can also be used. For example, the purification can be carried out through the combination of a gel filtration, an ion exchange chromatography and an ultrafiltration. The molecular weight as a whole of the purified Fc fusion protein molecule can be measured by SDS-PAGE [*Nature*, 227, 680 (1970)], Western blotting (*Antibodies*, Chapter 12; *Monoclonal Antibodies*) or the like.

Thus, methods for producing an antibody composition using an animal cell as the host cell have been described, but, as described above, it can also be produced by yeast, an insect cell, a plant cell, an animal individual or a plant individual by the same methods on the animal cell.

When the host cell is capable of preparing the antibody molecule, the antibody composition of the present invention can be prepared by culturing the cell capable of expressing an antibody molecule according to the method described in the above item 1, culturing the cell, and recovering the antibody composition of interest.

4. Activity Evaluation of Antibody Composition

As the method for measuring the amount of the purified antibody composition, the binding activity to an antibody and the effector function of the purified antibody composition, the known method described in *Monoclonal Antibodies, Antibody Engineering* or the like can be used.

For example, in the case where the antibody composition is a humanized antibody, the binding activity with an antigen and the binding activity with an antigen-positive cultured clone can be measured by methods such as ELISA, an immunofluorescent method [*Cancer Immunol. Immunother.*, 36, 373 (1993)] and the like. The cytotoxic activity against an antigen-positive cultured clone can be evaluated by measuring CDC activity, ADCC activity [*Cancer Immunol. Immunother.*, 36, 373 (1993)] and the like.

The amount of antigen expressed on a cell relating to diseases can be determined by the Scatchard analysis [*Immunological Methods*, Vol. 2, published by New York Academic Press (1981)] or by the quantitative flow cytometry [*Cytometry (Communications in Clinical Cytometry)*, 2, 22 (1996)].

Therapeutic effects of different agents can be compared by an in vivo test using a disease model which uses an experimental animal such as mouse, rat, hamster, guinea pig, rabbit, dog, pig or monkey. In addition, the effects can also be compared by an in vitro cytotoxic activity measurement using a cell relating to diseases or an established cell thereof as the target.

The in vivo test can be carried out by transplanting a target cell such as a cell relating to diseases or an established cell thereof, into the body of an experimental animal, administering each agent, for example, intraperitoneally, intravenously or subcutaneously, and observing the morbid state of the experimental animal. For example, therapeutic effect of an agent can be examined by measuring growth of a tumor, survived days of an experimental animal, a blood component concentration of the agent, weight of an organ and the like.

The in vitro cytotoxic activity can be obtained by measuring ADCC activity, CDC activity and the like.

5. Analysis of Sugar Chains Binding to Antibody Molecule Expressed in Various Cells The sugar chain structure binding to an antibody molecule expressed in various cells can be analyzed in accordance with the general analysis of the sugar chain structure of a glycoprotein. For example, the sugar chain which is bound to IgG molecule comprises a neutral sugar such as galactose, mannose, fucose, an amino sugar such as N-acetylglucosamine and an acidic sugar such as sialic acid, and can be analyzed by a method such as a sugar chain structure analysis by using sugar composition analysis, two dimensional sugar chain mapping or the like.

(1) Analysis of Neutral Sugar and Amino Sugar Compositions

The sugar chain composition binding to an antibody molecule can be analyzed by carrying out acid hydrolysis of sugar chains with trifluoroacetic acid or the like to release a neutral sugar or an amino sugar and measuring the composition ratio.

Examples include a method by using a sugar composition analyzer (BioLC) manufactured by Dionex. The BioLC is an apparatus which analyzes a sugar composition by HPAEC-PAD (high performance anion-exchange chromatography-pulsed amperometric detection) [*J. Liq. Chromatogr.*, 6, 1577 (1983)].

The composition ratio can also be analyzed by a fluorescence labeling method by using 2-aminopyridine. Specifically, the composition ratio can be calculated in accordance with a known method [*Agric. Biol. Chem.*, 55(1) 283-284 (1991)] by labeling an acid-hydrolyzed sample with a fluorescence by 2-aminopyridylation and then analyzing the composition by HPLC.

(2) Analysis of Sugar Chain Structure

The sugar chain structure binding to an antibody molecule can be analyzed by the two dimensional sugar chain mapping method [*Anal. Biochem.*, 171, 73 (1988), *Biochemical Experimentation Methods* 23—*Methods for Studying Glycoprotein Sugar Chains* (Japan Scientific Societies Press) edited by Reiko Takahashi (1989)]. The two dimensional sugar chain mapping method is a method for deducing a sugar chain structure by, e.g., plotting the retention time or elution position of a sugar chain by reverse phase chromatography as the X axis and the retention time or elution position of the sugar chain by normal phase chromatography as the Y axis, respectively, and comparing them with those of known sugar chains.

Specifically, sugar chains are released from an antibody by subjecting the antibody to hydrazinolysis, and the released sugar chain is subjected to fluorescence labeling with 2-aminopyridine (hereinafter referred to as "PA") [*J. Biochem.*, 95, 197 (1984)], and then the sugar chains are separated from an excess PA-treating reagent by gel filtration, and subjected to reverse phase chromatography. Thereafter, each peak of the separated sugar chains are subjected to normal phase chromatography. The sugar chain structure can be deduced by plotting the results on a two dimensional sugar chain map and comparing them with the spots of a sugar chain standard (manufactured by Takara Shuzo) or a literature [*Anal. Biochem.*, 171, 73 (1988)].

The structure deduced by the two dimensional sugar chain mapping method can be confirmed by further carrying out mass spectrometry such as MALDI-TOF-MS of each sugar chain.

6. Immunological Determination Method for Discriminating the Sugar Chain Structure Binding to Antibody Molecule An antibody composition comprises an antibody molecule in which sugar chains bound to the Fc region of the antibody are different in structure. The antibody composition included as an active ingredient in the therapeutic agent of the present invention, which has complex N-glycoside-linked sugar chains, bound to the Fc region in the antibody, and in which the ratio of sugar chains in which 1-position of fucose is not bound to 6-position of N-acetylglucosamine in the reducing end through α bond to the total complex N-glycoside-linked sugar chains is 20% or more, has high ADCC activity. The antibody composition can be identified by using the method for analyzing the sugar chain structure binding to an antibody molecule described in the item 5. Also, it can also be identified by an immunological determination method using a lectin.

The sugar chain structure binding to an antibody molecule can be identified by the immunological determination method using a lectin in accordance with the known immunological determination method such as Western staining, IRA (radioimmunoassay), VIA (viroimmunoassay), EIA (enzymoimmunoassay), FIA (fluoroimmunoassay) or MIA (metalloimmunoassay) described in *Monoclonal Antibodies: Principles and Applications*, Wiley-Liss, Inc. (1995); *Immunoassay (Koso Meneki Sokzteiho)*, 3rd Ed., Igakushoin (1987);

*Enzyme Antibody Method* (*Koso Kotaiho*), Revised Edition, Gakusai Kikaku (1985), and the like.

A lectin which recognizes the sugar chain structure binding to an antibody molecule comprised in an antibody composition is labeled, and the labeled lectin is allowed to react with a sample antibody composition. Then, the amount of the complex of the labeled lectin with the antibody molecule is measured.

The lectin used for identifying the sugar chain structure binding to an antibody molecule includes WGA (wheat-germ agglutinin derived from *T. vulgaris*), ConA (cocanavalin A derived from *C. ensiformis*), RIC (toxin derived from *R. communis*), L-PHA (leucoagglutinin derived from *P. vulgaris*), LCA (lentil agglutinin derived from *L. culinaris*), PSA (pea lectin derived from *P. sativum*), AAL (*Aleuria aurantia* lectin), ACL (*Amaranthus caudatus* lectin), BPL (*Bauhinia purpurea* lectin), DSL (*Datura stramonium* lectin), DBA (*Dolichos biflorus* agglutinin), EBL (elderberry balk lectin), ECL (*Erythrina cristagalli* lectin), EEL (*Euonymus eoropaeus* lectin), GNL (*Galanthus nivalis* lectin), GSL (*Griffonia simplicifola* lectin), HPA (*Helix pomatia* agglutinin), HHL (*Hippeastrum* hybrid lectin), Jacalin, LTL (*Lotus tetragonolobus* lectin), LEL (*Lycopersicon esculentum* lectin), MAJL (*Maackia amurensis* lectin), MPL (*Maclura pomifera* lectin), NPL (*Narcissus pseudonarcissus* lectin), PNA (peanut agglutinin), E-PHA (*Phaseolus vulgaris* erythroagglutinin), PTL (*Psophocarpus tetragonolobus* lectin), RCA (*Ricinus communis* agglutinin), 5 ml (*Solanum tuberosum* lectin), SJA (*Sophora japonica* agglutinin), SBA (soybean agglutinin), UEA (*Ulex europaeus* agglutinin), VVL (*Vicia villosa* lectin) and WFA (*Wisteria floribunda* agglutinin).

In order to identify the antibody composition of the present invention, the sugar chain structure can be analyzed in detail by using a lectin which specifically recognizes a sugar chain structure wherein fucose is bound to the N-acetylglucosamine in the reducing end in the complex N-glycoside-linked sugar chain. Examples include *Lens culinaris* lectin LCA (lentil agglutinin derived from *Lens culinaris*), pea lectin PSA (pea lectin derived from *Pisum sativum*), broad bean lectin VFA (agglutinin derived from *Vicia faba*) and *Aleuria aurantia* lectin AAL (lectin derived from *Aleuria aurantia*).

7. Method for Screening Patient to Whom Antibody Medicaments Produced in Lectin-Resistant Cells is Effective A method for screening a patient to whom the medicament of the present invention is effective is a method which comprises collecting the target cell related to the disease from the patient's body, contacting the cell with the medicament of the present invention or a conventional antibody, respectively, measuring activities of the medicament of the present invention and of the conventional antibody medicament, and comparing the activity shown by the conventional antibody medicament with that of the medicament of the present invention, to screen a patient to whom the medicament of the invention is effective. Specifically, the method includes a method for screening a patient to whom the medicament of the present invention is effective, which comprises: (i) contacting a medicament comprising as an active ingredient an antibody composition produced by a cell unresistant to a lectin which recognizes a sugar chain structure in which fucose is bound to N-acetylglucosamine in the reducing end through α-bond in a complex N-glycoside-linked sugar chain or the medicament of the present invention, with a target cell for the medicaments obtained from a patient; (ii) measuring the activity of each of the medicaments reacted with the target cell; (iii) comparing the activity of the medicament comprising as an active ingredient an antibody composition produced by a cell unresistant to a lectin which recognizes a sugar chain in which 1-position of fucose is bound to 6-position of N-acetylglucosamine in the reducing end through α-bond in a complex N-glycoside-linked sugar chain with the activity of the medicament of the present invention; and (iv) selecting a patient in which the activity of the medicament comprising as an active ingredient an antibody composition produced by a cell unresistant to a lectin which recognizes a sugar chain in which 1-position of fucose is bound to 6-position of N-acetylglucosamine in the reducing end through α-bond in a complex N-glycoside-linked sugar chain is lower. As the method for collecting the target cells from patients, they can be obtained by surgical biopsy or from body fluid.

The method for measuring the activity of the medicament of the present invention or the conventional antibody medicament includes a method for measuring ADCC activity, Fcγ-receptor IIIa binding activity, CDC activity or growth inhibiting activity, and the like.

The method for measuring ADCC activity comprises contacting the intact target cells or target cells labeled with a radioisotope, fluorescence or pigment with an antibody and an effector cell simultaneously, and measuring the physiological activity of enzyme released by the injured target cell or the activity of labeled substance.

The method for measuring an Fcγ-receptor IIIa binding activity comprises measuring the amount of the antibody reacting with the target cells which are bound to a recombinant Fcγ-receptor IIIa protein or Fcγ-receptor IIIa expressed by virus or bacteria or on the surface of cells. The measurement can be achieved by immunoassay such as immunological tissue staining, enzyme immunoassay and radioimmunoassay, immunofluorescence technique using flow cytometer, immunoblotting, aggregation reaction, complement fixing reaction, hemolytic reaction, precipitation reaction, gold colloid method, chromatography, and the like.

The detection can be carried out more easily by adding a label such as enzyme, fluorescent substance, pigment, tag peptide or radioisotope to Fcγ-receptor IIIa.

The method for measuring CDC activity comprises contacting the target cells labeled or unlabeled with a radioisotope, fluorescent substance or pigment with an antibody and a serum containing a complement component simultaneously, and determining the physiological activity of the enzyme released by the injured target cell or the activity of labeled substance.

The method for measuring a growth inhibiting activity includes measurement of the physiological activity of intracellular enzyme, staining with propidium iodide, assay utilizing the change of cell membrane permeability, TUNEL method, detection of annexin V, detection of fragment DNA, detection of the change of membrane potential of mitochondria, detection of the intracellular ATP and ADP levels, and the like.

8. Method for Treating Patient Using Antibody Medicament Produced in Lectin-Resistant Cell The method for treating a patient using the medicament of the present invention includes a method in which a patient to whom the medicament of the present invention is effective is selected according to the method shown in the item 7 and then the following therapeutic agent is administered to the selected patient.

The medicament can be administered as a therapeutic agent alone, but generally, it is preferred to provide it as a pharmaceutical formulation produced by an appropriate method well known in the technical field of manufacturing pharmacy, by mixing it with at least one pharmaceutically acceptable carrier.

It is preferred to select a route of administration which is most effective in treatment. Examples include oral administration and parenteral administration, such as buccal, tracheal, rectal, subcutaneous, intramuscular and intravenous administrations. In the case of an antibody preparation, intravenous administration is preferred.

The dosage form includes sprays, capsules, tablets, granules, syrups, emulsions, suppositories, injections, ointments, tapes and the like.

The pharmaceutical preparation suitable for oral administration include emulsions, syrups, capsules, tablets, powders, granules and the like.

Liquid preparations such as emulsions and syrups can be produced using, as additives, water sugars such as sucrose, sorbitol and fructose; glycols such as polyethylene glycol and propylene glycol; oils such as sesame oil, olive oil and soybean oil; antiseptics such as p-hydroxybenzoic acid esters; flavors such as strawberry flavor and peppermint; and the like.

Capsules, tablets, powders, granules and the like can be produced by using, as additives, excipients such as lactose, glucose, sucrose and mannitol; disintegrating agents such as starch and sodium alginate; lubricants such as magnesium stearate and talc; binders such as polyvinyl alcohol, hydroxypropylcellulose and gelatin, surfactants such as fatty acid ester; plasticizers such as glycerine; and the like.

The pharmaceutical preparation suitable for parenteral administration includes injections, suppositories, sprays and the like.

Injections may be prepared by using a carrier such as a salt solution, a glucose solution or a mixture of both thereof. Also, powdered injections can be prepared by freeze-drying the antibody composition in the usual way and adding sodium chloride thereto.

Suppositories may be prepared by using a carrier such as cacao butter, hydrogenated fat or carboxylic acid.

Also, sprays may be prepared by using the antibody composition as such or using a carrier which does not stimulate the buccal or airway mucous membrane of the patient and can facilitate absorption of the antibody composition by dispersing it as fine particles.

The carrier includes lactose, glycerine and the like. Depending on the properties of the antibody composition and the carrier, it is possible to produce pharmaceutical preparations such as aerosols and dry powders. In addition, the components exemplified as additives for oral preparations can also be added to the parenteral preparations.

Although the clinical dose or the frequency of administration varies depending on the objective therapeutic effect, administration method, treating period, age, body weight and the like, it is usually 10 μg/kg to 20 mg/kg per day and per adult.

The present invention will be described below in detail based on Examples; however, Examples are only simple illustrations, and the scope of the present invention is not limited thereto.

EXAMPLE 1

Targeting Cytotoxic Activity Depending on Antigen Expression Amount Based on ADCC Activity of Anti-CCR4 Chimeric Antibody Composition 1. Preparation of Transfectant Cells which Express CCR4 at Various Amounts (1) Selection of Clones which Expresses CCR4 at Various Amounts A stable CCR4 gene expression vector for animal cell CAG-CCR4/pcDNA3 (WO01/64754) was introduced into a mouse thymoma cell line EL-4 cell (ATCC TIB-39) by electroporation. First, the EL-4 cell was suspended in PBS(−) (manufactured by GIBCO BRL) to give a density of $1\times10^7$ cells/500 μl, allowed to stand for 10 minutes on ice by adding 10 μg of CAG-CCR4/pcDNA3 and then put into a special purpose cuvette (manufactured by Bio-Rad) to carry out gene transfer at 260 V and 500 μFD. The cells were further allowed to stand for 10 minutes on ice, suspended in 200 ml of RPMI1640 medium (manufactured by Life Technlogie) containing 10% fetal bovine serum (manufactured by Life Technlogie) (hereinafter referred to as "RPMI1640-FBS(10)") and then dispensed at 100 μl/well into a 96 well cell culture plate. After culturing for 24 hours, 100 μl/well of the supernatant was discarded, and 10% FCS-RPMI medium containing 1 mg/ml G418 was dispensed at 100 μl/well to adjust the final concentration to 0.5 mg/ml. Two weeks thereafter, several tens of single clones were selected and subjected to expansion culturing.

(2) Selection of Clones which Express CCR4 at Various Amounts

Figure 2:
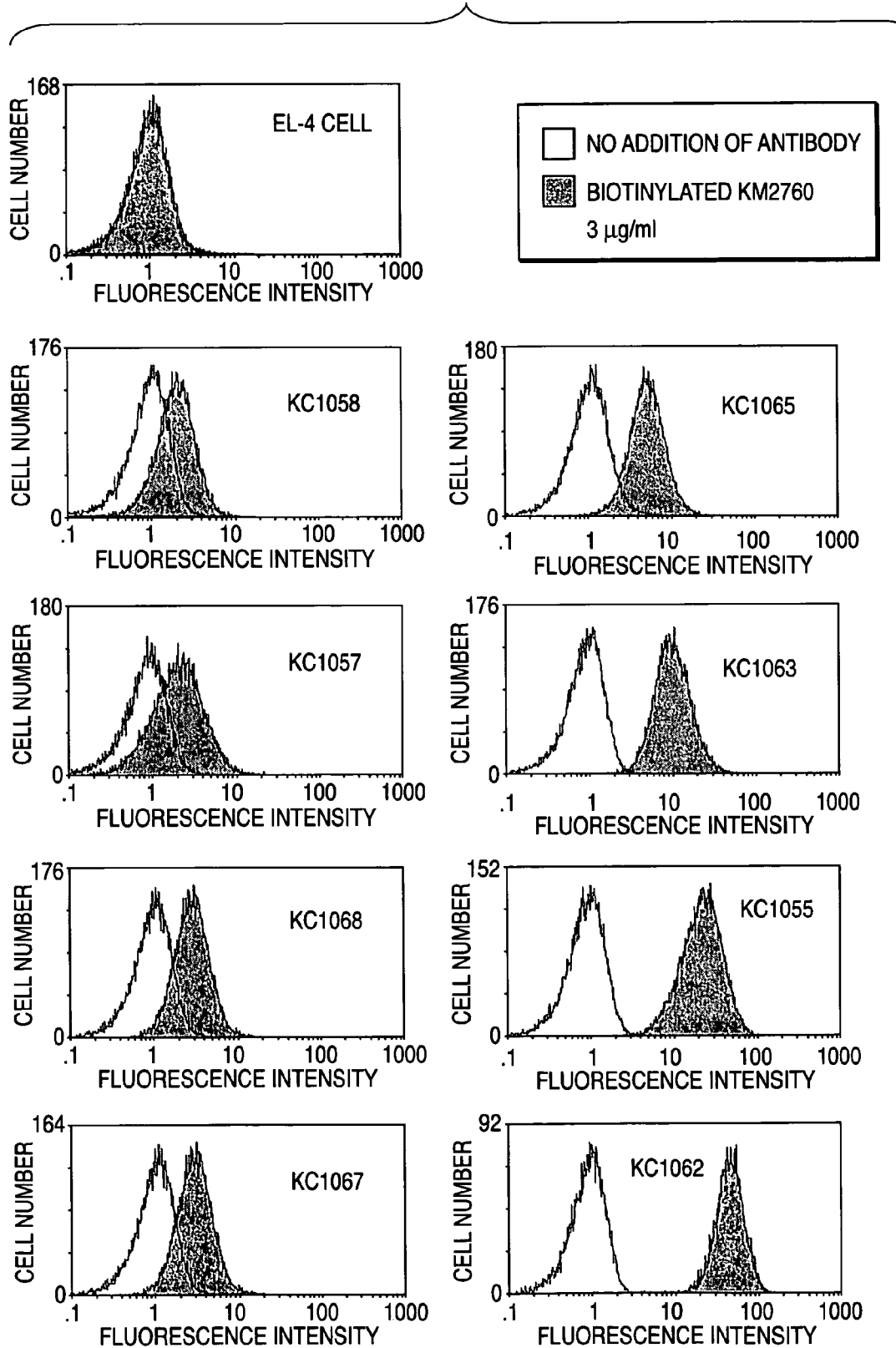
FIG. 2 shows histograms of CCR4 expression in transfectant cells which express CCR4 at various amounts and in the parent cell line EL-4 cell which was analyzed by using a flow cytometer. The ordinate and the abscissa show the fluorescence intensity and the cell number, respectively. The open square and the gray square show the histogram when no antibody was added and the histrogram when biotinylated KM27601 was added, respectively.

Using anti-CCR4 chimeric antibody KM2760-1 as prepared in Reference Example 1, clones which express CCR4 at various amounts were selected based on the presence or absence of staining ability by FACS. Each of the gene-transferred cells of the several tens of lines selected in the item (1) was dispensed at $1\times10^6$ cells into a 96 well U-shape plate. KM2760-1 labeled with biotin by a conventional method [*Enzyme Antibody Method* (*Koso Kotai Ho*), published by Gakusai Kikaku (1985)] was diluted with FACS buffer (1% BSA-PBS, 0.02% EDTA, 0.05% $NaN_3$, pH 7.4) to 3 μg/ml, and a normal mouse serum (manufactured by CEDERLANCE) to 5% in order to prevent non-specific staining, and each solution was added thereto at 100 μl/well and allowed to react for 60 minutes on ice. As a negative control, a well to which the biotinylated KM2760-1 was not added was also arranged. After washing twice with 200 μl/well of the buffer, Streptavidin-RED670 (manufactured by GIBCO BRL) diluted 200-fold with the FACS buffer was added at 100 μl/well. After the reaction on ice under shade for 60 minutes, the cells were washed three times at 200 μl/well and finally suspended in 500 μl of PBS(−), and then the fluorescence intensity was measured using a flow cytometer EPICS ELITE (manufactured by COULTER). A total of 8 lines showing various fluorescence intensities were selected and named KC1058, KC1057, KC1068, KC1068, KC1065, KC1063, KC1055 and KC1062 in order from the lowest expression amount. A histogram of fluorescence intensities of each clone and EL-4 cell of the parent clone is shown in FIG. 2.

(3) Determination of the Number of CCR4 Molecules Expressed in the Clones which Expresses CCR4 at Various Amounts The number of CCR4 molecules expressed in each of the clones obtained in the item (1) was determined with a flow cytometer. Each of the clones was suspended at $1\times10^6$ cells in 100 μl of the FACS buffer containing 60 μg/ml of the anti-CCR4 mouse monoclonal antibody KM2160 described in WO01/64754, or 3.75 mg/ml human IgG (manufactured by Welfide) for preventing non-specific staining, dispensed into a 96 well U-shape plate and then allowed to react for 60 minutes on ice. As a negative control, an anti-human VEGF receptor Flt-1 monoclonal antibody KM1732 (WO98/22616; a monoclonal antibody produced by a hybridoma FERM BP-5698) was added instead of KM2160. After washing twice with the buffer at 200 μl/well, an FITC-labeled anti-mouse IgG (manufactured by DAKO) diluted 4-fold with the FACS buffer was added at 100 μl/well. After the reaction on ice under shade for 60 minutes, the cells were washed three times at 200 μl/well and finally suspended in 500 μl of PBS (−), and then the fluorescence intensity was measured with a flow cytometer EPICS ELITE (manufactured by COULTER). Also, using standard beads coated with known numbers of mouse IgG (DAKO QIFUKIT, manufactured by DAKO), they were allowed to react with the FITC-labeled anti-mouse IgG under the same conditions as described in the above and washed as a standard sample for the determination of the number of CCR4 molecules, and then the fluorescence intensity was measured with the flow cytometer. In accordance with the instructions attached to the standard beads, a correlation formula of the fluorescence intensity and the number of mouse IgG molecules bound to the beads was prepared, and the number of CCR4 molecules of each clone was calculated by substituting the fluorescence intensity of each clone reacted with KM2160. In addition, the number of CCR4 molecules when reacted with KM1732 was also calculated as background and deducted from the number of CCR4 molecules when reacted with KM2160, thereby finally obtaining the number of CCR4 molecules expressed in each clone. The results are shown in Table 1.

TABLE 1

| Cell name | The number of CCR4 |
|---|---|
| EL-4 cell | $6.57 \times 10^2$ |
| KC1058 | $1.28 \times 10^3$ |
| KC1057 | $1.63 \times 10^3$ |
| KC1068 | $2.61 \times 10^3$ |
| KC1067 | $4.65 \times 10^3$ |
| KC1065 | $5.80 \times 10^3$ |
| KC1063 | $1.53 \times 10^4$ |
| KC1055 | $1.71 \times 10^4$ |
| KC1062 | $5.42 \times 10^4$ |

Unit: numbers/cell

2. Measurement of ADCC Activity Using Clones which Express CCR4 at Various Amounts as Target Cells The relationship between the ADCC activity of KM2760-1 and KM3060 and the antigen number was examined by using the clones which express CCR4 at various amounts obtained in the item 5 of Example 1 as target cells.

(1) Preparation of Target Cell Solution

Each of the clones which express CCR4 at various amounts was cultured in the RPMI1640-FBS(10) medium supplemented with 500 μg/ml G418 sulfate (manufactured by Nacalai Tesque) to prepare $1 \times 10^6$ cells, and the cells were radioisotope-labeled by reacting them with 3.7 MBq equivalents of a radioactive substance $Na_2^{51}CrO_4$ at 37° C. for 60 minutes. After the reaction, the cells were washed three times through their suspension in the RPMI1640-FBS(10) medium and centrifugation, re-suspended in the medium and then incubated at 4° C. for 30 minutes on ice to allow spontaneous releasing of the radioactive substance. After centrifugation, the precipitate was adjusted to $2 \times 10^5$ cells/ml by adding 5 ml of the RPMI1640-FBS(10) medium and used as the target cell solution.

(2) Preparation of Effector Cell Solution

From a healthy doner, 50 ml of venous blood was collected, and gently mixed with 0.5 ml of heparin sodium (manufactured by Takeda Pharmaceutical). The mixture was centrifuged to isolate a mononuclear cell layer by using Lymphoprep (manufactured by Nycomed Pharma AS) in accordance with the manufacture's instructions. After washing with the RPMI1640-FBS(10) medium by centrifugation three times, the resulting precipitate was re-suspended to give a density of $2 \times 10^6$ cells/ml in the medium and used as the effector cell solution.

(3) Measurement of ADCC Activity

Into each well of a 96 well round-bottom plate (manufactured by Falcon), 50 μl of the target cell solution prepared in the above (1) ($1 \times 10^4$ cells/well) was dispensed. Next, 100 μl of the effector cell solution prepared in the above (2) was added thereto ($2 \times 10^5$ cells/well, the ratio of effector cells to target cells becomes 25:1). Subsequently, each of the anti-CCR4 chimeric antibodies, KM2760-1 and KM3060 obtained in the item 3 of Example 1, was added to give a final concentration 3 μg/ml, followed by reaction at 37° C. for 4 hours. After the reaction, the plate was centrifuged, and the amount of $^{51}Cr$ in the supernatant was measured with a γ-counter. The amount of spontaneously released $^{51}Cr$ was calculated by the same operation using only the medium instead of the effector cell solution and the antibody solution, and measuring the amount of $^{51}Cr$ in the supernatant. The amount of total released $^{51}Cr$ was calculated by the same operation using only the medium instead of the antibody solution and adding 1 N hydrochloric acid instead of the effector cell solution, and measuring the amount of $^{51}Cr$ in the supernatant. The ADCC activity was calculated by the following equation (1)

$$ADCC \text{ activity}(\%) = \frac{^{51}Cr \text{ in sample supernatant} - \text{spontaneously released } ^{51}Cr}{\text{total released } ^{51}Cr - \text{spontaneously released } ^{51}Cr} \times 100 \quad (1)$$

The results are shown in FIG. 3. Both of KM2760-1 and KM3060 showed the ADCC activity depending on the antigen numbers, but the ADCC activity of KM2760-1 sharply exceeded that of KM3060. As a result of using a data analysis software KaleidaGraph™ (manufactured by SYNERGY SOFTWARE), the plot of KM2760-1 was approximated by the following equation (2):

$$y = (-60.83/(1+(x/9996)^{2.22})) + 63.23 \quad (2)$$

In equation (2), symbol x represents the number of CCR4, and y represents the cytotoxic activity.

The KM3060 showed a cytotoxic activity of 7.4% for KC1062 having the largest CCR4 expressing numbers (the number of CCR4: 54,200 molecules/cell). When the number of CCR4 necessary for KM2760-1 to show equivalent cytotoxic activity is calculated by substituting this value for formula (2), it is 3,360 molecules/cell. That is, it was found that KM2760-1 shows equivalent ADCC activity at about 1/16 of the number of CCR4 of KM3060. Further, it was found that KM3060 does not match KM2760-1 for cytotoxic activity even on such conditions that the number of CCR4 per cell against KM3060 is higher than that of KM2760-1, and that cytotoxic activity of KM3060 is saturated at lower levels.

3. Sugar Chain Analysis of Anti-CCR4 Chimeric Antibody

Sugar chains of the anti-CCR4 chimeric antibody KM2760-1 derived from YB2/0 cell and anti-CCR4 chimeric antibody KM3060 derived from CHO/DG44 cell, prepared in Reference Example 1 were analyzed.

Into Hydraclub S-204 test tube, 100 μg of each antibody was put and dried with a centrifugal evaporator. The dried sample in the test tube was subjected to hydrazinolysis using Hydraclub manufactured by Hohnen. The sample was allowed to react with hydrazine at 110° C. for 1 hour by using a hydrazinolysis reagent manufactured by Hohnen hydrazinolysis [*Method of Enzymology*, 83, 263 (1982)]. After the reaction, hydrazine was evaporated under a reduced pressure, and the reaction tube was returned to room temperature by allowing it to stand for 30 minutes. Next, 250 µl of an acetylation reagent manufactured by Hohnen and 25 µl of acetic anhydride were added thereto, followed by thoroughly stirring for reaction at room temperature for 30 minutes. Then, 250 µl of the acetylation reagent and 25 µl of acetic anhydride were further added thereto, followed by thoroughly stirring for reaction at room temperature for 1 hour. The sample was frozen at −80° C. in a freezer and freeze-dried for about 17 hours. Sugar chains were recovered from the freeze-dried sample by using Cellulose Cartridge Glycan Preparation Kit manufactured by Takara Shuzo. The sample sugar chain solution was dried with a centrifugal evaporator and then subjected to fluorescence labeling with 2-aminopyridine [*J. Biochem.*, 95, 197 (1984)]. The 2-aminopyridine solution was prepared by adding 760 µl of HCl per 1 g of 2-aminopyridine (1×PA solution) and diluting the solution 10-fold with reverse osmosis purified water (10-folds diluted PA solution). The sodium cyanoborohydride solution was prepared by adding 20 µl of 1×PA solution and 430 µl of reverse osmosis purified water per 10 mg of sodium cyanoborohydride. To the sample, 67 µl of a 10 fold-diluted PA solution was added, followed by reaction at 100° C. for 15 minutes and spontaneously cooled, and 2 µl of sodium cyanoborohydride was further added thereto, followed by reaction at 90° C. for 12 hours for fluorescence labeling of the sample sugar chains. The fluorescence-labeled sugar chain group (PA-treated sugar chain group) was separated from excess reagent by using Superdex Peptide HR 10/30 column (manufactured by Pharmacia). This step was carried out by using 10 mM ammonium bicarbonate as the eluent at a flow rate of 0.5 ml/min and at a column temperature of room temperature, and using a fluorescence detector of 320 nm excitation wavelength and 400 nm fluorescence wavelength. The eluate was recovered 20 to 30 minutes after addition of the sample and dried with a centrifugal evaporator to be used as purified PA-treated sugar chains. Next, reverse phase HPLC analysis of the purified PA-treated sugar chains was carried out by using CLC-ODS column (manufactured by Shimadzu, φ6.0 nm×159 nm). The step was carried out at a column temperature of 55° C. and at a flow rate of 1 ml/min and at 320 nm excitation wavelength and 400 mm fluorescence wavelength in a fluorescence detector. The column was equilibrated with a 10 mM sodium phosphate buffer (pH 3.8) and elution was carried out for 80 minutes by a 0.5% 1-butanol linear density gradient. Each of the PA-treated sugar chain was identified by post source decay analysis of each peak of the separated PA-treated sugar chains by using matrix-assisted laser ionization time of flight mass spectrometry (MALDI-TOF-MS analysis), comparison of elution positions with standards of PA-treated sugar chain manufactured by Takara Shuzo, and reverse phase HPLC analysis after digestion of each PA-treated sugar chain using various enzymes.

Each of the sugar chain content was calculated from each of the peak area of PA-treated sugar chain by reverse HPLC analysis. A PA-treated sugar chain whose reducing end is not N-acetylglucosamine was excluded from the peak area calculation, because it is an impurity or a by-product during preparation of PA-treated sugar chain. When calculated by using peak areas, ratios of sugar chains in which 1-position of fucose is not bound to 6-position of N-acetylglucosamine in the reducing end of KM2760-1 and KM3060 through α-bond were 87% and 8%, respectively.

FIGS. 4A and 4B show elution patterns obtained by carrying out reverse phase HPLC analysis of each of PA-treated sugar chains prepared from KM2760-1 and KM3060, respectively. Using a sodium phosphate buffer (pH 3.8) as buffer A and a sodium phosphate buffer (pH 3.8)+0.5% 1-butanol as buffer B, the analysis was carried out by the following gradient shown in Table 2.

TABLE 2

| | Time (minute) | | | | |
|---|---|---|---|---|---|
| | 0 | 80 | 90 | 90.1 | 120 |
| Buffer B (%) | 0 | 60 | 60 | 0 | 0 |

Figure 4:
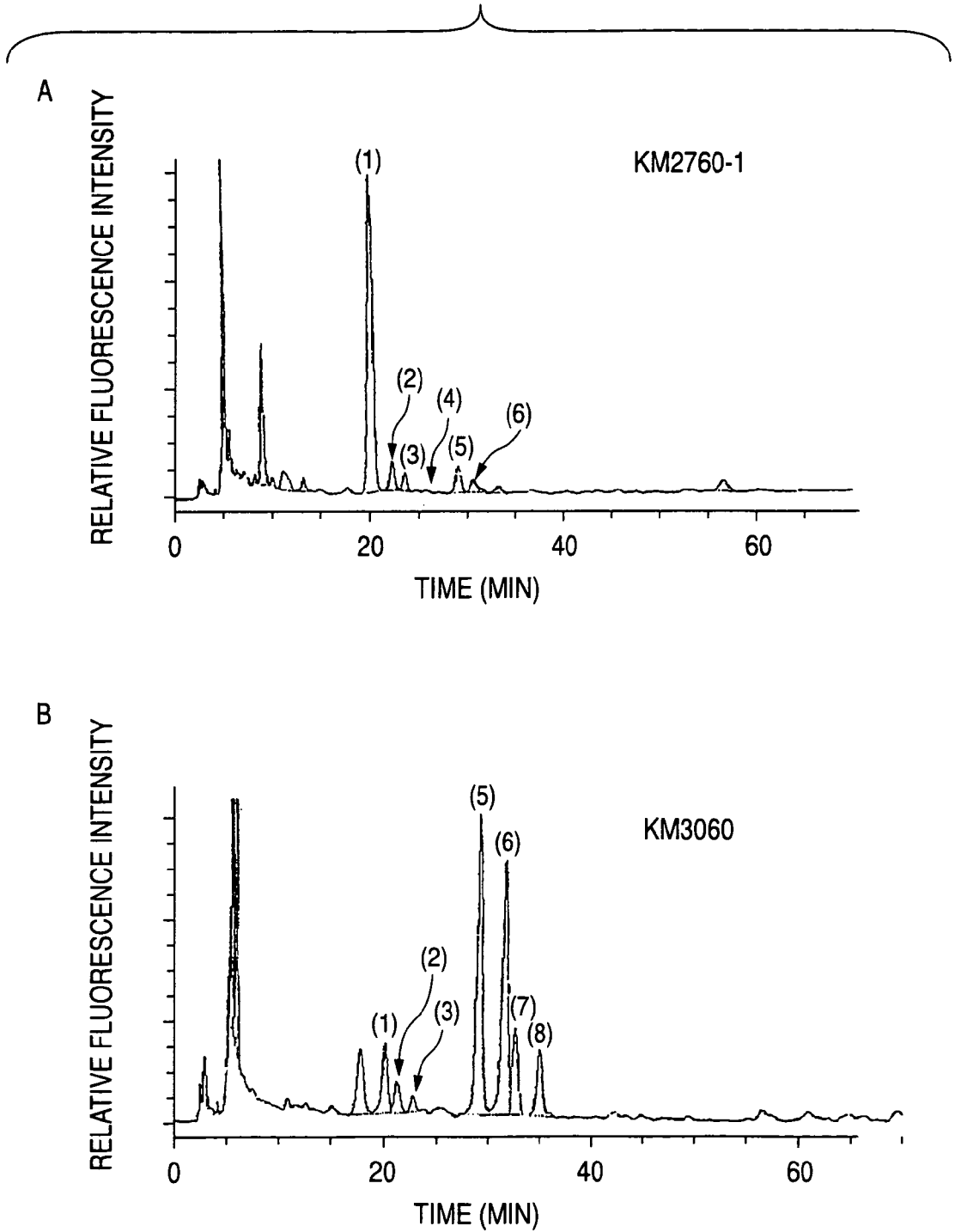
FIG. 4 shows results of sugar chain analysis of each anti-CCR4 chimeric antibody.

Peaks (1) to (8) shown in FIG. 4 show the following respective structures (1) to (8), respectively.

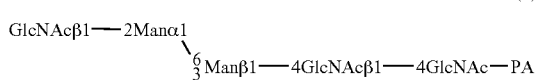

(1)

(2)

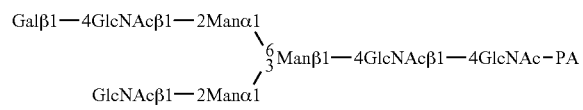

(3)

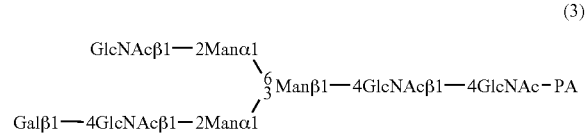

(4)

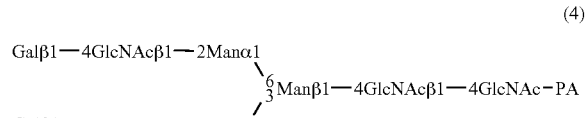

(5)

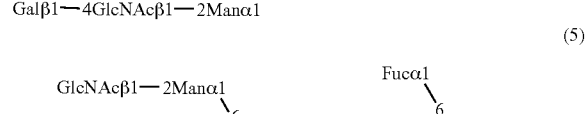

(6)

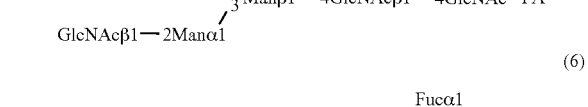

(7)

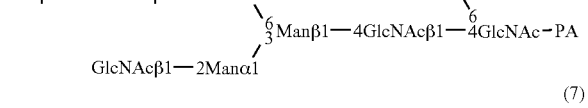

(8)

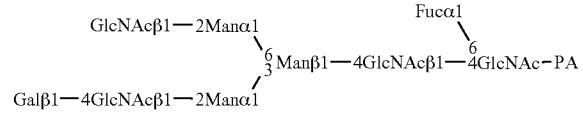

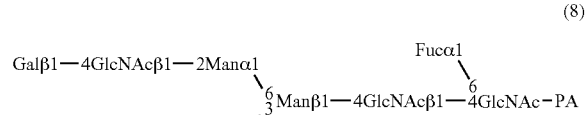

GlcNAc, Gal, Man, Fuc and PA indicate N-acetylglucosamine, galactose, mannose, fucose and a pyridylamino group, respectively. In FIG. 4, the ratio of the sugar chain group in which 1-position of fucose is not bound to 6-position of N-acetylglucosamine in the reducing end through α-bond was calculated from the area occupied by the peaks (1) to (4) among (1) to (8), and the ratio of the sugar chain group in which 1-position of fucose is not bound to 6-position of N-acetylglucosamine in the reducing end through α-bond was calculated from the area occupied by the peaks (5) to (8) among (1) to (8).

The ratios of sugar chains in which 1-position of fucose is not bound to 6-position of N-acetylglucosamine in the reducing end of KM2760-1 and KM 3060 through α-bond were 87% and 8%, respectively.

The results show that the antibody composition wherein the ratio of sugar chains in which 1-position of fucose is not bound to 6-position of N-acetylglucosamine in its reducing end through α-bond is higher has higher ADCC activity against target cells expressing antigens at various amounts as applied in the present experiments than the antibody composition wherein the ratio of sugar chains in which 1-position of fucose is not bound to 6-position of N-acetylglucosamine in its reducing end through α-bond is lower, and in particular, exerts ADCC activity against target cells which express an antigen in such a low amount that the antibody composition wherein the ratio of sugar chains in which 1-fucose is not bound to 6-position of N-acetylglucosamine in its reducing end through a bond is lower cannot exert ADCC activity.

That is, the results show that the antibody composition produced by an α1,6-fucose/lectin-resistant cell can exert ADCC activity against target cells which express an antigen in such a low amount that the antibody composition produced by an α1,6-fucose/lectin-unresistant cell cannot exert ADCC activity.

EXAMPLE 2

ADCC activity of anti-CCR4 chimeric antibodies having different ratio of sugar chain in which 1-position of fucose is not bound to 6-position of N-acetylglucosamine in the reducing end through α-bond and their effects on target cells:

1. Preparation of Anti-CCR4 Chimeric Antibodies Having Different Ratio of Sugar Chain in which 1-Position of Fucose is Not Bound to 6-Position of N-acetylglucosamine in the Reducing End through α-Bond As described in the item 3 of Example 1, the ratios of sugar chains in which 1-position of fucose is not bound to 6-position of N-acetylglucosamine in the reducing end of the anti-CCR4 chimeric antibody KM2760-1 derived from YB2/0 cell and the anti-CCR4 chimeric antibody KM2760-1 derived from CHO/DG44 through α-bond were 87% and 8%, respectively. Hereinafter, these samples are called anti-CCR4 chimeric antibody (87%) and anti-CCR4 chimeric antibody (8%), respectively.

In addition, the anti-CCR4 chimeric antibody (87%) and anti-CCR4 chimeric antibody (8%) were mixed at respective ratios of anti-CCR4 chimeric antibody (87%): anti-CCR4 chimeric antibody (8%)=22:57, 32:47 and 42:37. Sugar chains of these samples were analyzed according to the method in the item 7 of Example 1. Ratios of sugar chains in which 1-position of fucose is not bound to 6-position of N-acetylglucosamine in the reducing end through α-bond were 27%, 39% and 46%, respectively. Hereinafter, these samples are called anti-CCR4 chimeric antibody (27%), anti-CCR4 chimeric antibody (39%) and anti-CCR4 chimeric antibody (46%), respectively.

Figure 5:
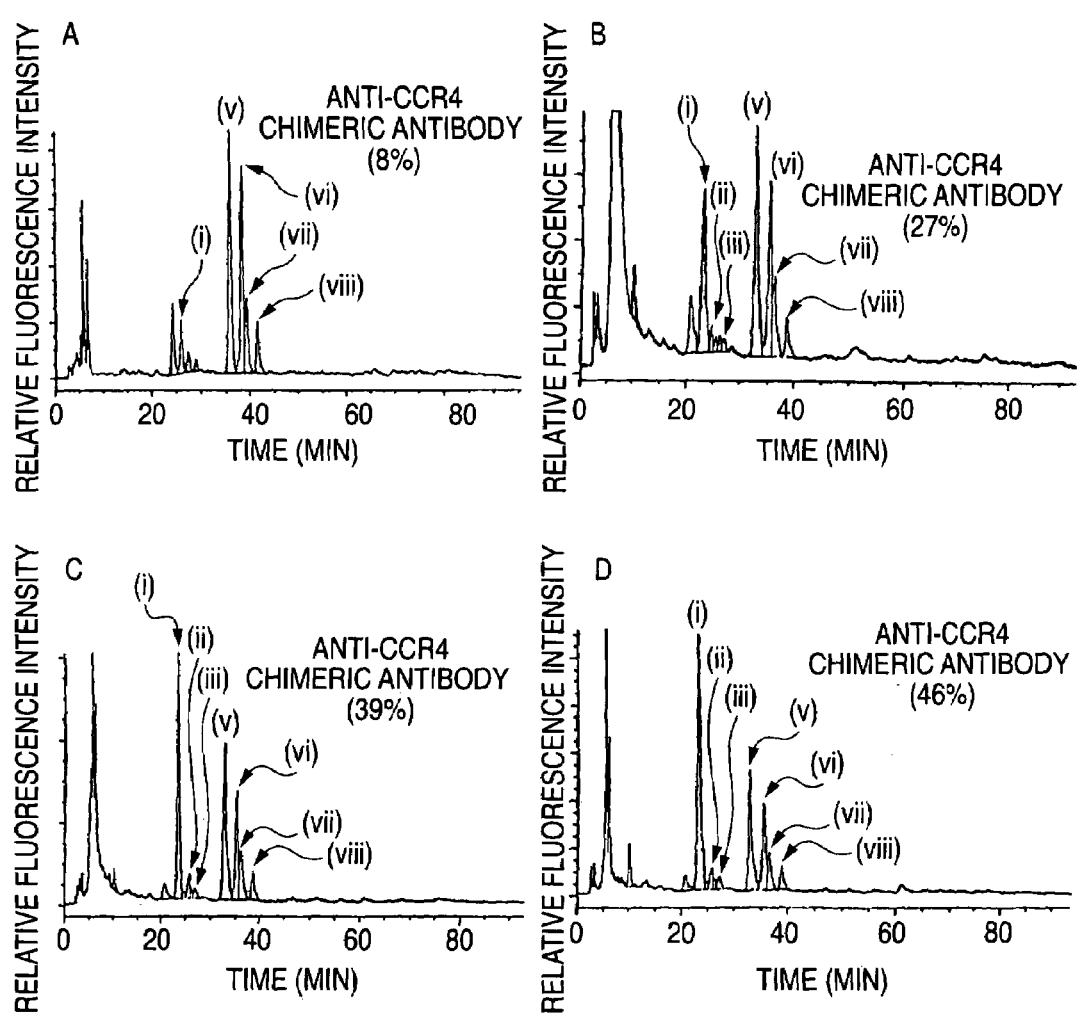
FIG. 5 shows a result of sugar chain analysis of anti-CCR4 chimeric antibodies having a different ratio of sugar chains in which 1-position of fucose is not bound to 6-position of N-acetylglucosamine in the reducing end through α-bond.

Results of the sugar chain analysis of respective samples are shown in FIG. 5. The ratio of a sugar chain in which 1-position of fucose is not bound to 6-position of N-acetylglucosamine in the reducing end through α-bond was shown as the mean value of the results of two experiments.

2. Evaluation of Binding Activity for CCR4 Partial Peptide (ELISA)

Binding activities of the anti-CCR4 chimeric antibody (27%), anti-CCR4 chimeric antibody (39%) and anti-CCR4 chimeric antibody (46%) prepared in the item 1 of this Example and the anti-CCR4 chimeric antibody (8%) to a CCR4 partial peptide were measured according to the method described in the item 2 of Example 1.

Figure 6:
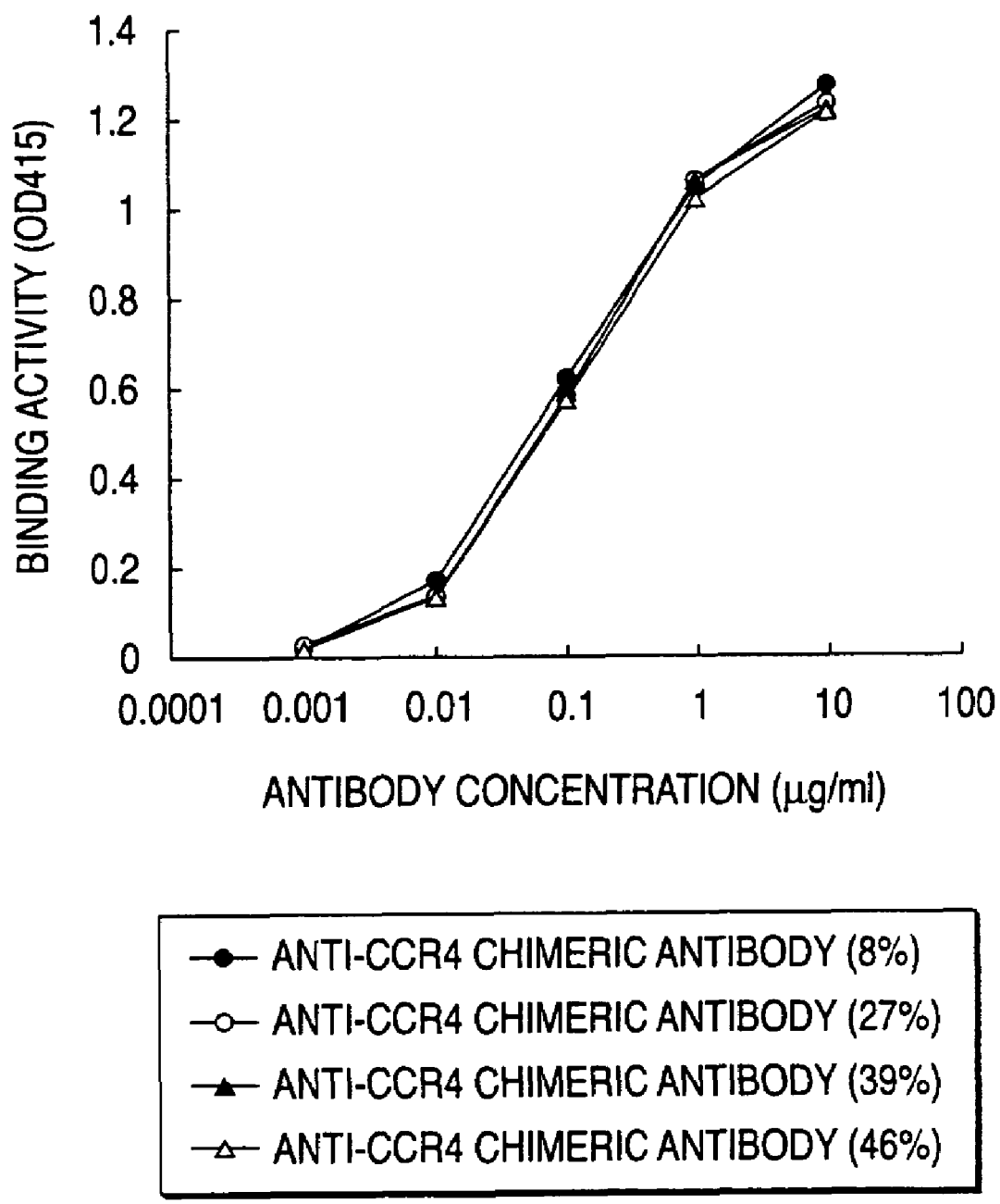
FIG. 6 shows antigen binding activities of anti-CCR4 chimeric antibodies having a different ratio of sugar chains in which 1-position of fucose is not bound to 6-position of N-acetylglucosamine in the reducing end through α-bond, measured by ELISA. The ordinate and the abscissa show the CCR4 peptide binding activity and the antigen concentration, respectively. "●", "○", "▲" and "Δ" show binding activities of anti-CCR4 chimeric antibody (8%), anti-CCR4 chimeric antibody (27%), anti-CCR4 chimeric antibody (39%), and anti-CCR4 chimeric antibody (46%), respectively.

As shown in FIG. 6, all of the four anti-CCR4 chimeric antibodies exerted equivalent binding activity to CCR4, and it was found that the ratio of a sugar chain in which 1-position of fucose is not bound to 6-position of N-acetylglucosamine in the reducing end through α-bond does not have influence on the antigen binding activity of these antibodies.

3. Evaluation of ADCC Activity for Human CCR4 Clones

ADCC activities of the anti-CCR4 chimeric antibody (27%), the anti-CCR4 chimeric antibody (39%) and the anti-CCR4 chimeric antibody (46%) prepared in the item 1 of this Example and the anti-CCR4 chimeric antibody (8%) were measured by using clones expressing various amounts of CCR4 as the target cells, and the relationship between the antigen number and the ratio of a sugar chain in which 1-position of fucose is not bound to 6-position of N-acetylglucosamine in the reducing end through α-bond was examined. As the target cells, three lines KC1067 (expression amount of CCR4: 4,650 molecules/cell), KC1063 (expression amount of CCR4: 15,300 molecules/cell) and KC1062 (expression amount of CCR4: 54,200 molecules/cell) were used among the 8 clones prepared in the item 1 of Example 1 expressing various amounts of CCR4. The ADCC activity of 4 anti-CCR4 chimeric antibodies having a different ratio of a sugar chain in which 1-position of fucose is not bound to 6-position of N-acetylglucosamine in the reducing end through α-bond was measured according to the method described in the item 5 of Example 1. The effector cells were collected from peripheral blood samples of three healthy donors A, B and C, and the antibody concentration at the time of the ADCC activity measurement was adjusted to give a final concentration of 1 μg/ml.

Figure 7:
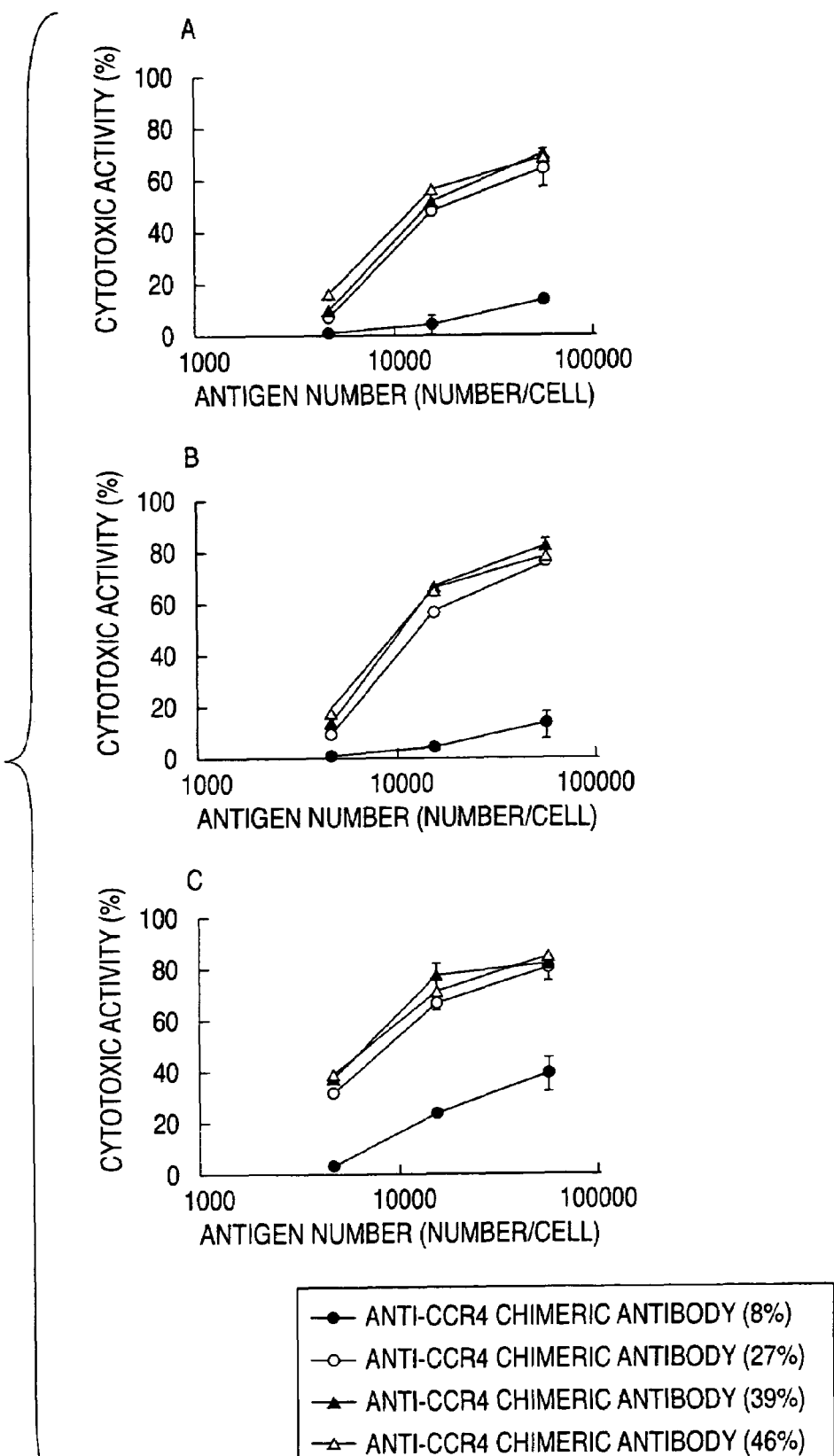
FIG. 7 shows ADCC activities of anti-CCR4 chimeric antibodies having a different ratio of a α-1,6-fucose-free sugar chain when clones which expresses CCR4 at various amounts were used as the target cells. The ordinate and the abscissa show the cytotoxic activity (%) and the number of CCR4 molecules on the target cell, respectively. Panels A, B and C show ADCC activities when monocytes collected from vein blood samples of healthy donors A, B and C, respectively, were used as the effector cells. "●", "○", "▲" and "Δ" show binding activities of anti-CCR4 chimeric antibody (8%), anti-CCR4 chimeric antibody (27%), anti-CCR4 chimeric antibody (39%), and anti-CCR4 chimeric antibody (46%), respectively.

FIG. 7 shows results of the measurement of ADCC activities of the anti-CCR4 chimeric antibodies having a different ratio of sugar chains in which 1-position of fucose is not bound to 6-position of N-acetylglucosamine in the reducing end through α-bond at an antibody concentration of 1 μg/ml and using the effector cells of three healthy donors (A, B and C). As shown in FIG. 7, the ADCC activity of the anti-CCR4 chimeric antibodies showed a tendency to increase in correlation with the antigen number and the ratio of sugar chains in which fucose is not bound to N-acetylglucosamine in the reducing end.

Plots of the anti-CCR4 chimeric antibody (27%), the anti-CCR4 chimeric antibody (39%) and the anti-CCR4 chimeric antibody (46%) of each donor, shown in FIG. 7, were approximated by a linear expression passing through two points of ADCC activities for the KC1067 (expression amount of CCR4: 4,650 molecules/cell) and KC1063 (expression amount of CCR4: 15,300 molecules/cell). The approximate expression is shown by the following equation (3).

$$Y = A \times Ln(X) - B \quad (3)$$

In equation (3), X is the antigen number, Y is an ADCC activity corresponding to X and A and B are coefficients. Values of A and B in respective plots were calculated by using a table calculation software Excel (manufactured by Microsoft). Table 3 shows the values of A and B in respective plots, the value of X obtained by substituting ADCC activity of the anti-CCR4 chimeric antibody (8%) upon KC1062 (CCR4 is 54,200 molecules/cell) for Y of the approximate expression, and the value of X÷54,200. The value of X represents the antigen number necessary for obtaining ADCC activity equivalent to the ADCC activity of the anti-CCR4 chimeric antibody (8%) upon target cells having a number of antigen molecules of 54,200 molecules/cell by using the anti-CCR4 chimeric antibody (27%), the anti-CCR4 chimeric antibody (39%) and the anti-CCR4 chimeric antibody (46%). Also, the value of X÷54,200 represents a ratio of the antigen number by which the anti-CCR4 chimeric antibody (27%), anti-CCR4 chimeric antibody (39%) and anti-CCR4 chimeric antibody (46%) can respectively show the same ADCC activity upon the anti-CCR4 chimeric antibody (8%).

TABLE 3

|  | A | B | X | X ÷ 54,200 |
|---|---|---|---|---|
| Donor A: Ratio of α-1,6-fucose-free sugar chain | | | | |
| 27% | 34.3 | 283 | 5610 | 1/9.66 |
| 39% | 36.0 | 294 | 5190 | 1/10.4 |
| 46% | 34.2 | 272 | 4290 | 1/12.6 |
| Donor B: Ratio of α-1,6-fucose-free sugar chain | | | | |
| 27% | 40.7 | 335 | 5280 | 1/10.3 |
| 39% | 43.9 | 357 | 4650 | 1/11.6 |
| 46% | 40.1 | 321 | 4190 | 1/12.9 |
| Donor C: Ratio of α-1,6-fucose-free sugar chain | | | | |
| 27% | 30.2 | 225 | 6300 | 1/8.61 |
| 39% | 34.0 | 251 | 4980 | 1/10.9 |
| 46% | 27.3 | 193 | 4760 | 1/11.4 |

As shown in Table 3, it was found that the value of X is decreased as the ratio of sugar chains in which 1-position of fucose is not bound to 6-position of N-acetylglucosamine in the reducing end through α-bond is increased in each case of the donors, and the value of X÷54,200 is also decreased, but each of the anti-CCR4 chimeric antibody (27%), the anti-CCR4 chimeric antibody (39%) and the anti-CCR4 chimeric antibody (46%) exerts the ADCC activity similar to that of the anti-CCR4 chimeric antibody (8%) at about 1/10 of the antigen number. The results show that equivalent ADCC activity of the antibody composition wherein the ratio of sugar chains in which 1-position of fucose is not bound to 6-position of N-acetylglucosamine in the reducing end through α-bond to be bound to the Fc region of the antibody composition is 20% or more can be obtained at 1/10 of the antigen number of the antibody composition wherein the ratio of sugar chains in which 1-position of fucose is not bound to 6-position of N-acetylglucosamine in the reducing end through α-bond to be bound to the Fc region of the antibody composition is less than 20%.

The results show that the antibody composition wherein the ratio of sugar chains in which 1-position of fucose is not bound to 6-position of N-acetylglucosamine in the reducing end through α-bond is 20% or more exerts ADCC activity to the target cell which expresses the antigen at such a low amount that the antibody composition wherein the ratio of sugar chains in which 1-position of fucose is not bound to 6-position of N-acetylglucosamine in the reducing end through α-bond is less than 20% cannot exerts ADCC activity.

Furthermore, the results show that a patient having a target cell which expresses the antigen at a low amount for which the antibody medicament of the present invention is particularly effective can be selected by using the target cell of the patient.

EXAMPLE 3

ADCC Activity of Anti-CCR4 Antibody Produced by Lectin-Resistant CHO/DG44 Cell (1) Preparation of Lectin-Resistant CHO/DG44

CHO/DG44 cells were grown until they reached a stage of just before confluent, by culturing in a 75 cm² flask for adhesion culture (manufactured by Greiner) in IMDM-FBS(10) medium [IMDM medium comprising 10% of FBS and 1× concentration of HT supplement (manufactured by GIBCO BRL)]. After washing the cells with 5 ml of PBS (manufactured by Invitrogen), 1.5 ml of 0.05% trypsin (manufactured by Invitrogen) diluted with PBS was added thereto and incubated at 37° C. for 5 minutes to peel the cells from the flask bottom. The peeled cells were recovered by centrifugation generally used in cell culture and suspended in IMDM-FBS (10)-HT(1) medium to give a density of 1×10⁵ cells/ml, and then 0.1 μg/ml of an alkylating agent N-rnethyl-N'-nitro-N-nitrosoguanidine (hereinafter referred to as "MNNG", manufactured by Sigma) was added or not added thereto. After culturing at 37° C. for 3 days in a $CO_2$ incubator (manufactured by TABAI), the culture supernatant was discarded, and the cells were again washed, peeled and recovered by the same operations, suspended in IMDM-FBS(10)-HT(1) medium and then inoculated into an adhesion culture 96 well plate (manufactured by Iwaki Glass) to give a density of 1×10³ cells/well. To each well, as the final concentration in medium, 1 mg/ml *Lens culinaris* agglutinin (hereinafter referred to as "LCA", manufactured by Vector), 1 mg/ml *Aleuria aurantia* agglutinin (*Aleuria aurantia* lectin; hereinafter referred to as "AAL", manufactured by Vector) or 1 mg/ml kidney bean agglutinin (*Phaseolus vulgaris* leucoagglutinin, hereinafter referred to as "L-PHA", manufactured by Vector) was added. After culturing at 37° C. for 2 weeks in a $CO_2$ incubator, the appeared colonies were obtained as lectin-resistant CHO/DG44. Regarding the obtained lectin-resistant CHO/DG44, an LCA-resistant clone was named clone CHO-LCA, an L-resistant clone was named clone CHO-AAL and an L-PHA-resistant clone was named clone CHO-PHA. When the resistance of these clones to various kinds of lectin was examined, it was found that the clone CHO-LCA was also resistant to AAL and the clone CHO-AAL was also resistant LCA. In addition, the clone CHO-LCA and the clone CHO-AAL also showed a resistance to a lectin which recognizes a sugar chain structure identical to the sugar chain structure recognized by LCA and AAL, namely a lectin which recognizes a sugar chain structure in which 1-position of fucose is bound to 6-position of N-acetylglucosamine residue in the reducing end through α-bond in the N-glycoside-linked sugar chain. Specifically, it was found that the clone CHO-LCA and the clone CHO-AAL can exert resistance and survive even in a medium supplemented with 1 mg/ml at a final concentration of a pea agglutinin (*Pisum sativum* agglutinin, hereinafter referred to as "PSA", manufactured by Vector). In addition, even when the alkylating agent MNNG was not added, it was able to obtain lectin-resistant clones by increasing the number of cells to be treated. Hereinafter, these clones were used in the following examples.

2. Preparation of Anti-CCR4 Human Chimeric Antibody-Producing Cell

An anti-CCR4 human chimeric antibody expression plasmid pKANTEX2160 was introduced into the three lectin-resistant clones obtained in the item 1 of this Example by the method described in Reference Example 1, and gene amplification by a drug MTX was carried out to prepare an anti-CCR4 human chimeric antibody-producing clone. The expression amount of the antibody was measured by the ELISA described in the item 2 of Reference Example 1, and antibody-expressing transformants were obtained from each of the clone CHO-LCA, the clone CHO-AAL and the clone CHO-PHA. Regarding each of the obtained transformants, a transformant derived from the clone CHO-LCA was named clone CHO/CCR4-LCA, a transformant derived from the clone CHO-AAL was named clone CHO/CCR4-AAL and a transformant derived from the clone CHO-PHA was named clone CHO/CCR4-PHA. Also, the clone CHO/CCR4-LCA, as a name of clone Nega-13, has been deposited on Sep. 26, 2001, as FERM BP-7756 in International Patent Organism Depositary, National Institute of Advanced Industrial Science and Technology (Tsukuba Central 6, 1, Higashi 1-Chome Tsukuba-shi, Ibaraki-ken, Japan).

3. Production of High ADCC Activity Antibody by Lectin-Resistant CHO Cell

Figure 8:
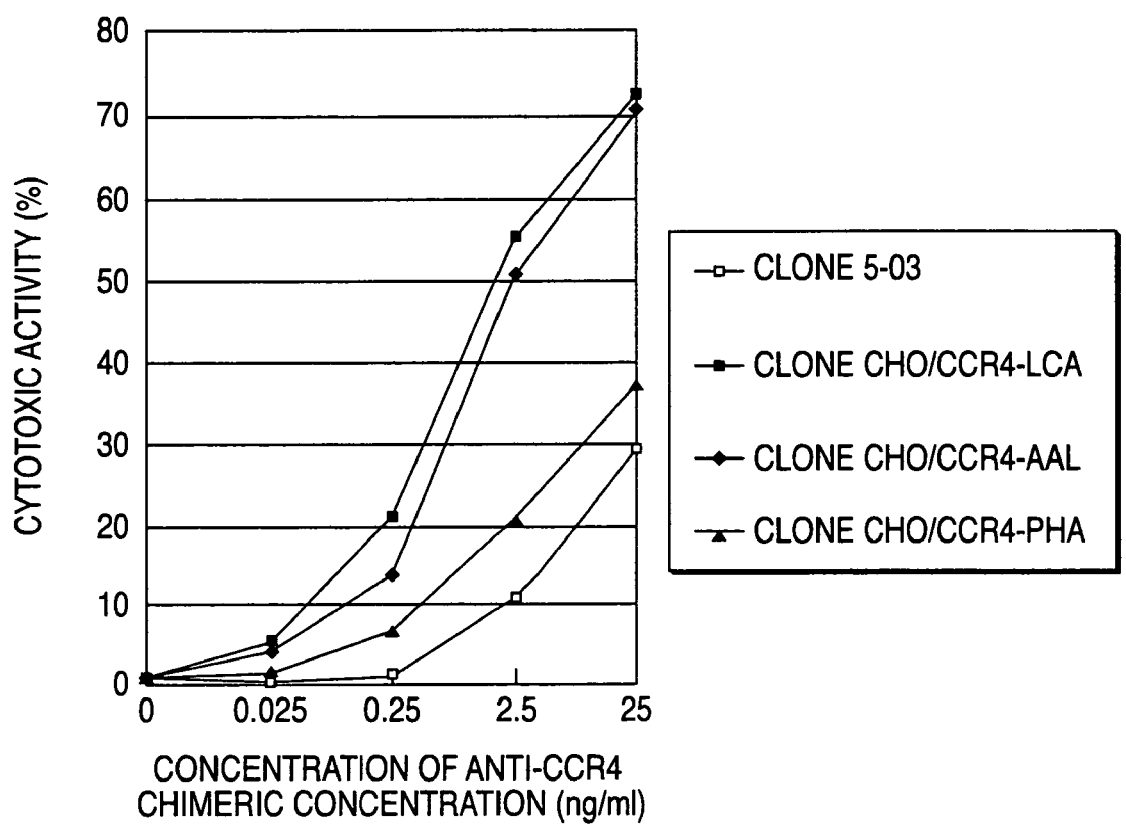
FIG. 8 shows ADCC activities of anti-CCR4 human chimeric antibodies produced by lectin-resistant clones. The ordinate and the abscissa show the cytotoxic activity and the antibody concentration, respectively. "□", "■", "◆" and "▲" show the activities of antibodies produced by the clones 5-03, CHO/CCR4-LCA, CHO/CCR4-AAL and CHO/CCR4-PHA, respectively.
Figure 9:
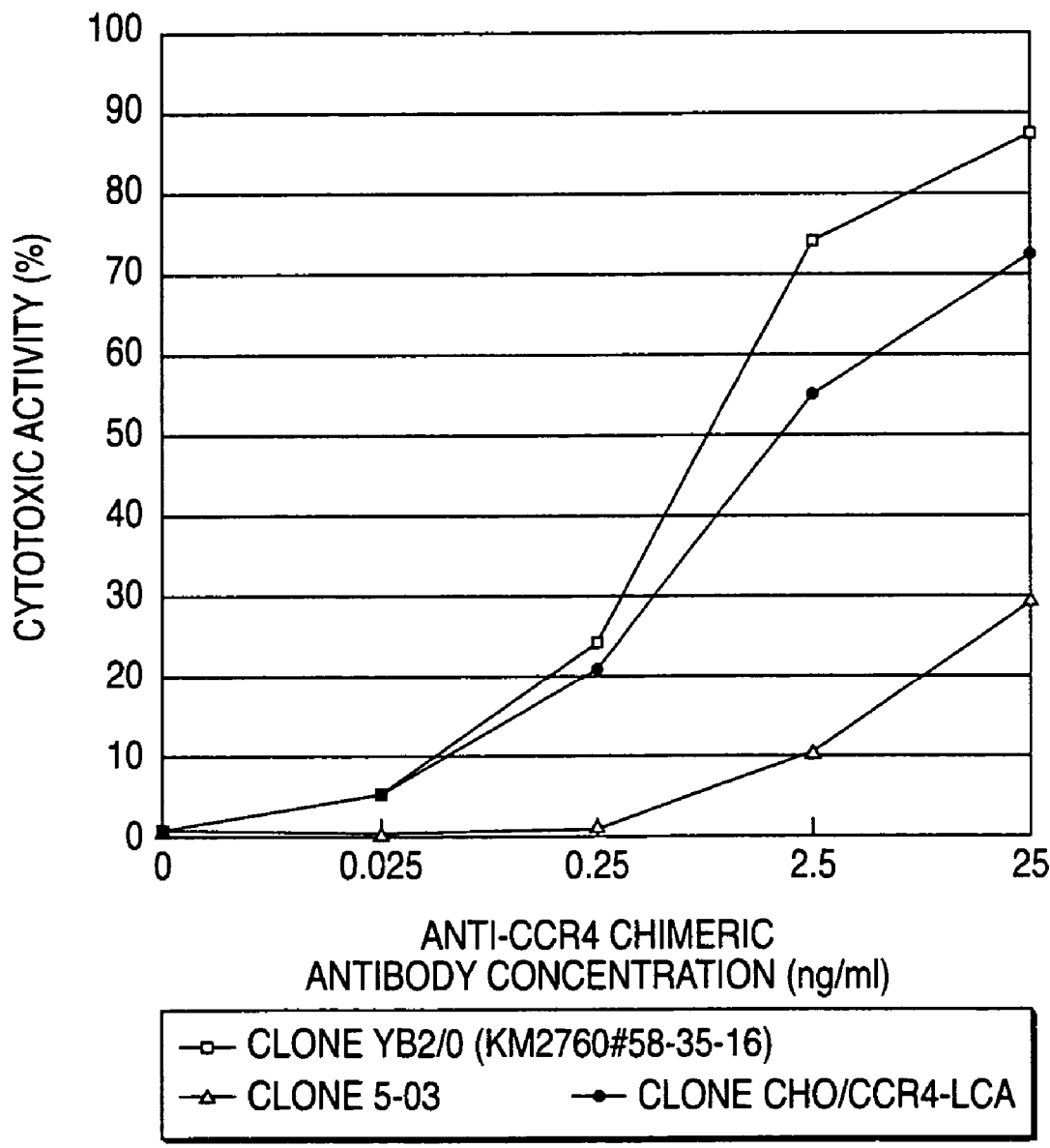
FIG. 9 shows ADCC activities of anti-CCR4 human chimeric antibodies produced by lectin-resistant clones. The ordinate and the abscissa show the cytotoxic activity and the antibody concentration, respectively. "□", "Δ" and "●" show activities of antibodies produced by the clones YB210 (KM2760#58-35-16), 5-03 and CHO/CCR4-LCA, respectively.

Using the three transformants obtained in the item 2 of this Example, purified antibodies were obtained by the method described in the item 3 of Reference Example 1. The antigen binding activity of each of the purified anti-CCR4 human chimeric antibodies was evaluated by the ELISA described in the item 2 of Reference Example 1. The antibodies produced by all transformants exerted an antigen binding activity similar to that of the antibody produced by clone 5-03 prepared in Reference Example 1 using general CHO/DG44 cell as the host. Using these purified antibodies, ADCC activity of each of the purified anti-CCR4 human chimeric antibodies was evaluated in accordance with the method described in the item 2 of Example 1. The results are shown in FIG. 8. In comparison with the antibody produced by the clone 5-03, about 100 fold-increased ADCC activity was observed in the antibodies produced by the clone CHO/CCR4-LCA and the clone CHO/CCR4-AAL. On the other hand, no significant increase in the ADCC activity was observed in the antibody produced by the clone CHO/CCR4-PHA. Also, when ADCC activities of the antibodies produced by the clone CHO/CCR4-LCA and YB2/0 cell-derived production clone were compared in accordance with the method described in the item 2 of Reference Example 1, it was found that the antibody produced by the clone CHO/CCR4-LCA shows higher ADCC activity than the antibody produced by the clone 5-03, similar to the case of the antibody KM2760-1 produced by the YB2/0 cell-derived clone prepared in Reference Example 1 (FIG. 5).

4. Sugar Chain Analysis of Antibody Produced by Lectin-Resistant CHO Cell

Sugar chains of the anti-CCR4 human chimeric antibodies purified in the item 3 of this Example were analyzed according to the method described in the item 3 of Example 1.

Table 4 shows the ratios of the sugar chain group in which 1-position of fucose is not bound to 6-position of N-acetyl-glucosamine in the complex N-glycoside-linked reducing end through α-bond (%), obtained by analyzing the sugar chains of the anti-CCR4 chimeric antibodies produced by the various lectin-resistant clones.

TABLE 4

| Antibody producing cell | Ratio of α-1,6-fucose-free sugar chain (%) |
| --- | --- |
| Clone 5-03 | 9 |
| Clone CHO/CCR4-LCA | 48 |
| Clone CHO/CCR4-AAL | 27 |
| Clone CHO/CCR4-PHA | 8 |

In comparison with the antibody produced by the clone 5-03, the ratio of the α1,6-fucose-free sugar chains was increased from 9% to 48% in the antibody produced by the clone CHO/CCR4-LCA when calculated from the analyzed peak area. The ratio of α1,6-fucose-free sugar chains was increased from 9% to 27% in the antibody produced by the clone CHO/CCR4-AAL. On the other hand, in the clone CHO/CCR4-PHA, changes in the sugar chain pattern and ratio of the α1,6-fucose-free sugar chains were hardly found when compared with the clone 5-03.

The results in Table 2 shows that the antibody composition wherein the ratio of sugar chains in which 1-position of fucose is not bound to 6-position of N-acetylglucosamine in the reducing end is 20% or more exerts higher cytotoxic activity to all target cells having a different expression amount of antigen used in the experiment than the antibody composition wherein the ratio of sugar chains in which 1-position of fucose is not bound to 6-position of N-acetylglucosamine in the reducing end is lower. Particularly, the results show that the antibody composition exerts ADCC activity to the target cell which express an antigen in such a low amount that the antibody composition wherein the ratio of sugar chains in which 2-position of fucose is not bound to 6-position of N-acetylglucosamine in the reducing end is less than 20% cannot exert ADCC activity. Accordingly, the antibody composition produced by the lectin-resistant CHO cell in this Example, the clone CHO/CCR4-LCA or the clone CHO/CCR-AAL, can exert ADCC activity to the target cell having such a low expression amount of antigen that the antibody composition produced by the clone 5-03 which is its parent cell, CHO/DG44 cell cannot exert ADCC activity.

EXAMPLE 4

Targeting Cytotoxic Activity Depending on Amount of Expressed Antigen by ADCC Activity of Anti-CD20 Chimeric Antibody Composition 1. Preparation of Transfectant Cell Different in Expression Amount of CD20

(1) Cloning of CD20 Gene

The gene containing the coding region of the amino acid sequence of human CD20 (hereinafter referred to as "CD20") was cloned according to the following procedure.

First, a specific forward primer (as represented by SEQ ID NO:2) containing a translation initiating codon and a specific reverse primer (as represented by SEQ ID NO:3) containing a translation terminating codon were designed based on the information of the nucleotide sequence of CD20 [*J. Exp. Med.* 167, 1975 (1988)].

Next, using a DNA polymerase (KOD DNA polymerase; manufactured by TOYOBO), a reaction mixture (20 mL) containing as a template 4 µL of human leukocyte 5'-STRETCH PLUS cDNA Library (manufactured by Clontech) was prepared [1 μL of KOD DNA polymerase, 1× concentration KOD buffer (manufactured by TOYOBO), 0.2 mmol/L dNTPs, 1 μmol/L of the above-mentioned gene-specific primer (SEQ ID NOs:2 and 3; synthesized by Genset under contract)], and subjected to PCR. The PCR was carried out by 45 cycles of a reaction at 94° C. for 40 seconds, 55° C. for 40 seconds and 74° C. for 75 seconds as one cycle. After completion of the PCR, the reaction mixture was subjected to 0.8% agarose gel electrophoresis to recover about 950 bp of a specific amplified fragment with about 70 μL of sterilized water. The recovered specific amplified fragment was used as a template in PCR to further amplify the DNA fragment. Using a DNA polymerase, Advantage cDNA PCR Kit (manufactured by Clontech), 50 μl of a reaction solution containing as a template 0.7 μL of the specific amplified fragment recovered above was prepared [1 μL of Advantage polymerase mix, 1× concentration buffer attached to Advantage cDNA PCR Kit, 0.04 mmol/L dNTPs, 0.6 μmol/L of the above-mentioned gene-specific primer (SEQ ID NOs:2 and 3)], and subjected to PCR. The PCR was carried out by 35 cycles of a reaction at 94° C. for 30 seconds and 72° C. for 3 minutes as one cycle. After completion of the PCR, the reaction mixture was purified with a QIA quick PCR Purification Kit (manufactured by QIAGEN), and the product was dissolved in 20 μL of sterilized water, digested with restriction enzymes PstI (manufactured by Takara Shuzo) and BamHI (manufactured by Takara Shuzo), and subjected to 0.8% agarose gel electrophoresis to recover about 950 bp of a specific amplified fragment.

Separately, a plasmid pBluescript II SK(−) (2.5 μg) was digested with a restriction enzyme PstI (manufactured by Takara Shuzo) and BamHI (manufactured by Takara Shuzo), and subjected to 0.8% agarose gel electrophoresis to recover about 2.9 kbp of a fragment.

The resulting amplified fragment derived from cDNA of CD20 and the fragment derived from plasmid pBluescript II SK(−) were ligated using a DNA Ligation Kit Ver.2.0 (manufactured by Takara Shuzo). Using this reaction mixture, *E. coli* DHA5α strain (manufactured by TOYOBO) was transformed, and each plasmid DNA was isolated from the resulting ampicillin resistant colonies according to a know method.

The nucleotide sequences of the respective inserted cDNAs were determined by using DNA sequencer 377 (manufactured by Perkin Elmer) and BigDye Terminator Cycle Sequencing FS Ready Reaction Kit (manufactured by Perkin Elmer) according to the attached manufacture's instruction. All of the inserted cDNAs of which the sequences were determined by this method were confirmed to encode the full length of ORF sequence of hFcγRIIIa cDNA. From these sequences, a plasmid DNA which has absolutely no miscoding of nucleotides in the sequence caused by PCR was selected, The plasmid was named pBSCD20.

The nucleotide sequence of the amino acid coding region in the resulting CD20 cDNA is shown by SEQ ID NO:4, and the corresponding amino acid sequence by SEQ ID NO:5.

(2) Construction of CD20 Expression Vector

A CD20 expression vector was constructed as follows.

After 3.0 μg of the plasmid pBSCD20 obtained in the above item (1) was digested with restriction enzymes BsiWI (manufactured by TOYOBO) and BamHI (manufactured by Takara Shuzo), the digested products were subjected to 0.8% agarose gel electrophoresis to recover about 920 bp of a fragment.

Separately, 2.0 μg of a plasmid pKANTEX93 for stable expression of humanized antibody in animal cell as described in WO97/10354 was digested with restriction enzymes BsiWI (manufactured by TOYOBO) and BamHI (manufactured by Takara Shuzo) and subjected to 0.8% agarose gel electrophoresis to recover about 9.2 kbp of a fragment.

The resulting DNA fragment containing shFcγRIIIa cDNA and a fragment derived from plasmid pKANTEX93 were ligated by using a DNA Ligation Kit Ver.2.0 (Takara Shuzo). Using this reaction mixture, *E. coli* DH5α strain (manufactured by TOYOBO) was transformed, and each plasmid DNA was isolated from the resulting ampicillin resistant colonies according to a know method.

Figure 10:
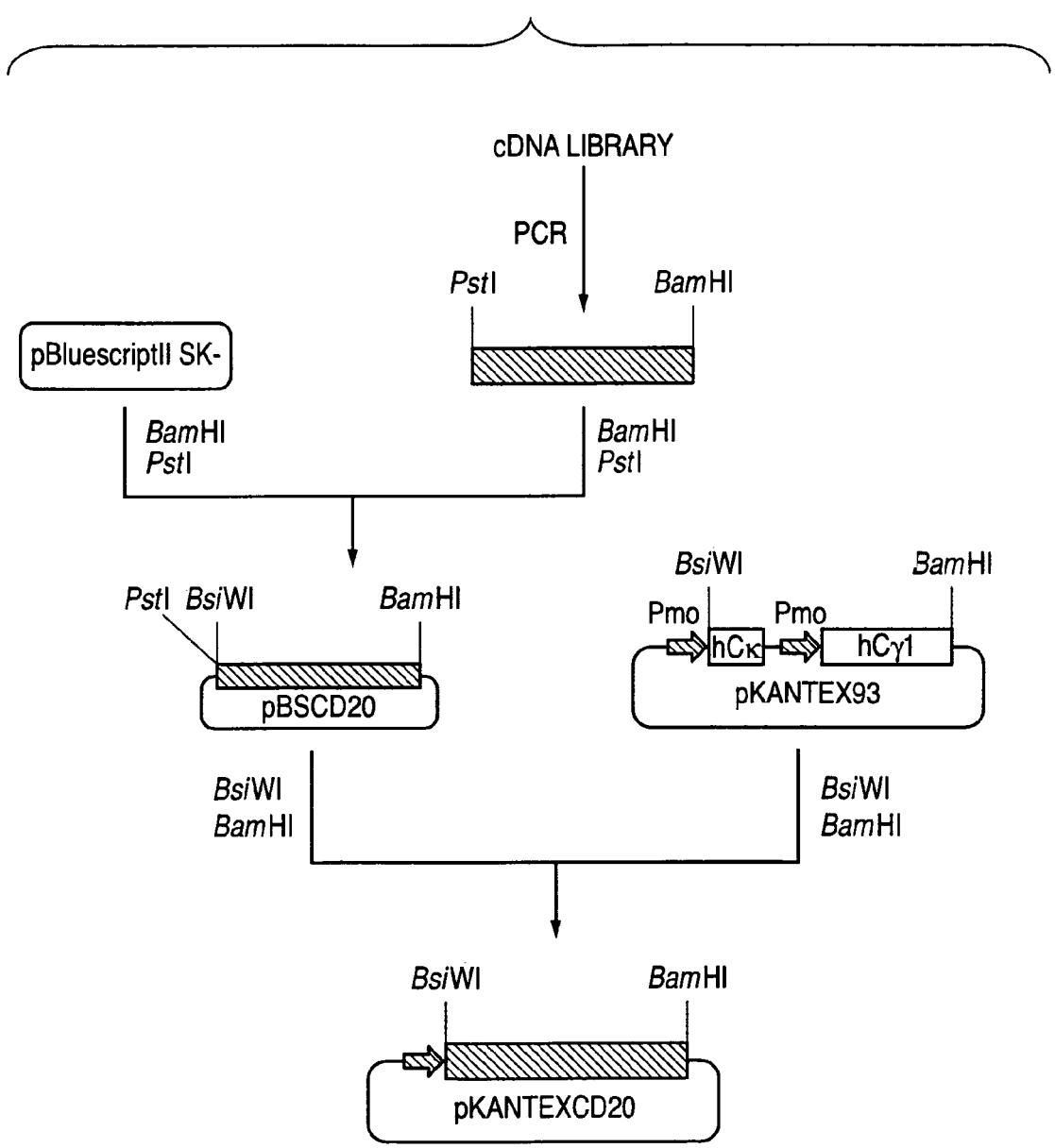
FIG. 10 shows a construction step of plasmid pKAN-TEXCD20. hCκ, hCγ1 and Pmo represent a human κ-chain C-region gene, a human IgG1C-region gene and a Moloney mouse leukemia virus promoter, respectively.

The nucleotide sequences of the respective inserted cDNAs were determined by using DNA sequencer 377 (manufactured by Perkin Elmer) and BigDye Terminator Cycle Sequencing FS Ready Reaction Kit (manufactured by Perkin Elmer) according to the attached manufacture's instructions. All of the plasmids in which the sequences were determined by this method were confirmed to contain the CD20 cDNA of interest. The expression plasmid was named as pKANTEXCD20. FIG. 10 shows a method for constructing pKANTEXCD20 described in this item.

(3) Selection of Clone Different in Expression Amount of CD20

An expression vector pKANTEXCD20 of CD20 gene stable in animal cells, prepared in the item (2), was introduced into a mouse thymoma cell line EL-4 cell (ATCC TIB-39) by electroporation. ELA cells were first suspended in PBS(−) (manufactured by GIBCO BRL) at 1×1 cells/500 μL, 10 μg of pKANTEXCD20 was added thereto, and the mixture was allowed to stand on ice for 10 minutes, then placed in a cuvette (manufactured by BioRad), and subjected to gene transduction at 260 V and 500 μFID. The mixture, after kept on ice for additional 10 minutes, were suspended into 200 mL of RPMI1640-FBS(10) medium, and dispensed at 100 μL/well into a 96-well plate. Twenty-four hours thereafter, the supernatant (100 μL/well) was removed, and 10% FCS-RPMI medium comprising 1 mg/mL of G418 was dispensed at 100 μL/well to give a final concentration of 0.5 mg/mL. Two weeks thereafter, several ten clones of single clones were selected and cultured for expansion.

In order to increase the expression of CD20 and increase the production of antibodies by utilizing a dhfr gene amplification system, a part of the clones were suspended in an RPMI1640-FBS(10) medium comprising 0.5 mg/mL of G418 and 50 nmol/mL of DHFR inhibitor MTX (manufactured by SIGMA) to give a density of 1 to 2×10⁵ cells/mL, and was dispensed at 2 mL into each well of a 24-well plate (manufactured by Greiner). The plate was incubated in a 5% CO₂ incubator at 37° C. for 1 to 2 weeks to induce into a transformant resistant to MTX at 50 nmol/L. The concentration of MTX was sequentially raised to 200 nmol/L and 1000 nmol/L, and finally plural transformants which were able to grow on an RPMI1640-FBS(10) medium containing 0.5 mg/mL of G418 and 200 nmol/L or 1000 nmol/L of MTX were obtained. The resulting transformants were subjected to cloning twice by a limiting dilution method.

(4) Selection of Clone Different in Expression Amount of CD20

Figure 11:
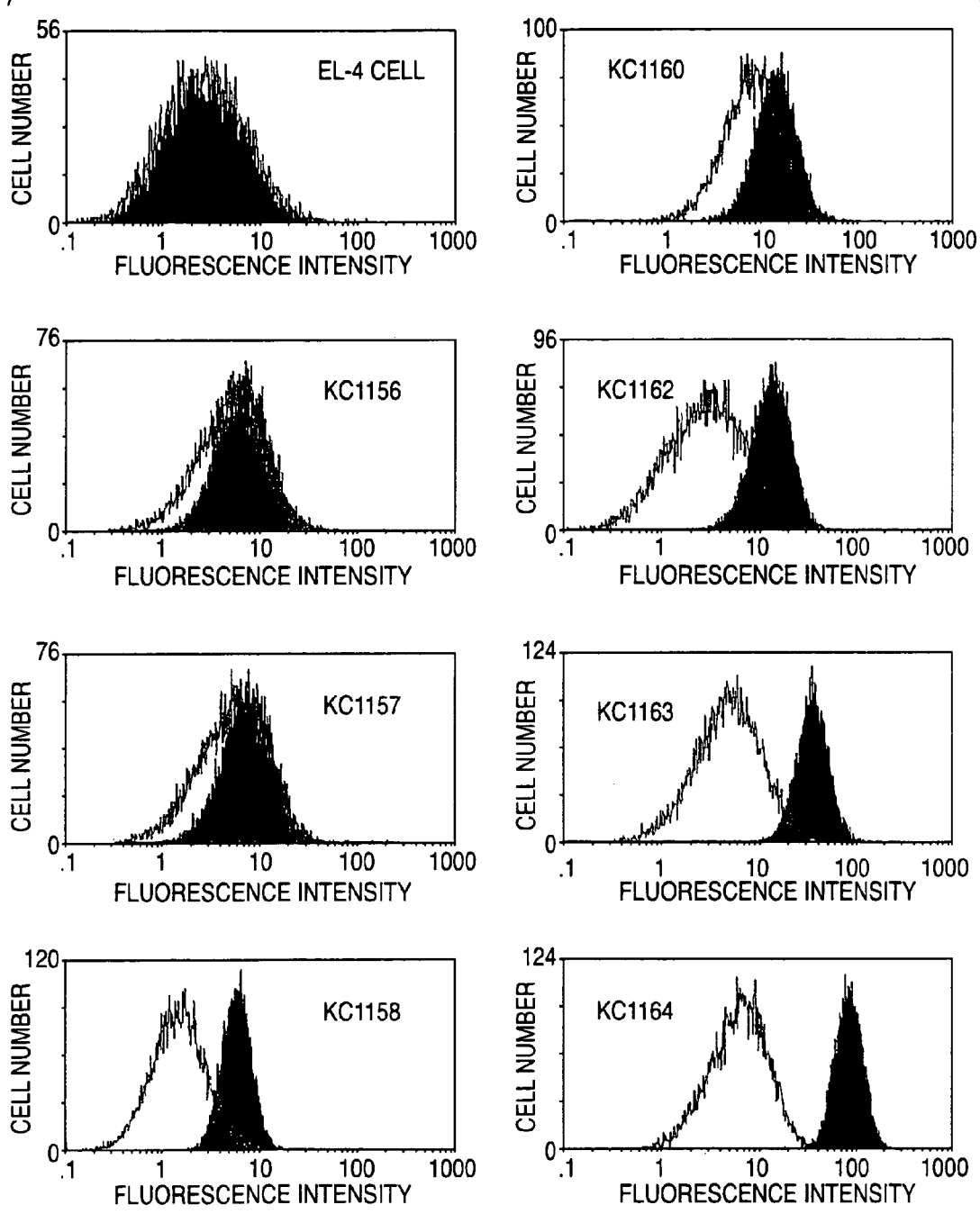
FIG. 11 shows histograms of CD20 expression in transfectant cells which express CCR4 at various amounts and in the parent cell line EL-4 cell which was analyzed by using a flow cytometer. The ordinate and the abscissa show the fluorescence intensity and the number of CD20 molecular per cell, respectively. The open square and the gray square show the histogram when mouse IgG2a was added and the histrogram when the anti-CD20 antibody was added, respectively.

The number of CD20 molecule expressed on each clone obtained in the item (3) was determined by using a flow cytometer. Each clone of 1×10⁶ cells was suspended in 100 μL of FACS buffer supplemented with 40 μg/mL of a mouse anti-human CD20 monoclonal antibody (manufactured by Coulter) and 5% normal mouse serum (manufactured by CEDERLANE) preventing non-specific staining, dispensed into a 96-well U-bottom plate, and allowed to react on ice for 60 minutes. As a negative control, mouse IgG2a (manufactured by DAKO) was added in place of the mouse anti-human CD20 monoclonal antibody. After washing twice with 200 μL/well of buffer, FITC-labeled anti-mouse IgG (manufactured by DAKO) diluted 20-fold with FACS buffer was added thereto at 100 μL/well. After the reaction on ice under shading for 60 minutes, the product was washed 3 times at 200 μL/well, finally suspended in 500 μL of PBS(-), and the fluorescence intensity was measured by using a flow cytometer EPICS XL-MCL (manufactured by COULTER). Seven clones having various fluorescence intensities were selected and named KC1156, KC1157, KC1158, KC1160, KC1162, KC1163 and KC1164 in order from the lowest expression amount. KC1160 and KC1163 are clones derived from the MTX 200 nM-resistant clone, and KC1164 is a clone derived from the MTX 1000 nM-resistant clone. FIG. 11 shows a histogram of fluorescence intensity of the respective clones and the parent EL-4 cell.

(5) Determination of the Number of CD20 Molecule Expressed on Clone Different in Expression Amount of CD20

The number of CD20 molecule expressed on the respective clones selected in the item (4) was determined by using a flow cytometer. As a standard specimen for determining the molecular number of CD20, standard beads on which the known number of mouse IgG had been coated (DAKO QEFI-KIT, manufactured by DAKO) were used to react with an FITC-labeled anti-mouse IgG in conditions as described in the item (4), and after washing, the fluorescence intensity was measured by means of a flow cytometer. According to the manufacture's instructions attached to the standard beads, a correlation equation between the fluorescence intensity and the molecular number adsorbed on beads was made, for which the fluorescence intensity of the respective clones obtained in the item (4) was applied to calculate the CD20 number of the respective clones. The background CD20 number was calculated based on the reaction with mouse IgG2a, and subtracted from the CD20 number obtained by the reaction with the mouse anti-human CD20 monoclonal antibody. The resulting number was finally regarded as the number of CD20 expressed on the respective clones. Table 5 shows the results of measurement, that is, the number of CD20 molecule expressed on the respective clones.

TABLE 5

| Cell name | Number of CD20 |
| --- | --- |
| EL-4 cell | $6.11 \times 10^2$ |
| KC1156 | $1.18 \times 10^4$ |
| KC1157 | $1.45 \times 10^4$ |
| KC1158 | $2.50 \times 10^4$ |
| KC1160 | $4.12 \times 10^4$ |
| KC1162 | $6.69 \times 10^4$ |
| KC1163 | $2.05 \times 10^5$ |
| KC1164 | $5.75 \times 10^5$ |

2. Determination of ADCC Activity Using Clone Different in Expression Amount of CD20 as Target Cell Regarding three species of antibodies, that is, anti-CD20 chimeric antibody KM3065, anti-CD20 chimeric antibody (44%) and Rituxan™ (wherein the ratios of a sugar chain in which 1-position of fucose is not bound to 6-position of N-acetylglucosamine in the reducing end bound to the Fc region were 96%, 44% and 6%, respectively) prepared in Reference Example 2, the relationship between the ADCC activity and the number of antigen was determined as follows using the clone different in expression amount of CD20 prepared in item 1 as the target cell.

(1) Preparation of a Target Cell Solution

Clones different in expression amount of CD20 were cultured in RPMI1640-FBS(10) medium supplemented with 500 μg/ml G418 sulfate (manufactured by Nacalai Tesque), and $1 \times 10^6$ cells thereof were prepared and allowed to react with 3.7 MBq equivalent of a radioactive substance $Na_2^{51}CrO_4$ at 37° C. for 60 minutes to label the cells. After the reaction, the cells were suspended in RPMI1640-FBS(10) medium and centrifuged. This operation was repeated 3 times for washing. The cells were again suspended in the culture medium and allowed to stand on ice at 4° C. for 30 minutes to release spontaneously the radioactive substance. After centrifugation, 5 ml of RPMI1640-FBS(10) medium was added thereto to give a density of $2 \times 10^5$ cells/ml, and the mixture was used as a target cell solution.

(2) Preparation of Effector Cell Solution

From a healthy human, 50 ml of venous blood was collected, 0.5 ml of heparin sodium (manufactured by Takeda Chem. Ind.) was added thereto, followed by mixing moderately. The mixture was separated by centrifugation using a Lymphoprep (manufactured by Nycomed Pharma AS) according to the manufacture's instructions to give a mononuclear leukocyte layer. The mixture was washed 3 times with RPMI1640-FBS(10) medium by centrifugation, and then suspended again into the medium to give a density of $2 \times 10^6$ cells/ml, and the resulting mixture was used as an effector cell solution.

(3) Determination of ADCC Activity

Into a 96-well U-bottom plate (manufactured by Falcon), 50 μl of the target cell solution prepared in the item (1) was dispensed at $1 \times 10^4$ cells/well. Then, an effector cell solution (100 μl) prepared in the item (2) was added thereto ($2 \times 10^5$ cells/well; the ratio of the effector cells to the target cells becomes 20:1). Additionally, three kinds of the anti-CD20 chimeric antibodies prepared in Reference Example 2, that is, Rituxan™, anti-CD20 chimeric antibody (44%) and KM3065, were added thereto to give a final concentration of 5 ng/ml, and allowed to react at 37° C. for 4 hours. After the reaction, the plate was centrifuged, and $^{51}Cr$ contained in the supernatant was counted with a γ-counter. The amount of spontaneously released $^{51}Cr$ was determined in the same manner as above on the supernatant in which the medium only was used in place of the effector cell solution and the antibody solution. The total amount of the released $^{51}Cr$ was determined in the same manner as above on the supernatant in which the medium only was used in place of the antibody solution and 1 N-hydrochloric acid was added in place of the effector cell solution. The ADCC activity was determined from the above equation (1).

Figure 12:
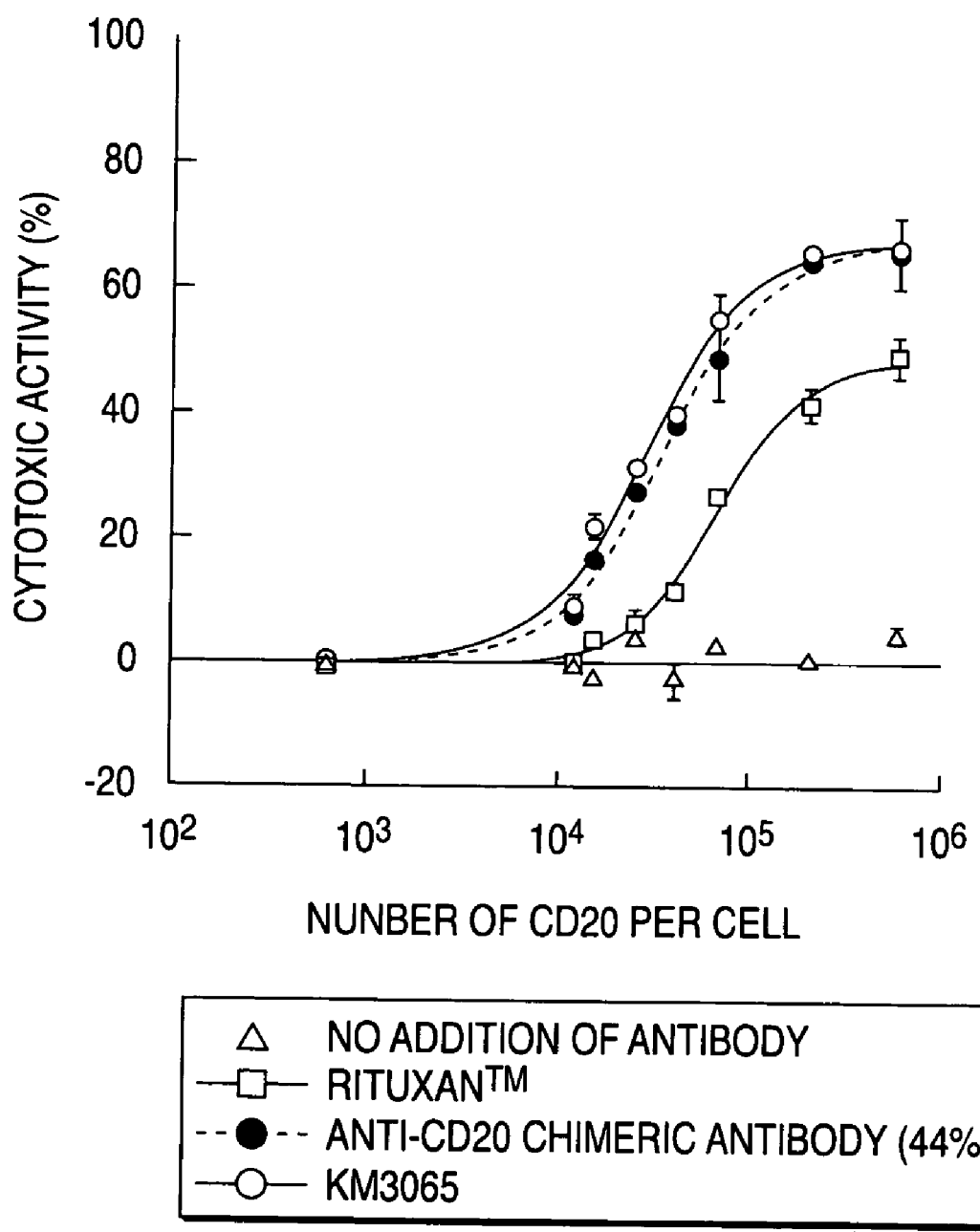
FIG. 12 shows ADCC activities of various anti-CD20 chimeric antibodies when clones which express CD20 at various amounts were used as target cells. The ordinate and the abscissa show the cytotoxic activity and the number of CD20 molecules per cell, respectively. "□", "●", "○" and "Δ" show cytotoxic activities in the presence of Rituxan™, in the presence of the anti-CD20 chimeric antibody, in the presence of KM3065 and in the absence of antibody, respectively.

FIG. 12 shows the relationship between the resulting ADCC activity and the number of CD20 molecule expressed on the respective target cells prepared in item 1. All the three kinds of anti-CD20 chimeric antibodies had the variable ADCC activity depending on the number of antigen. In this situation, the ADCC activity of KM3065 was approximately the same as that of the anti-CD20 chimeric antibody (44%), and both were far higher than that of Rituxan™. The plots of KM3065 were approximated by the following equation (4) as a result of use of a data analyzing software KaleidaGraph™ (manufactured by SYNERGY SOFTWARE).

$$y=(-67.81/1+(x/28942)^{1.58}))+68.19 \quad (4)$$

In equation (4), x and y represent the number of CD20 and a cytotoxic activity, respectively.

The plots of the anti-CD20 chimeric antibody (44%) were approximated by the following equation (5).

$$y=(-67.98/(1+(x/33601)^{1.55}))+67.59 \quad (5)$$

Rituxan™ showed 41.8% of cytotoxic activity for KC1163 (the number of CD20: 205,000/cell). The value was adapted to equations (4) and (5) to calculate the number of CD20 required for exhibiting the cytotoxic activity equivalent to that of Rituxan™ for KC1163, and it was found that the number was 38,500/cell and 46,100/cell, respectively. That is, it was found that that KM3065 or anti-CD20 chimeric antibody (44%) has the same degree of ADCC activity in the approximately 1/5 CD20 number as that of Rituxan™. It was also found that Rituxan™ could never reach the cytotoxic activity of KM3065 or anti-CD20 chimeric antibody (44%) even in much higher CD20 number because it was saturated in a lower activity level.

These results show that an antibody composition in which the ratio of sugar chains in which 1-position of fucose is not bound to 6-position of N-acetylglucosamine in the reducing end through α-bond is higher has a higher cytotoxic activity than an antibody composition in which the ratio of sugar chains in which 1-position of fucose is not bound 6-position of N-acetylglucosamine in the reducing end through α-bond is lower. In particular, the results show that an antibody composition in which the ratio of sugar chains in which 1-position of fucose is not bound 6-position of N-acetylglucosamine in the reducing end through α-bond is higher is able to exert ADCC activity even to the target cells which express an antigen in such a low amount that the antibody composition wherein the ratio of sugar chains in which 1-fucose is not bound to 6-position of N-acetylglucosamine in the reducing end through a bond is lower is not able to exert ADCC activity.

In other words, the results show that the antibody composition produced by α1,6-fucose/lectin-resistant cells can exert ADCC activity to the target cell which expresses an antigen in such a low amount that an antibody composition produced by α1,6-fucose/lectin intolerant cells cannot exhibit the ADCC activity.

Reference Example 1

1. Production of Cell Stably Producing Anti-CCR4 Chimeric Antibody

Cells capable of stably producing an anti-CCR4 chimeric antibody were prepared as follows by using a tandem type expression vector pKANTEX2160 for an anti-CCR4 chimeric antibody described in WO01/64754.

(1) Preparation of Antibody-Producing Cell Using Rat Myeloma YB2/0 Cell

After introducing 10 μg of the anti-CCR4 chimeric antibody expression vector pKANTEX2160 into 4×10⁶ cells of rat myeloma YB2/0 cell (ATCC CRL 1662) by electroporation [*Cytotechnology*, 3, 133 (1990)], the cells were suspended in 40 ml of Hybridoma-SFM-FBS(5) [Hybridoma-SFM medium (manufactured by Invitrogen) comprising 5% FBS (manufactured by PAA Laboratories)] and dispensed at 200 μl/well into a 96 well culture plate (manufactured by Sumitomo Bakelite). After culturing at 37° C. for 24 hours in a 5% $CO_2$ incubator, G418 was added to give a concentration of 1 mg/ml, followed by culturing for 1 to 2 weeks. Culture supernatant was recovered from wells in which growth of transformants showing G418 resistance was observed by formation of colonies, and antigen binding activity of the anti-CCR4 chimeric antibody in the supernatant was measured by the ELISA described in the item 2 of this Example.

Regarding the transformants in wells in which production of the anti-CCR4 chimeric antibody was observed in culture supernatants, in order to increase an amount of the antibody production using a DHFR gene amplification system, each of them was suspended in the Hybridoma-SFM-FBS(5) medium comprising 1 mg/ml G418 and 50 nM DHFR inhibitor MTX (manufactured by SIGMA) to give a density of 1 to 2×10⁵ cells/ml, and the suspension was dispensed at 1 ml into each well of a 24 well plate (manufactured by Greiner). After culturing at 37° C. for 1 to 2 weeks in a 5% $CO_2$ incubator, transformants showing 50 nM MTX resistance were induced. Antigen binding activity of the anti-CCR4 chimeric antibody in culture supernatants in wells in which growth of transformants was observed was measured by the ELISA described in the item 2 of this Example.

Regarding the transformants in wells in which production of the anti-CCR4 chimeric antibody was observed in culture supernatants, the MTX concentration was increased by the same method, and a transformant capable of growing in the Hybridoma-SFM-FBS(5) medium comprising 200 nM OX and of producing the anti-CCR4 chimeric antibody in a large amount was finally obtained. The obtained transformant was made into a single cell (cloning) by limiting dilution twice, and the obtained clone was named KM2760-1#58-35-16. In this case, according to the method for determining the transcription product of α1,6-fucosyltransferase gene shown in WO00/61739, a clone producing a relatively small amount of the transcription product was selected and used as a suitable clone. The selected clone was a lectin-resistant clone.

(2) Preparation of Antibody-Producing Cell Using CHO/DG44 Cell

After introducing 4 μg of the anti-CCR4 chimeric antibody expression vector pKANTEX2160 into 1.6×10⁶ cells of CHO/DG44 cell by electroporation [*Cytotechnology*, 3, 133 (1990)], the cells were suspended in 10 ml of IMDM-dFBS (10)-HT(1) [DPMM medium (manufactured by Invitrogen) comprising 10% dFBS (manufactured by Invitrogen) and 1× concentration of HT supplement (manufactured by Invitrogen)] and dispensed at 100 μl/well into a 96 well culture plate (manufactured by Iwaki Glass). After culturing at 37° C. for 24 hours in a 5% $CO_2$ incubator, the medium was changed to IMDM-dFBS(10) (IMDM medium comprising 10% of dialyzed FBS), followed by culturing for 1 to 2 weeks. Culture supernatants were recovered from wells in which the growth was observed due to formation of a transformant showing HT-independent growth, and an amount of production of the anti-CCR4 chimeric antibody in the supernatant was measured by the ELISA described in the item 2 of this Example.

Regarding the transformants in wells in which production of the anti-CCR4 chimeric antibody was observed in culture supernatants, in order to increase an amount of the antibody production using a DIFR gene amplification system, each of them was suspended in the IMDM-dFBS(10) medium comprising 50 nM MTX to give a density of 1 to 2×10⁵ cells/ml, and the suspension was dispensed at 0.5 ml into each well of a 24 well plate (manufactured by Iwaki Glass). After culturing at 37° C. for 1 to 2 weeks in a 5% $CO_2$ incubator, transformants showing 50 nM MTX resistance were induced. Regarding the transformants in wells in which the growth was observed, the MTX concentration was increased to 200 nM by the same method, and a transformant capable of growing in the IMDM-dFBS(10) medium comprising 200 nM MTX and of producing the anti-CCR4 chimeric antibody in a large amount was finally obtained. The obtained transformant was named clone 5-03.

2. Binding Activity to CCR4 Partial Peptide (ELISA)

Compound 1 (SEQ ID NO:1) was selected as a human CCR4 extracellular region peptide capable of reacting with the anti-CCR4 chimeric antibody. In order to use it in the activity measurement by ELISA, a conjugate with BSA (bovine serum albumin) (manufactured by Nacalai Tesque) was prepared by the following method and used as the antigen. That is, 100 ml of a DMSO solution comprising 25 mg/ml SMCC [4-(N-maleimidomethyl)-cyclohexane-1-carboxylic acid N-hydroxysuccinimide ester] (manufactured by Sigma) was added dropwise to 900 ml of a 10 mg BSA-containing PBS solution under stirring with a vortex, followed by gently stirring for 30 minutes. To a gel filtration column such as NAP-10 column or the like equilibrated with 25 ml of PBS, 1 ml of the reaction solution was applied and then eluted with 1.5 ml of PBS and the resulting eluate was used as a BSA-SMCC solution (BSA concentration was calculated based on $A_{280}$ measurement). Next, 250 ml of PBS was added to 0.5 mg of Compound 1 and then completely dissolved by adding 250 ml of DMF, and the BSA-SMCC solution was added thereto under vortex, followed by gently stirring for 3 hours. The reaction solution was dialyzed against PBS at 4° C. overnight, sodium azide was added thereto to give a final concentration of 0.05%, and the mixture was filtered through a 0.22 mm filter to be used as a BSA-compound 1 solution.

The prepared conjugate was dispensed at 0.05 μg/ml and 50 μl/well into a 96 well EIA plate (manufactured by Greiner) and allowed to stand for adhesion at 4° C. overnight. After washing each well with PBS, 1% BSA-PBS was added thereto at 100 μl/well and allowed to react at room temperature to block the remaining active groups. After washing each well with PBS containing 0.05% Tween 20 (hereinafter referred to as "Tween-PBS"), a culture supernatant of a transformant was added at 50 μl/well and allowed to react at room temperature for 1 hour. After the reaction, each well was washed with Tween-PBS, and then a peroxidase-labeled goat anti-human IgG(γ) antibody solution (manufactured by American Qualex) diluted 6000 times with 1% BSA-PBS as the secondary antibody was added at 50 μl/well and allowed to react at room temperature for 1 hour. After the reaction and subsequent washing with Tween-PBS, the ABTS substrate solution was added at 50 μl/well for color development, and 20 minutes thereafter, the reaction was stopped by adding a 5% SDS solution at 50 μl/well. Thereafter, the absorbance at $OD_{415}$ was measured. The anti-CCR4 chimeric antibody obtained in the item 1 of this Reference Example showed the binding activity to CCR4.

3. Purification of Anti-CCR4 Chimeric Antibody (1) Culturing of Antibody-Producing Cell Derived from YB2/0 Cell and Purification of Antibody The anti-CCR4 chimeric antibody-expressing transformant cell clone KM760-1#58-35-16 obtained in the item 1 of this Reference Example was suspended in Hybridoma-SFM (manufactured by Invitrogen) medium comprising 200 nM MTX and 5% of Daigo's GF21 (manufactured by Wako Pure Chemical Industries) to give a density of $2 \times 10^5$ cells/ml and subjected to fed-batch shaking culturing with a spinner bottle (manufactured by Iwaki Glass) in a constant temperature chamber of 37° C. After culturing for 8 to 10 days, the anti-CCR4 chimeric antibody was purified from the culture supernatant recovered by using Prosep-A (manufactured by Millipore) column and gel filtration. The purified anti-CCR4 chimeric antibody was named KM2760-1.

(2) Culturing of Antibody-Producing Cell Derived from CHO-DG44 Cell and Purification of Antibody The anti-CCR4 chimeric antibody-producing transformant clone 5-03 obtained in the item 1 of this Reference Example was cultured in IMDM-dFBS(10) medium at 37° C. in a 5% $CO_2$ incubator in a 182 cm² flask (manufactured by Greiner). When the cell density reached confluent after several days, the culture supernatant was discarded, and the cells were washed with 25 ml of PBS buffer and then mixed with 35 ml of EXCELL 301 medium (manufactured by JRH). After culturing at 37° C. for 7 days in a 5% $CO_2$ incubator, the culture supernatant was recovered. The anti-CCR4 chimeric antibody was purified from the culture supernatant by using Prosep-A (manufactured by Millipore) column in accordance with the manufacture's instructions. The purified anti-CCR4 chimeric antibody was named KM3060.

When the binding activity to CCR4 of KM2760-1 and KM3060 was measured by ELISA, they showed equivalent binding activity.

4. Analysis of Purified Anti-CCR4 Chimeric Antibody

The molecular weight and purity of 4 μg of each of the two kinds of the anti-CCR4 chimeric antibodies obtained in the item 1 were analyzed by SDS-PAGE in accordance with a known method [*Nature*, 227, 680 (1970)]. In each of the purified anti-CCR4 chimeric antibodies, a single band corresponding to the molecular weight of about 150 Kd was found under non-reducing conditions, and two bands of about 50 Kd and about 25 Kd were found under reducing conditions. The molecular weights almost coincided with the molecular weights deduced from the cDNA nucleotide sequences of antibody H chain and L chain (H chain; about 49 Kd, L chain: about 23 Kd, whole molecule: about 144 Kd) and coincided with reports stating that an IgG type antibody has a molecular weight of about 150 Kd under non-reducing conditions and is degraded into H chain having a molecular weight of about 50 Kd and L chain having a molecular weight of about 25 Kd under reducing conditions caused by cutting an S—S bond in the molecule (*Antibodies*, Chapter 14, *Monoclonal Antibodies: Principles and Practice*), thus confirming that the anti-CCR4 chimeric antibody was expressed and purified as an antibody molecule having a correct structure.

Reference Example 2

Preparation of an Anti-CD20 Human Chimeric Antibody

1. Preparation of Anti-CD20 Vector for Expression of Human Chimeric Antibody (1) Construction of a cDNA Encoding the V Region of L Chain of an Anti-CD20 Mouse Monoclonal Antibody A cDNA (represented by SEQ ID NO:6) encoding the amino acid sequence of VL of an anti-CD20 mouse monoclonal antibody 2B8 described in WO94/11026 was constructed by PCR as follows.

First, binding nucleotide sequences of primers for amplification at the time of the PCR and restriction enzyme recognizing sequences for cloning into a vector for humanized antibody expression were added to the 5'-terminal and 3'-terminal of the nucleotide sequence of the VL described in WO94/11026. A designed nucleotide sequence was divided from the 5'-terminal side into a total of 6 nucleotide sequences each having about 100 bases (adjacent nucleotide sequences are designed in such a manner that their termini have an overlapping sequence of about 20 nucleotides), and 6 synthetic DNA fragments, actually those represented by SEQ ID NOs:7, 8, 9, 10, 11 and 12, were prepared from them in alternate order of a sense chain and an antisense chain (consigned to GENSET).

Each oligonucleotide was added to 50 µl of a reaction mixture [KOD DNA polymerase-attached PCR Buffer #1 (manufactured by TOYOBO), 0.2 mM dNTPs, 1 mM magnesium chloride, 0.5 µM M13 primer M4 (manufactured by Takara Shuzo) and 0.5 µM M13 primer RV (manufactured by Takara Shuzo)] to give a final concentration of 0.1 µM, and using a DNA thermal cycler GeneAmp PCR System 9600 (manufactured by Perkin Elmer), the reaction was carried out by heating at 94° C. for 3 minutes, adding 2.5 units of KOD DNA Polymerase (manufactured by TOYOBO) thereto, subsequent 25 cycles of heating at 94° C. for 30 seconds, 55° C. for 30 seconds and 74° C. for 1 minute as one cycle and then further heating at 72° C. for 10 minutes. After 25 µl of the reaction mixture was subjected to agarose gel electrophoresis, a VL PCR product of about 0.44 kb was recovered by using QIAquick Gel Extraction Kit (manufactured by QIAGEN).

Figure 13:
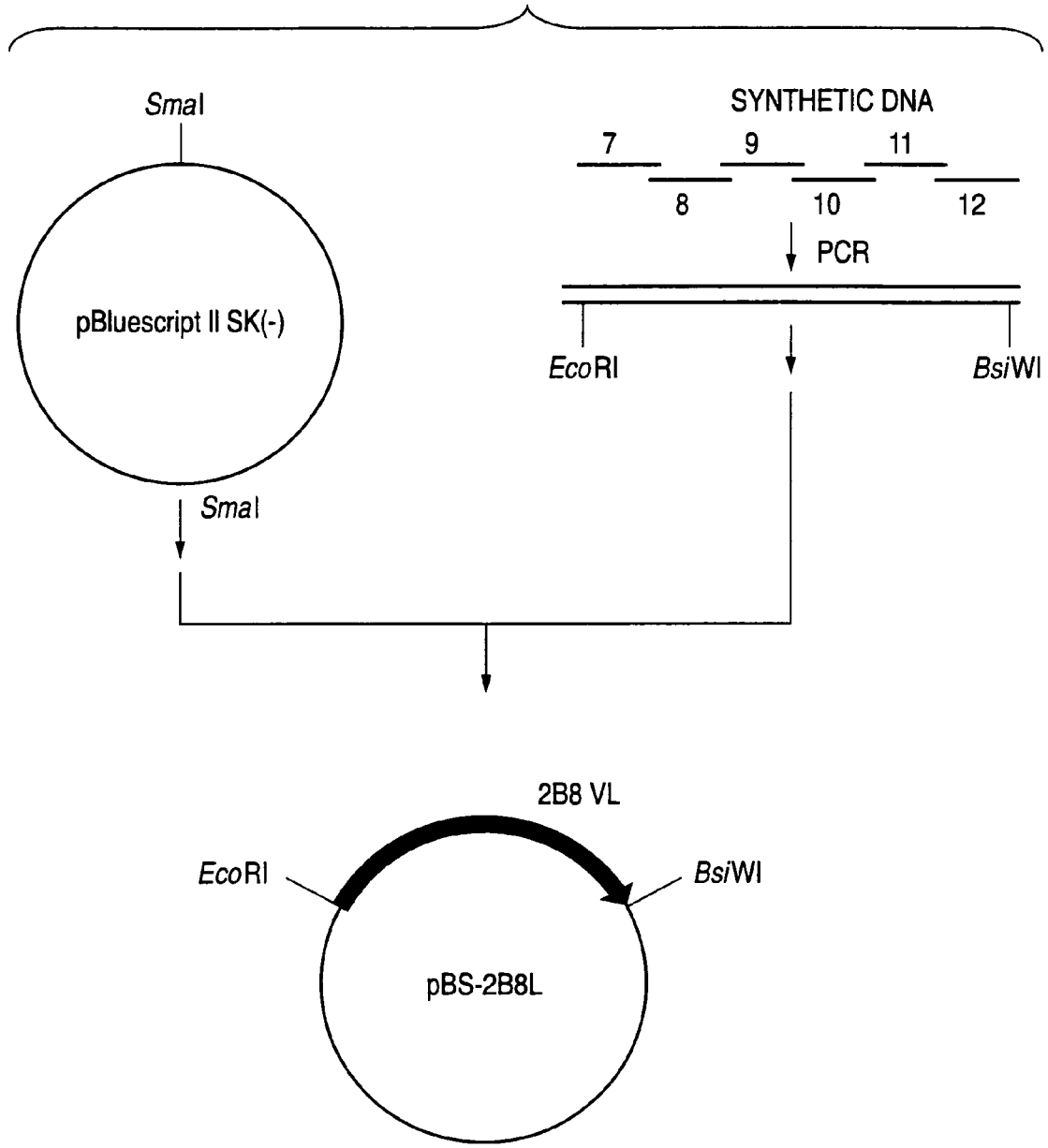
FIG. 13 shows a construction step of plasmid pBS-2B8L.

Next, 0.1 µg of a DNA fragment obtained by digesting a plasmid pBluescript II SK(-) (manufactured by Stratagene) with a restriction enzyme SmaI (manufactured by Takara Shuzo) and about 0.1 µg of the PCR product obtained in the above were added to sterile water to adjust the total volume to 7.5 µl, and then 7.5 µl of solution I of TAKARA ligation kit ver. 2 (manufactured by Takara Shuzo) and 0.3 µl of the restriction enzyme SmaI (manufactured by Takara Shuzo) were added thereto for the reaction at 22° C. for 2 hours. Using the recombinant plasmid DNA solution obtained in this manner, *E. coli* DH5α strain (manufactured by TOYOBO) was transformed. Each plasmid DNA was prepared from the transformant clones and allowed to react using BigDye Terminator Cycle Sequencing Ready Reaction Kit v2.0 (manufactured by Applied Biosystems) in accordance with the instructions attached thereto, and then the nucleotide sequence was analyzed by a DNA sequencer ABI PRISM 377 manufactured by the same company. In this manner, plasmid pBS-2B8L shown in FIG. 13 having the nucleotide sequence of interest was obtained.

(2) Construction of cDNA Encoding the V Region of H Chain of an Anti-CD20 Mouse Monoclonal Antibody A cDNA (represented by SEQ ID NO:13) encoding the amino acid sequence of the V region of H chain (hereinafter referred to as "VH") of the anti-CD20 mouse monoclonal antibody 2B8 described in WO94/11026 was constructed by PCR as follows. 2B8 is a monoclonal antibody having the same V region as Rituxan™, which is the origin of the commercial CD20 chimeric antibody Rituxan™.

First, binding nucleotide sequences of primers for amplification at the time of PCR and a restriction enzyme recognizing sequence for cloning into a vector for humanized antibody expression were added to the 5'-terminal and 3'-terminal of the nucleotide sequence of the VH described in WO94/11026. A designed nucleotide sequence was divided from the 5'-terminal side into a total of 6 nucleotide sequences each having about 100 bases (adjacent nucleotide sequences are designed in such a manner that their termini have an overlapping sequence of about 20 bases), and 6 synthetic DNA fragments, actually those represented by SEQ ID NOs:14, 15, 16, 17, 18 and 19, were prepared from them in alternate order of a sense chain and an antisense chain (consigned to GENSET).

Each oligonucleotide was added to 50 µl of a reaction mixture [KOD DNA polymerase-PCR Buffer #1 (manufactured by TOYOBO), 0.2 mM dNTPs, 1 mM magnesium chloride, 0.5 µM M13 primer M4 (manufactured by Takara Shuzo) and 0.5 µM M13 primer RV (manufactured by Takara Shuzo)] to give a final concentration of 0.1 µM, and using a DNA thermal cycler GeneAmp PCR System 9600 (manufactured by Perkin Elmer), the reaction was carried out by heating at 94° C. for 3 minutes, adding 2.5 units of KOD DNA Polymerase (manufactured by TOYOBO), subsequent 25 cycles of heating at 94° C. for 30 seconds, 55° C. for 30 seconds and 74° C. for 1 minute as one cycle and then heating at 72° C. for 10 minutes. After 25 µl of the reaction mixture was subjected to agarose gel electrophoresis, a VH PCR product of about 0.49 kb was recovered by using QIAquick Gel Extraction Kit (manufactured by QIAGEN).

Next, 0.1 µg of a DNA fragment obtained by digesting the plasmid pBluescript II SK(-) (manufactured by Stratagene) with the restriction enzyme SmaI (manufactured by Takara Shuzo) and about 0.1 µg of the PCR product obtained in the above were added to sterile water to adjust the total volume to 7.5 µl, and then 7.5 µl of solution I of TAKARA ligation kit ver. 2 (manufactured by Takara Shuzo) and 0.3 µl of the restriction enzyme SmaI (manufactured by Takara Shuzo) were added thereto to carry out the reaction at 22° C. overnight.

Using the recombinant plasmid DNA solution obtained in this manner, *E coli* DH5α strain (manufactured by TOYOBO) was transformed. Each plasmid DNA was prepared from the transformant clones and allowed to react using BigDye Terminator Cycle Sequencing Ready Reaction Kit v2.0 (manufactured by Applied Biosystems) in accordance with the manufacture's instructions attached thereto, and then the nucleotide sequence was analyzed by the DNA sequencer ABI PRISM 377 manufactured by the same company. In this manner, the plasmid pBS-2B8H shown in FIG. 14 comprising the nucleotide sequence of interest was obtained.

Next, in order to substitute the amino acid residue at position 14 from Ala to Pro, the synthetic DNA represented by SEQ ID NO:20 was designed, and base substitution was carried out by PCR using LA PCR in vitro Mutagenesis Primer Set for pBluescript II (manufactured by Takara Shuzo) as follows. After 50 µl of a reaction mixture [LA PCR Buffer II (manufactured by Takara Shuzo), 2.5 units of TaKaRa LA Taq, 0.4 mM dNTPs, 2.5 mM magnesium chloride, 50 nM T3 BcaBEST Sequencing primer (manufactured by Takara Shuzo) and 50 nM of the primer for mutagenesis (SEQ ID NO:31, manufactured by GENSET)] containing 1 ng of the plasmid pBS-2B8H was prepared, the PCR was carried out by using a DNA thermal cycler GeneAmp PCR System 9600 (manufactured by Perkin Elmer) by 25 cycles of heating at 94° C. for 30 seconds, 55° C. for 2 minutes and 72° C. for 1.5 minutes as one cycle. After 30 µl of the reaction mixture was subjected to agarose gel electrophoresis, a PCR product of about 0.44 kb was recovered by using QIAquick Gel Extraction Kit (manufactured by QIAGEN) and made into 30 µl of an aqueous mixture. In the same manner, PCR was carried out by using 50 µl of a reaction mixture (LA PCR Buffer II (manufactured by Takara Shuzo), 2.5 units of TaKaRa LA Taq, 0.4 mM dNTPs, 2.5 mM magnesium chloride, 50 nM T7 BcaBEST Sequencing primer (manufactured by Takara Shuzo) and 50 nM MUT B1 primer (manufactured by Takara Shuzo)] containing 1 ng of the plasmid pBS-2B8H. After 30 µl of the reaction mixture was subjected to agarose gel electrophoresis, a PCR product of about 0.63 kb was recovered by using QIAquick Gel Extraction Kit (manufactured by QIAGEN) and made into 30 µl of aqueous solution. Next, 0.5 µl of each of 0.44 kb PCR product and 0.63 kb PCR product thus obtained were added to 47.5 µl of a reaction mixture [LA PCR Buffer II (manufactured by Takara Shuzo), 0.4 mM dNTPs, and 2.5 mM magnesium chloride], and using a DNA thermal cycler GeneAmp PCR System 9600 (manufactured by Perkin Elmer), annealing of the DNA was carried out by heating the reaction mixture at 90° C. for 10 minutes, cooling it to 37° C. over 60 minutes and then keeping it at 37° C. for 15 minutes. After carrying out the reaction at 72° C. for 3 minutes by adding 2.5 units of TaKaRa LA Taq (manufactured by Takara Shuzo), 10 μmol of each of T3 BcaBEST Sequencing primer (manufactured by Takara Shuzo) and T7 BcaBEST Sequencing primer (manufactured by Takara Shuzo) were added thereto to make the volume of the reaction mixture to 50 μl, which was subjected to 10 cycles of heating 94° C. for 30 seconds, 55° C. for 2 minutes and 72° C. for 1.5 minutes as one cycle. After 25 μl of the reaction mixture was purified using QIA quick PCR purification kit (manufactured by QIAGEN), a half volume thereof was allowed to react at 37° C. for 1 hour using 10 units of a restriction enzyme KpnI (manufactured by Takara Shuzo) and 10 units of a restriction enzyme SacI (manufactured by Takara Shuzo). The reaction mixture was fractionated by using agarose gel electrophoresis to recover a KpnI-SacI fragment of about 0.59 kb.

Next, 1 μg of pBluescript II SK(−) (manufactured by Stratagene) was allowed to react at 37° C. for 1 hour by using 10 units of the restriction enzyme KpnI (manufactured by Takara Shuzo) and 10 units of the restriction enzyme SacI (manufactured by Takara Shuzo), and then the reaction mixture was subjected to agarose gel electrophoresis to recover a KpnI-SacI fragment of about 2.9 kb.

The PCR product-derived KpnI-SacI fragment and plasmid pBluescript II SK(−)-derived KpnI-SacI fragment thus obtained were ligated by using Solution I of DNA Ligation Kit Ver. 2 (manufactured by Takara Shuzo) in accordance with the manufacture's instructions attached thereto. Using the recombinant plasmid DNA solution obtained in this manner, E coli DH5α strain (manufactured by TOYOBO) was transformed. Each plasmid DNA was prepared from the transformant clones, and allowed to react by using BigDye Terminator Cycle Sequencing Ready Reaction Kit v2.0 (manufactured by Applied Biosystems) in accordance with the manufacture's instructions attached thereto, and then the nucleotide sequence was analyzed by the DNA sequencer ABI PRISM 377 manufactured by the same company.

Figure 14:
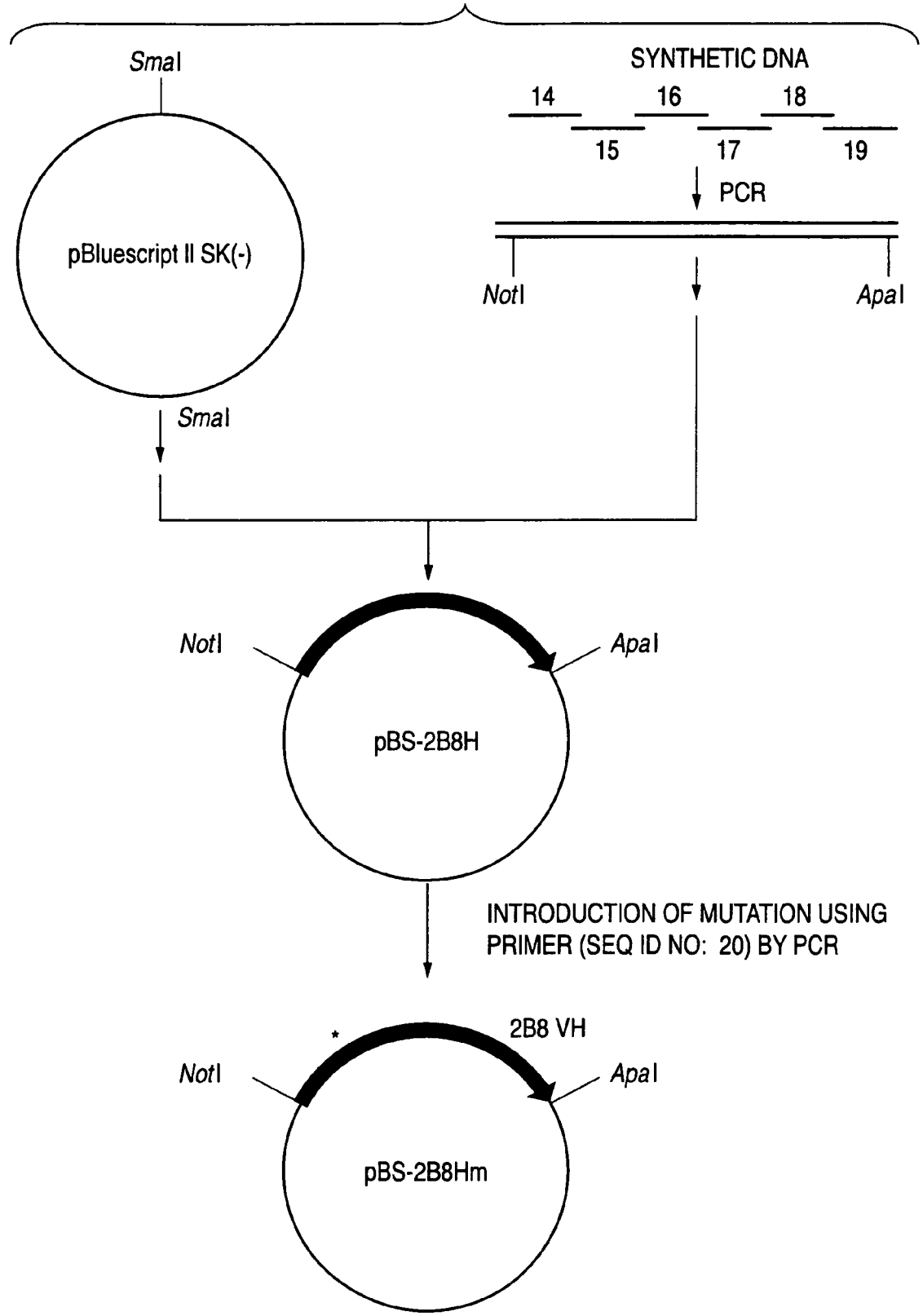
FIG. 14 shows a construction step of plasmid pBS-2B8Hm.

In this manner, plasmid pBS-2B8Hm shown in FIG. 14 comprising the nucleotide sequence of interest was obtained.

(3) Construction of Anti-CD20 Vector for Expression of Human Chimeric Antibody

An anti-CD20 human chimeric antibody (hereinafter referred to as "anti-CD20 chimeric antibody") expression vector pKANTEX2B8P was constructed as follows by using pKANTEX93, a vector for expression of humanized antibody, (Mol. Immunol., 37, 1035, 2000) and the plasmids pBS-2B8L and pBS-2B8Hm obtained in items 1(1) and (2) of this Reference Example.

After 2 μg of the plasmid pBS-2B8L obtained in item 1(1) in Example 1 was allowed to react at 55° C. for 1 hour by using 10 units of a restriction enzyme BsiWI (manufactured by New England Biolabs), followed by reaction at 37° C. for 1 hour using 10 units of a restriction enzyme EcoRI (manufactured by Takara Shuzo). The reaction mixture was fractionated by agarose gel electrophoresis to recover a BsiWI-EcoRI fragment of about 0.41 kb.

Next, 2 μg of pKANTEX93, a vector for expression of humanized antibody, was allowed to react at 55° C. for 1 hour by using 10 units of the restriction enzyme BsiWI (manufactured by New England Biolabs), followed by reaction at 37° C. for 1 hour using 10 units of the restriction enzyme EcoRI (manufactured by Takara Shuzo). The reaction mixture was fractionated by agarose gel electrophoresis to recover a BsiWI-EcoRI fragment of about 12.75 kb.

Next, the plasmid pBS-2B8L-derived BsiWI-EcoRI fragment and plasmid pKANTEX93-derived BsiWI-EcoRI fragment thus obtained were ligated by using Solution I of DNA Ligation Kit Ver. 2 (manufactured by Takara Shuzo) in accordance with the manufacture's instructions attached thereto. By using the recombinant plasmid DNA solution obtained in this manner, E. coli DH5α strain (manufactured by TOYOBO) was transformed to obtain plasmid pKANTEX2B8-L shown in FIG. 15.

Next, 2 μg of the plasmid pBS-2B8Hm obtained in item 1(2) of Example 1 was allowed to react at 37° C. for 1 hour by using 10 units of a restriction enzyme ApaI (manufactured by Takara Shuzo), followed by reaction at 37° C. for 1 hour using 10 units of a restriction enzyme NotI (manufactured by Takara Shuzo). The reaction mixture was fractionated by agarose gel electrophoresis to recover an ApaI-NotI fragment of about 0.45 kb.

Next, 3 μg of the plasmid pKANTEX2B8-L was allowed to react at 37° C. for 1 hour by using 10 units of the restriction enzyme ApaI (manufactured by Takara Shuzo), followed by reaction at 37° C. for 1 hour using 10 units of the restriction enzyme NotI (manufactured by Takara Shuzo). The reaction mixture was fractionated by agarose gel electrophoresis to recover an ApaI-NotI fragment of about 13.16 kb.

Next, the plasmid pBS-2B8Hm-derived ApaI-NotI fragment and plasmid pKANTEX2B8-L-derived ApaI-NotI fragment thus obtained were ligated by using Solution I of DNA Ligation Kit Ver. 2 (manufactured by Takara Shuzo) in accordance with the manufacture's instructions attached thereto. E. coli DH5α strain (manufactured by TOYOBO) was transformed by using the recombinant plasmid DNA solution obtained in this manner, and each plasmid DNA was prepared from the transformant clones.

Figure 15:
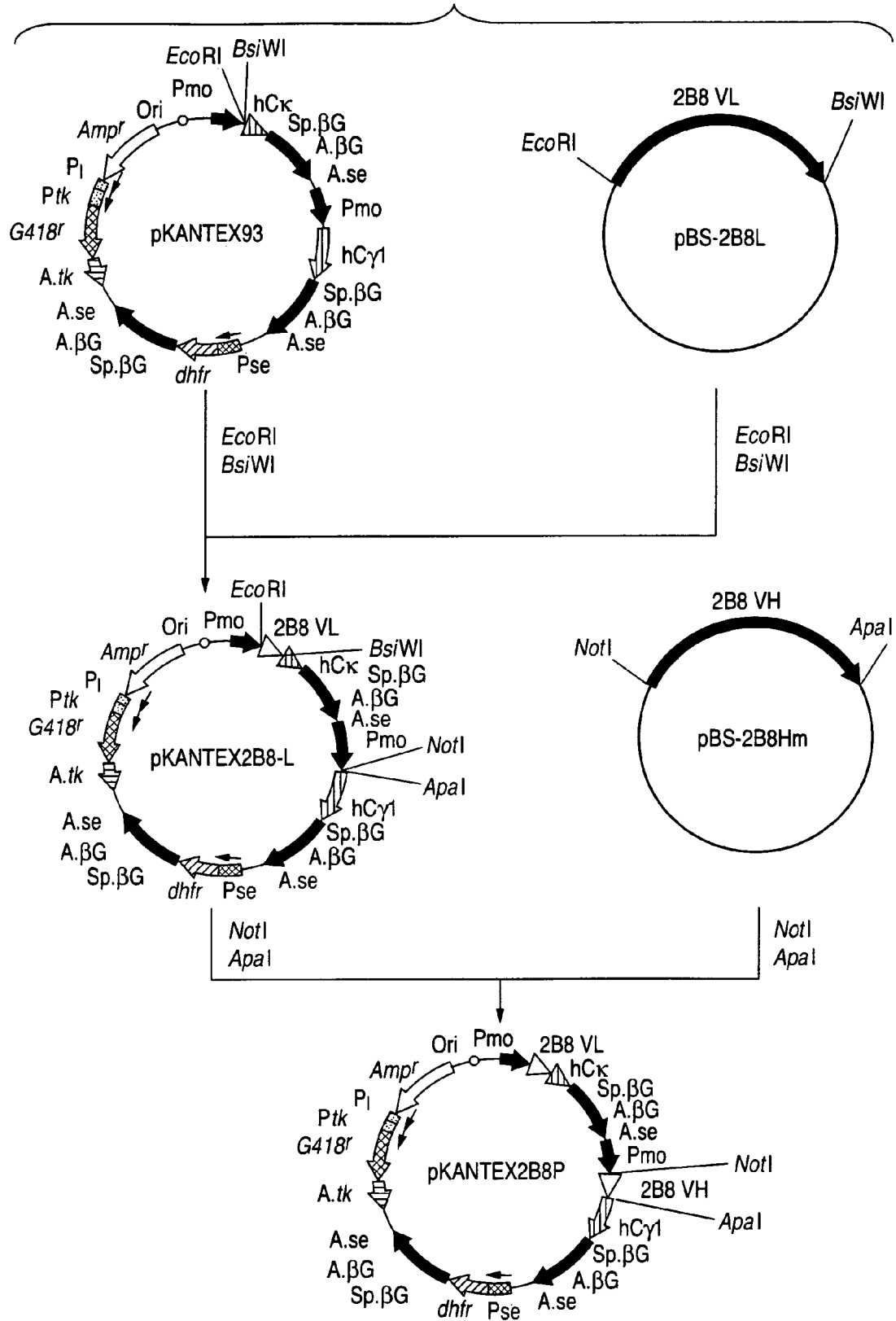
FIG. 15 shows a construction step of plasmid pKANTEX2B8P.

The nucleotide sequence of the thus obtained plasmid was analyzed by using BigDye Terminator Cycle Sequencing Ready Reaction Kit v 2.0 (manufactured by Applied Biosystems) and the DNA sequencer 377 of the same company, and it was confirmed that the plasmid pKANTEX2B8P shown in FIG. 15 into which the objective DNA had been cloned was obtained.

2. Stable Expression of Anti-CD20 Chimeric Antibody by Using Animal Cell (1) Preparation of Production Cell by Using Rat Myeloma YB2/0 Cell The anti-CD20 chimeric antibody was expressed in animal cells by using the anti-CD20 chimeric antibody expression vector, pKANTEX2B8P, obtained in item 1(3) of Reference Example as follows.

After 10 μg of the plasmid pKANTEX2B8P was introduced into $4 \times 10^6$ cells of a rat myeloma cell line YB2/0 cell (ATCC CRL 1662) by electroporation [Cytotechnology, 3, 133 (1990)], the cells were suspended in 40 ml of H-SFM medium (manufactured by GIBCO-BRL supplemented with 5% fetal calf serum (FCS)) and dispensed at 200 μl/well into a 96 well microtiter plate (manufactured by Sumitomo Bakelite). After culturing at 37° C. for 24 hours in a 5% $CO_2$ incubator, G418 was added thereto to give a concentration of 1 mg/ml, followed by culturing for 1 to 2 weeks. Culture supernatants were recovered from wells where colonies of transformants showing G418 resistance were formed and transformants became confluent, and the produced amount of the human IgG antibody in the culture supernatant was measured by ELISA described in item 2(2) of this Reference Example.

Regarding a transformant in a well where expression of human IgG antibody was found in the culture supernatant, in order to increase the antibody amount of production using a dhfr gene amplification system, it was suspended in H-SFM medium containing 1 mg/ml G418 and 50 nM methotrexate (hereinafter referred to as "ITX", manufactured by SIGMA) as an inhibitor of the dhfr gene product dihydrofolate reductase (hereinafter referred to as "DHFR") to give a density of 1 to $2\times10^5$ cells/ml, and the suspension was dispensed at 1 ml into each well of a 24 well plate (manufactured by Greiner). Culturing was carried out at 37° C. for 1 to 2 weeks in a 5% $CO_2$ incubator to induce transformants showing 50 nM MTX resistance. When a transformant became confluent in a well, the produced amount of the human IgG antibody in the culture supernatant was measured by ELISA described in item 2(2) of this Reference Example. Regarding a transformant in well where expression of human IgG antibody was found in the culture supernatant, the MTX concentration was increased to 100 nM and then to 200 µM by the same method to finally obtain a transformant which can grow in H-SFM containing 1 mg/ml G418 and 200 nM MTX and also can perform high expression of the anti-CD20 chimeric antibody. The obtained transformant was cloned by limiting dilution to obtain a clone KM3065 which expresses an anti-CD20 chimeric antibody. Also, using the determination method of transcription product of α1,6-fucosyltransferase gene described in Example 8 of WO00/61739, a clone producing a relatively low level of the transcription product was selected and used as a suitable clone.

The obtained transformant clone KM3065 which produces the anti-CD20 chimeric antibody has been deposited on Dec. 21, 2001, as FERM 7834 in International Patent Organism Depositary, National Institute of Advanced Industrial Science and Technology (Tsukuba Central 6, 1, Higashi 1-Chome Tsukuba-shi, Ibaraki-ken, Japan).

(2) Measurement of Human IgG Antibody Concentration in Culture Supernatant (ELISA)

A goat anti-human IgG (H & L) antibody (manufactured by American Qualex) was diluted with a phosphate buffered saline (hereinafter referred to as "PBS") to give a concentration of 1 µg/ml, dispensed at 50 µl/well into a 96 well plate for ELISA (manufactured by Greiner) and then allowed to stand at 4° C. overnight for adhesion. After washing with PBS, 1% bovine serum albumin (hereinafter referred to as "BSA"; manufactured by ANVC)-containing PBS (hereinafter referred to as "1% BSA-PBS") was added thereto at 100 µl/well and allowed to react at room temperature for 1 hour to block the remaining active groups. After discarding 1% BSA-PBS, culture supernatant of a transformant and variously diluted solutions of a purified human chimeric antibody were added thereto at 50 µl/well and allowed to react at room temperature for 2 hours. After the reaction, each well was washed with 0.05% Tween 20-containing PBS (hereinafter referred to as "Tween-PBS"), and then, as a secondary antibody solution, a peroxidase-labeled goat anti-human IgG (H & L) antibody solution (manufactured by American Qualex) 3,000 fold-diluted with 1% BSA-PBS was added thereto at 50 µl/well and allowed to react at room temperature for 1 hour. After the reaction and subsequent washing with Tween-PBS, an ABTS substrate solution (a solution prepared by dissolving 0.55 g of 2,2'-azino-bis(3-ethylbenzothiazoline-6-sulfonic acid)ammonium in 1 liter of 0.1 M citrate buffer (pH 4.2), and adding 1 µl/ml hydrogen peroxide just before use) was dispensed at 50 µl/well for coloration, and the absorbance at 415 nm (hereinafter referred to as "$OD_{415}$") was measured.

3. Purification of Anti-CD20 Chimeric Antibody from Culture Supernatant

The transformant cell clone KM3065 capable of expressing the anti-CD20 chimeric antibody, obtained in item 2(1) of this Reference Example, was suspended in H-SFM (manufactured by GUBCO-BRL) containing 200 nM MTX and 5% of Daigo's GF21 (manufactured by Wako Pure Chemical Industries), to give a density of $1\times10^5$ cells/ml, and dispensed at 50 ml into a 182 cm$^2$ flask (manufactured by Greiner). The cells were cultured at 37° C. for 7 days in a 5% $CO_2$ incubator, and the culture supernatant was recovered when they became confluent. The anti-CD20 chimeric antibody KM3065 was purified from the culture supernatant using a Prosep-A (manufactured by Millipore) column in accordance with the manufacture's instructions attached thereto. About 3 µg of the obtained anti-CD20 chimeric antibody KM3065 was subjected to electrophoresis in accordance with the known method [*Mature*, 227, 680 (1970)] to examine its molecular weight and purity. As a result, the purified anti-CD20 chimeric antibody KM3065 was about 150 kilodaltons (hereinafter referred to as "Kd") under non-reducing condition, and two bands of about 50 Kd and about 25 Kd were observed under reducing conditions. The sizes of the protein coincided with reports stating that an IgG type antibody has a molecular weight of about 150 Kd under non-reducing conditions and is degraded into H chain having a molecular weight of about 50 Kd and L chain having a molecular weight of about 25 Kd under reducing conditions due to cutting of the intramolecular disulfide bond (hereinafter referred to as "S—S bond") (*Antibodies, Monoclonal Antibodies*) and also almost coincided with the electrophoresis pattern of Rituxan™. Accordingly, it was confirmed that the anti-CD20 chimeric antibody KM3065 is expressed as the antibody molecule of a correct structure.

4. Sugar Chain Analysis of Anti-CD20 Chimeric Antibody

Sugar chains of the anti-CD20 chimeric antibody purified in the item 3 of this Reference Example were analyzed according to the method in the item 3 of Example 1. As a result, in the commercially available anti-CD20 chimeric antibody Rituxan™ produced by CHO/DG44 cell, the ratio of the α1,6-fucose-not-bound sugar chains was 6%, and the ratio of the α1,6-fucose-bound sugar chains was 94%. In KM3065, the ratio of the α1,6-fucose-not-bound sugar chains was 96%, and the ratio of the α1,6-fucose-bound sugar chains was 4%. The results show that KM3065 has a higher ratio of the a 1,6-fucose-not-bound sugar chains than Rituxan™.

5. Preparation of Anti-CD20 Chimeric Antibody Wherein the Ratio of Sugar Chains in which 1-Position of Fucose is Not Bound to 6-Position of N-acetylglucosamine in the Reducing End through α-Bond is 44%

A specimen was prepared by mixing KM3065 and Rituxan™ at a ratio of KM3065 Rituxan™=1:1, and its sugar chains were analyzed according to the method of item 3 in Example 1. As a result, the ratio of sugar chains in which 1-position of fucose is not bound to 6-position of N-acetylglucosamine in the reducing end through α-bond was 44%. The specimen was named anti-CD20 chimeric antibody (44%).

6. Binding Activity of Anti-CD20 Chimeric Antibody to CD20-Expressing Cell (Immunofluorescent Method)

Figure 16:
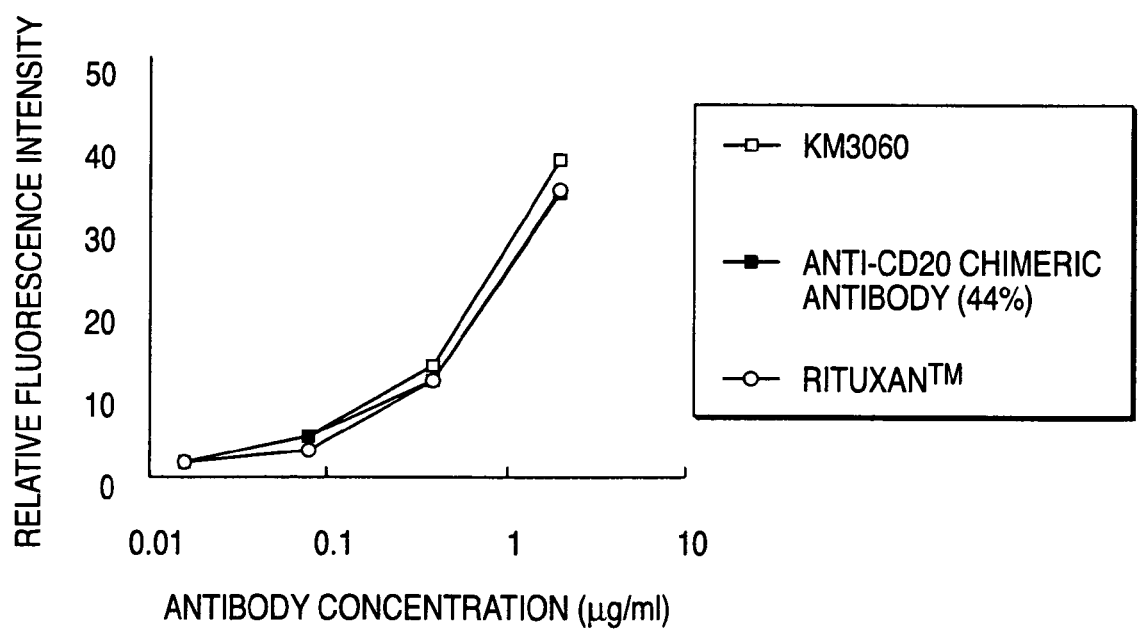
FIG. 16 shows CD20-binding activities of three kinds of anti-CD20 chimeric antibodies in which the ratios of antibody molecules bound to α1,6-fucose-free sugar chains were different while changing the concentration of the antibodies by using the immunofluorescent method. The ordinate and the abscissa show the binding activity to CD20 and the antibody concentration, respectively. "□", "●" and "○" show the activities of KM3065, anti-CCR4 chimeric antibody (44%) and Rituxan™, respectively.

Binding activities of the three purified anti-CD20 chimeric antibodies obtained in item 3 of this Reference Example, the anti-CD20 chimeric antibody (44%) and Rituxan™ were evaluated by an immunofluorescent method using a flow cytometry. A human lymphoma cell line, Raji cell (JCRB 9012), as a CD20-positive cell was dispensed at 2×10⁵ cells into each well of a 96 well U-shape plate (manufactured by Falcon). An antibody solution (a concentration of 0.039 to 40 μg/ml) prepared by diluting the anti-CD20 chimeric antibody with an FACS buffer (1% BSA-PBS, 0.02% EDTA, 0.05% NaN₃) was added thereto at 50 μl/well and allowed to react on ice for 30 minutes. After washing twice with 200 μl/well of the FACS buffer, a solution prepared by diluting a PE-labeled anti-human IgG antibody (manufactured by Coulter) 100-fold with FACS buffer was added thereto at 50 μL/well. After the reaction under shade on ice for 30 minutes and subsequent washing three times at 200 μl/well, the cells were finally suspended at 500 μl of the mixture to measure the fluorescence intensity by a flow cytometer. The measurement results are shown in FIG. 16. The three kinds of the anti-CD20 chimeric antibody were similar binding activity to CCR4, and it was found that the ratio of sugar chains in which 1-position of fucose is not bound to 6-position of N-acetylglucosamine in the reducing end has no influence on the antigen binding activity of the antibody.

While the invention has been described in detail and with reference to specific embodiments thereof, it will be apparent to one skill in the art that various changes and modifications can be made therein without departing from the spirit and scope thereof. All references cited herein are incorporated in their entirety.

This application is based on Japanese application No. 2002-106949 filed on Apr. 9, 2002, the entire contents of which being incorporated hereinto by reference.

What is claimed is:

1. A method for treating a disease in a human who is in need of treatment with an anti-CD20 antibody, wherein a CD20 antigen is expressed in a target cell relating to the disease,
   wherein the CD-20 antigen is expressed at a level of $1\times10^3$ to $1\times10^5$ molecules per cell,
   said method comprising administering to said human an anti-CD20 antibody composition,
   wherein said anti-CD20 antibody composition comprises anti-CD20 antibody molecules,
   wherein said anti-CD20 antibody molecules are produced by a CHO cell,
   wherein said anti-CD20 antibody molecules comprise a Fc region comprising complex N-glycoside-linked sugar chains bound to the Fc region though N-acetylglucosamine of the reducing terminal of the sugar chains, and
   wherein 100% of said anti-CD20 antibody molecules do not contain sugar chains with a fucose bound to the N-acetylglucosamine,
   wherein said CHO cell has no α1,6-fucosyltransferase activity as a result of a genetic engineering method, and
   wherein said CHO cell is resistant to a lectin recognizing a sugar chain in which 1-position of fucose is bound to 6-position of N-acetylglucosamine in the reducing end through α-bond in a complex N-glycoside-linked sugar chain.

2. The method according to claim 1, wherein said CD20 antigen is expressed at a level of $1\times10^3$ to $5\times10^4$ molecules per cell in said human.

3. The method according to claim 1, wherein the lectin is at least one lectin selected from the group consisting of the following (a) to (d):
   (a) a *Lens culinaris* lectin;
   (b) a *Pisum sativum* lectin;
   (c) a *Vicia faba* lectin; and
   (d) an *Aleuria aurantia* lectin.

4. The method according to claim 1, wherein the anti-CD20 antibody molecules are selected from the group consisting of the following (a) to (d):
   (a) a human antibody,
   (b) a humanized antibody, and
   (c) an antigen binding fragment thereof comprising the Fc region of (a) or (b).

5. The method according to claim 4, wherein the anti-CD20 antibody molecules are IgG molecules.

* * * * *

SEQUENCE LISTING

<160> NUMBER OF SEQ ID NOS: 20

<210> SEQ ID NO 1
<211> LENGTH: 18
<212> TYPE: PRT
<213> ORGANISM: Homo sapiens

<400> SEQUENCE: 1

Asp Glu Ser Ile Tyr Ser Asn Tyr Tyr Leu Tyr Glu Ser Ile Pro Lys
 1               5                  10                  15

Pro Cys

<210> SEQ ID NO 2
<211> LENGTH: 57
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 2
taaaactagt ctgcagcgta cggacccctc accatgacaa cacccagaaa ttcagta        57

<210> SEQ ID NO 3
<211> LENGTH: 49
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 3
tagtggatcc aaatcactta aggagagctg tcattttcta ttggtgagg               49

<210> SEQ ID NO 4
<211> LENGTH: 894
<212> TYPE: DNA
<213> ORGANISM: Homo sapiens

<400> SEQUENCE: 4
atgacaacac ccagaaattc agtaaatggg actttcccgg cagagccaat gaaaggccct        60
attgctatgc aatctggtcc aaaaccactc ttcaggagga tgtcttcact ggtgggcccc       120
acgcaaagct tcttcatgag ggaatctaag actttggggg ctgtccagat tatgaatggg       180
ctcttccaca ttgccctggg gggtcttctg atgatcccag cagggatcta tgcacccatc       240

```
tgtgtgactg tgtggtaccc tctctgggga ggcattatgt atattatttc cggatcactc    300
ctggcagcaa cggagaaaaa ctccaggaag tgtttggtca aggaaaaat gataatgaat     360 tcattgagcc tctttgctgc catttctgga atgattcttt caatcatgga catacttaat    420
attaaaattt cccatttttt aaaaatggag agtctgaatt ttattagagc tcacacacca    480
tatattaaca tatacaactg tgaaccagct aatccctctg agaaaaactc cccatctacc    540
caatactgtt acagcataca atctctgttc ttgggcattt tgtcagtgat gctgatcttt    600
gccttcttcc aggaacttgt aatagctggc atcgttgaga tgaatggaa agaacgtgc      660 tccagaccca atctaacat agttctcctg tcagcagaag aaaaaaaga acagactatt      720 gaaataaaag aagaagtggt tgggctaact gaaacatctt cccaaccaaa gaatgaagaa    780
gacattgaaa ttattccaat ccaagaagag gaagaagaag aaacagagac gaactttcca    840
gaacctcccc aagatcagga atcctcacca atagaaaatg acagctctcc ttaa          894

<210> SEQ ID NO 5
<211> LENGTH: 297
<212> TYPE: PRT
<213> ORGANISM: Homo sapiens

<400> SEQUENCE: 5

Met Thr Thr Pro Arg Asn Ser Val Asn Gly Thr Phe Pro Ala Glu Pro
  1               5                  10                  15

Met Lys Gly Pro Ile Ala Met Gln Ser Gly Pro Lys Pro Leu Phe Arg
                 20                  25                  30

Arg Met Ser Ser Leu Val Gly Pro Thr Gln Ser Phe Phe Met Arg Glu
             35                  40                  45

Ser Lys Thr Leu Gly Ala Val Gln Ile Met Asn Gly Leu Phe His Ile
         50                  55                  60

Ala Leu Gly Gly Leu Leu Met Ile Pro Ala Gly Ile Tyr Ala Pro Ile
 65                  70                  75                  80

Cys Val Thr Val Trp Tyr Pro Leu Trp Gly Gly Ile Met Tyr Ile Ile
                 85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu Glu
```

```
                    260             265             270
Glu Glu Thr Glu Thr Asn Phe Pro Gly Pro Pro Gln Asp Gln Glu Ser
        275                 280                 285
Ser Pro Ile Glu Asn Asp Ser Ser Pro
    290                 295

<210> SEQ ID NO 6
<211> LENGTH: 384
<212> TYPE: DNA
<213> ORGANISM: Mus musculus

<400> SEQUENCE: 6 atg gat ttt cag gtg cag att atc agc ttc ctg cta atc agt gct tca         48
Met Asp Phe Gln Val Gln Ile Ile Ser Phe Leu Leu Ile Ser Ala Ser
  1               5                  10                  15 gtc ata atg tcc aga gga caa att gtt ctc tcc cag tct cca gca atc         96
Val Ile Met Ser Arg Gly Gln Ile Val Leu Ser Gln Ser Pro Ala Ile
             20                  25                  30 ctg tct gca tct cca ggg gag aag gtc aca atg act tgc agg gcc agc        144
Leu Ser Ala Ser Pro Gly Glu Lys Val Thr Met Thr Cys Arg Ala Ser
         35                  40                  45 tca agt gta agt tac atc cac tgg ttc cag cag aag cca gga tcc tcc        192
Ser Ser Val Ser Tyr Ile His Trp Phe Gln Gln Lys Pro Gly Ser Ser
     50                  55                  60 ccc aaa ccc tgg att tat gcc aca tcc aac ctg gct tct gga gtc cct        240
Pro Lys Pro Trp Ile Tyr Ala Thr Ser Asn Leu Ala Ser Gly Val Pro
 65                  70                  75                  80 gtt cgc ttc agt ggc agt ggg tct ggg act tct tac tct ctc acc atc        288
Val Arg Phe Ser Gly Ser Gly Ser Gly Thr Ser Tyr Ser Leu Thr Ile
                 85                  90                  95 agc aga gtg gag gct gaa gat gct gcc act tat tac tgc cag cag tgg        336
Ser Arg Val Glu Ala Glu Asp Ala Ala Thr Tyr Tyr Cys Gln Gln Trp
            100                 105                 110 act agt aac cca ccc acg ttc gga ggg ggg acc aag ctg gaa atc aaa        384
Thr Ser Asn Pro Pro Thr Phe Gly Gly Gly Thr Lys Leu Glu Ile Lys
        115                 120                 125

<210> SEQ ID NO 7
<211> LENGTH: 91
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 7
caggaaacag ctatgacgaa ttcgcctcct caaaatggat tttcaggtgc agattatcag        60
cttcctgcta atcagtgctt cagtcataat g                                        91

<210> SEQ ID NO 8
<211> LENGTH: 91
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 8
gtgaccttct cccctggaga tgcagacagg attgctggag actgggagag aacaatttgt        60
cctctggaca ttatgactga agcactgatt a                                        91
```

<210> SEQ ID NO 9
<211> LENGTH: 90
<212> TYPE: DNA
<213> ORGANISM: Artificial Sequence
<220> FEATURE:
<223> OTHER INFORMATION: Description of Artificial Sequence: Synthetic DNA

<400> SEQUENCE: 9

```
ctccagggga gaaggtcaca atgacttgca gggccagctc aagtgtaagt tacatccact      60
ggttccagca gaagccagga tcctccccca                                       90
```

<210> SEQ ID NO 10
<211> LENGTH: 89
<212> TYPE: DNA
<213> ORGANISM: Artificial Sequence
<220> FEATURE:
<223> OTHER INFORMATION: Description of Artificial Sequence: Synthetic DNA

<400> SEQUENCE: 10

```
ccagacccac tgccactgaa gcgaacaggg actccagaag ccaggttgga tgtggcataa      60
atccagggtt tgggggagga tcctggctt                                        89
```

<210> SEQ ID NO 11
<211> LENGTH: 91
<212> TYPE: DNA
<213> ORGANISM: Artificial Sequence
<220> FEATURE:
<223> OTHER INFORMATION: Description of Artificial Sequence: Synthetic DNA

<400> SEQUENCE: 11

```
tcagtggcag tgggtctggg acttcttact ctctcaccat cagcagagtg gaggctgaag      60
atgctgccac ttattactgc cagcagtgga c                                     91
```

<210> SEQ ID NO 12
<211> LENGTH: 90
<212> TYPE: DNA
<213> ORGANISM: Artificial Sequence
<220> FEATURE:
<223> OTHER INFORMATION: Description of Artificial Sequence: Synthetic DNA

<400> SEQUENCE: 12

```
gttttcccag tcacgaccgt acgtttgatt tccagcttgg tccccctcc gaacgtgggt       60
gggttactag tccactgctg gcagtaataa                                       90
```

<210> SEQ ID NO 13
<211> LENGTH: 420
<212> TYPE: DNA
<213> ORGANISM: Mus musculus

<400> SEQUENCE: 13

```
atg ggt tgg agc ctc atc ttg ctc ttc ctt gtc gct gtt gct acg cgt        48
Met Gly Trp Ser Leu Ile Leu Leu Phe Leu Val Ala Val Ala Thr Arg
 1               5                  10                  15 gtc ctg tcc cag gta caa ctg cag cag cct ggg gct gag ctg gtg aag        96
Val Leu Ser Gln Val Gln Leu Gln Gln Pro Gly Ala Glu Leu Val Lys
             20                  25                  30 cct ggg gcc tca gtg aag atg tcc tgc aag gct tct ggc tac aca ttt       144
Pro Gly Ala Ser Val Lys Met Ser Cys Lys Ala Ser Gly Tyr Thr Phe
         35                  40                  45
```

```
acc agt tac aat atg cac tgg gta aaa cag aca cct ggt cgg ggc ctg     192
Thr Ser Tyr Asn Met His Trp Val Lys Gln Thr Pro Gly Arg Gly Leu
     50                  55                  60 gaa tgg att gga gct att tat ccc gga aat ggt gat act tcc tac aat     240
Glu Trp Ile Gly Ala Ile Tyr Pro Gly Asn Gly Asp Thr Ser Tyr Asn
 65                  70                  75                  80 cag aag ttc aaa ggc aag gcc aca ttg act gca gac aaa tcc tcc agc     288
Gln Lys Phe Lys Gly Lys Ala Thr Leu Thr Ala Asp Lys Ser Ser Ser
                 85                  90                  95 aca gcc tac atg cag ctc agc agc ctg aca tct gag gac tct gcg gtc     336
Thr Ala Tyr Met Gln Leu Ser Ser Leu Thr Ser Glu Asp Ser Ala Val
            100                 105                 110 tat tac tgt gca aga tcg act tac tac ggc ggt gac tgg tac ttc aat     384
Tyr Tyr Cys Ala Arg Ser Thr Tyr Tyr Gly Gly Asp Trp Tyr Phe Asn
        115                 120                 125 gtc tgg ggc gca ggg acc acg gtc acc gtc tct gca                     420
Val Trp Gly Ala Gly Thr Thr Val Thr Val Ser Ala
130                 135                 140

<210> SEQ ID NO 14
<211> LENGTH: 99
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 14
caggaaacag ctatgacgcg gccgcgaccc ctcaccatgg gttggagcct catcttgctc     60
ttccttgtcg ctgttgctac gcgtgtcctg tcccaggta                           99

<210> SEQ ID NO 15
<211> LENGTH: 98
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 15
atgtgtagcc agaagccttg caggacatct tcactgaggc cccagccttc accagctcag     60
ccccaggctg ctgcagttgt acctgggaca ggacacgc                             98

<210> SEQ ID NO 16
<211> LENGTH: 97
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 16
caaggcttct ggctacacat ttaccagtta caatatgcac tgggtaaaac agacacctgg     60
tcggggcctg aatggattg agctattta tcccgga                               97

<210> SEQ ID NO 17
<211> LENGTH: 99
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 17
```

-continued

```
gtaggctgtg ctggaggatt tgtctgcagt caatgtggcc ttgcctttga acttctgatt      60
gtaggaagta tcaccatttc cgggataaat agctccaat                              99

<210> SEQ ID NO 18
<211> LENGTH: 99
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 18
aatcctccag cacagcctac atgcagctca gcagcctgac atctgaggac tctgcggtct      60
attactgtgc aagatcgact tactacggcg gtgactggt                              99

<210> SEQ ID NO 19
<211> LENGTH: 98
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 19
gttttcccag tcacgacggg cccttggtgg aggctgcaga gacggtgacc gtggtccctg      60
cgccccagac attgaagtac cagtcaccgc cgtagtaa                               98

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 20
gagctggtga agcctggggc ctcag                                             25
```